United States Patent
Kirstgen et al.

Patent Number: 6,031,110
Date of Patent: Feb. 29, 2000

[54] ORTHO-SUBSTITUTED 2-METHOXYIMINOPHENYL-N-METHYLACETAMIDES

[75] Inventors: Reinhard Kirstgen, Neustadt; Wassilios Grammenos, Ludwigshafen; Herbert Bayer, Mannheim; Reinhard Doetzer, Weinheim; Hartmann Koenig, Limburgerhof; Klaus Oberdorf, Heidelberg; Hubert Sauter; Horst Wingert, both of Mannheim; Gisela Lorenz, Neustadt; Eberhard Ammermann, Heppenheim; Volker Harries, Frankenthal, all of Germany

[73] Assignee: BASF Aktiengesellschaft, Ludwigshafen, Germany

[21] Appl. No.: 08/505,288

[22] PCT Filed: Feb. 12, 1994

[86] PCT No.: PCT/EP94/00408

§ 371 Date: Aug. 21, 1995

§ 102(e) Date: Aug. 21, 1995

[87] PCT Pub. No.: WO94/19331

PCT Pub. Date: Sep. 1, 1994

[30] Foreign Application Priority Data

Feb. 23, 1993 [DE] Germany .............................. 43 05 502

[51] Int. Cl.[7] ...................... C07D 231/20; C07D 231/18
[52] U.S. Cl. ..................... 548/370.1; 548/366.7
[58] Field of Search .............. 548/366.7, 370.1; 514/407

[56] References Cited

U.S. PATENT DOCUMENTS

| | | | |
|---|---|---|---|
| 5,185,342 | 2/1993 | Hayase et al. | 514/274 |
| 5,395,854 | 3/1995 | Brand et al. | 514/619 |
| 5,510,344 | 4/1996 | Cliff et al. | 514/212 |

FOREIGN PATENT DOCUMENTS

| | | |
|---|---|---|
| 1 177 081 | 9/1981 | Canada . |
| 4-182461 | 6/1992 | Japan . |
| 2 253 624 | 1/1991 | United Kingdom . |
| WO-A 92/13830 | 1/1991 | WIPO . |

OTHER PUBLICATIONS

Can. J. Chem. 57, 904 ('79).
Chem. Pharm. Bull. 33, 3479 ('85).
Chem. Pharm. Bull. 15, 1025 ('67).
Acta Chem. Scand. 17, 144 ('63).
Acta Chem. Scand. 7, 374 ('53).
Agric. Biol. Chem. 50, 1831 ('86).
J. Org. Chem. 23, 1021 ('58).

*Primary Examiner*—Patricia L. Morris
*Attorney, Agent, or Firm*—Oblon, Spivak, McClelland, Maier & Neustadt, P.C.

[57] ABSTRACT

Compounds of the general formula I

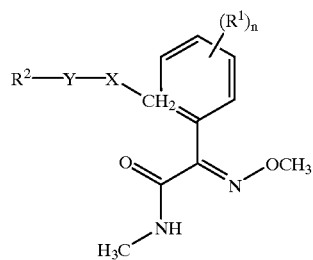

where the index and the substituents have the following meanings:

n is 0 or 1 to 4;
X is O or S;
Y is a five-membered heteroaromatic ring;
$R^1$ is nitro; cyano; halogen; alkyl; haloalkyl; alkoxy; haloalkoxy; alkylthio; phenyl or phenoxy;
$R^2$ is hydrogen; alkyl, alkenyl or alkynyl;

or a saturated or unsaturated ring which, in addition to carbon atoms, can also contain hetero atoms as ring members are described.

3 Claims, No Drawings

ORTHO-SUBSTITUTED 2-METHOXYIMINOPHENYL-N-METHYLACETAMIDES

The present invention relates to compounds of the general formula

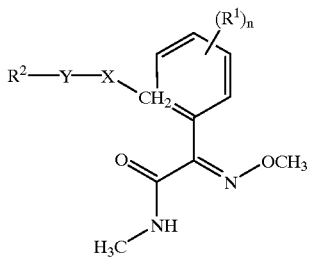

where the index and the substituents have the following meanings:

n is 0, 1, 2, 3 or 4, it being possible for the radicals $R^1$ to be different if n is greater than 1;

X is O or S;

Y is a five-membered heteroaromatic ring which, in addition to $R^2$, can also carry one or two radicals from the group consisting of Cl, $CH_3$, $CF_3$ and $OCH_3$;

$R^1$ is nitro; cyano; halogen;
  $C_1$-$C_4$-alkyl; $C_1$-$C_4$-haloalkyl; $C_1$-$C_4$-alkoxy; $C_1$-$C_4$-haloalkoxy; $C_1$-$C_4$-alkylthio;
  phenyl or phenoxy, it being possible for the aromatic rings to carry one to five halogen atoms or one to three of the following radicals: halogen, $C_1$-$C_4$-alkyl, $C_1$-$C_4$-haloalkyl, $C_1$-$C_4$-alkoxy, $C_1$-$C_4$-haloalkoxy and $C_1$-$C_4$-alkylthio;
  or, if n is greater than 1, a 1,3-butadiene-1,4-diyl group which is bonded to two adjacent C atoms of the phenyl radical and which for its part can carry one to four halogen atoms or one or two of the following radicals: nitro, cyano, halogen, $C_1$-$C_4$-alkyl, $C_1$-$C_4$-haloalkyl, $C_1$-$C_4$-alkoxy, $C_1$-$C_4$-haloalkoxy and $C_1$-$C_4$-alkylthio;

$R^2$ is hydrogen;
  unsubstituted or substituted alkyl, alkenyl or alkynyl;
  an unsubstituted or substituted, saturated or mono- or diunsaturated ring which, in addition to carbon atoms, can contain one to three of the following hetero atoms as ring members: oxygen, sulfur and nitrogen;
  or an unsubstituted or substituted, mono- or binuclear aromatic ring which, in addition to carbon atoms, can contain one to four nitrogen atoms or one or two nitrogen atoms and an oxygen or sulfur atom or an oxygen or sulfur atom as ring members.

The invention further relates to processes for preparing these compounds, compositions containing them and their use for the control of fungi and pests.

Substituted 2-alkoxyiminophenylacetamides are known (EP-A 398 692, EP-A 477 631, JP-A 4 182 461, WO 92/13 830 and GB 22 53 624). The compounds have fungicidal and partly also insecticidal action (EP-A 477 631). Their action, however, is unsatisfactory.

It has surprisingly been found that the compounds of the general formula I according to the invention have a greatly improved activity and plant tolerability.

In addition, processes for preparing these compounds, compositions containing them and their use for the control of fungi and pests have been found.

The compounds of the formula I are prepared in analogy to various methods known per se from the literature. In the synthesis of the compounds I, the sequence in which the groups $R^2$—Y—$XCH_2$— or group [sic] —C(=$NOCH_3$)—CO—$NHCH_3$ are synthesized from the corresponding precursors is in general insignificant.

These groups are particularly preferably obtained by the processes described below, the group which is not involved in the reaction in each case being shown in the following reaction schemes in a simplified manner for better clarity: the group $R^2$—Y—$XCH_2$— or its precursor as R* and the group —C(=$NOCH_3$)—CO—$NHCH_3$ or its precursor as $R^\#$.

A: Process for Synthesizing the Group $R^2$—Y—$XCH_2$—

The compounds of the general formulae I and II are obtained by reaction of IA or IIA with hydroxy- or mercapto-substituted five-membered ring heteroaromatic systems III in inert solvents in the presence of a base.

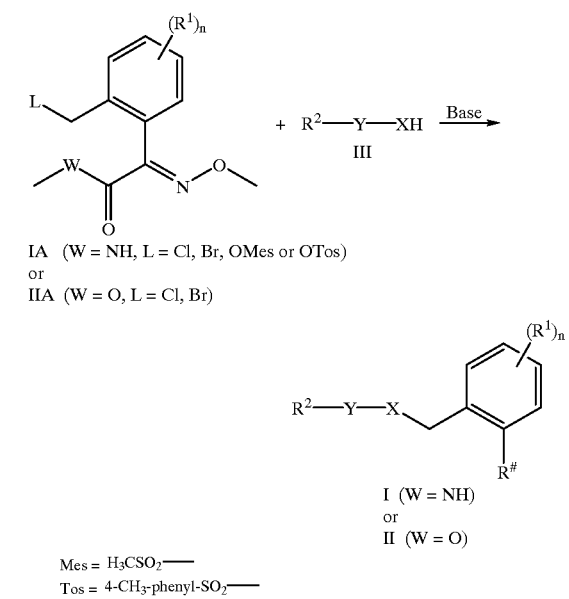

This reaction is customarily carried out at from 0° C. to 80° C., preferably 20° C. to 60° C. Suitable solvents are aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitrites such as acetonitrile and propionitrile, alcohols such as methanol, ethanol, n-propanol, isopropanol, n-butanol and tert-butanol, ketones such as acetone and methyl ethyl ketone, as well as dimethyl sulfoxide, dimethylformamide, dimethylacetamide, 1,3-dimethylimidazolidin-2-one and 1,3-dimethyltetrahydro-2(1H)-pyrimidinine [sic], particularly preferably dichloromethane, acetone and dimethylformamide.

Mixtures of the solvents mentioned can also be used.

Suitable bases are generally inorganic compounds such as alkali metal and alkaline earth metal hydroxides such as lithium hydroxide, sodium hydroxide, potassium hydroxide, calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as potassium carbonates [sic] and calcium carbonate and also alkali metal hydrogen carbonates such as potassium carbonate and calcium carbonate [sic] and also alkali metal hydrogen carbonates such as sodium hydrogen carbonate, organometallic compounds, in particular alkali metal alkyls such as methyllithium, butyllithium and phenyllithium, alkymagnesium [sic] halides such as methylmagnesium chloride and also alkali metal and alkaline earth metal alkoxides such as sodium methoxide, sodium methoxide [sic], potassium ethoxide, potassium tert-butoxide and dimethoxymagnesium and additionally organic bases, eg. tertiary amines such as trimethylamine, triethylamine, diisopropylethylamine and N-methylpiperidine, pyridine, substituted pyridines such as collidine, lutidine and 4-dimethylaminopyridine and also bicyclic amines.

Sodium hydroxide, sodium hydride, potassium carbonate and potassium tert-butoxide are particularly preferred.

The bases are in general used in equimolar amounts, in an excess or if appropriate as a solvent.

It may be advantageous for the reaction to add a catalytic amount of a crown ether such as eg. 18-crown-6 or 15-crown-5.

The reaction can also be carried out in a two-phase system consist [sic] of a solution of alkali metal or alkaline earth metal hydroxides or alkali metal or alkaline earth metal carbonates in water and an organic phase such as eg. halogenated hydrocarbons. Phase-transfer catalysts employed can be ammonium halides and tetrafluoborates such as eg. benzyltriethylammonium chloride, benzyltributylammonium bromide, tetrabutylammonium chloride, hexadecyltrimethylammonium bromide or tetrabutylammonium tetrafluoborate and also phosphonium halides such as tetrabutylphosphonium chloride or tetraphenylphosphonium bromide.

It may be advantageous for the reaction first to treat the compounds III with base and to react the resulting salt with the compounds IA or IIA.

The starting compounds IA.1 (L=Cl) and IA.2 (L=Br), cf. EP477631, Tab. 1, No. 332 and 333, are prepared from corresponding alkoxy or aryloxy compounds IB by cleavage

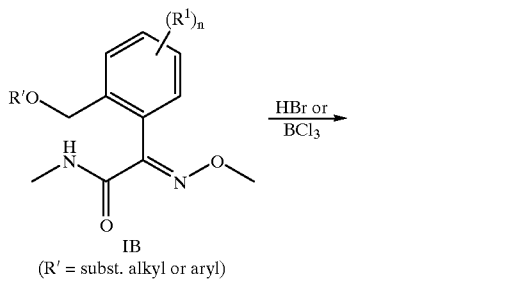

IB
(R' = subst. alkyl or aryl)

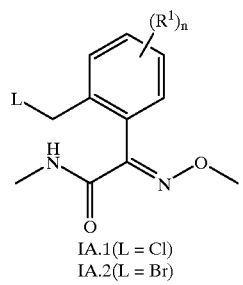

IA.1(L = Cl)
IA.2(L = Br)

with eg. boron trichloride (for IA.1) or with hydrogen bromide (for IA.2) in inert solvents such as halogenated hydrocarbons at from −30° C. to +40° C. An advantageous preparation from R'=2-tolyl (see EP-A477631, Tab. 1, No. 94) is described in Examples 1 to 3.

The preparation of the starting compounds IIA is described several times in the literature, cf. EP-A 363 818.

The preparation of the hydroxy- or mercapto-[lacuna] five-membered ring heterocycles III is described in the literature, or can be carried out analogously to the synthesis routes shown there, cf. J. Heterocycl. Chem. 19 (1982), 541 ff; Acta Chem. Scand. 7 (1953), 374 ff; Chem. Pharm. Bull. 33 (1985), 3479 ff; Acta Chem. Scand. 17 (1963), 144ff; Canadian Patent 1 177 081; Can J. Chem. 57 (1979), 904 ff; Ann. Chem. 338 (1905), 273 ff; German Laid-Open Application DOS 1029827; Chem. Pharm. Bull. 15 (1967), 1025 ff; Agric. Biol. Chem. 50 (1986), 1831 ff; J. Org. Chem. 23 (1958), 1021 ff; Chem. Ber. 22 (1889), 2433 ff; Chem. Ber. 24 (1891), 369 ff; J. Med. Chem. 15 (1971), 39 ff; J. Am. Chem. Soc. 76 (1954), 4450 ff.

B: Process for Synthesizing the Group —C(=NOCH$_3$)—CO—NHCH$_3$

The compounds of the general formula I are obtained by aminolysis of the corresponding 2-methoxyiminophenylacetic acid esters II (cf. Houben-Weyl Vol. E 5, p. 983 ff).

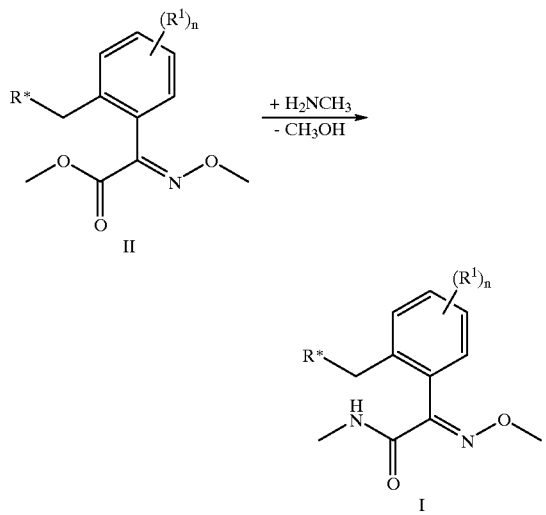

This reaction is customarily carried out at from 0° C. to 60° C;, preferably 10° C. to 30° C.

Methylamine can be metered into a solution of II by gaseous introduction or as an aqueous solution.

Suitable solvents are aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, and alcohols such as methanol, ethanol, n-propanol, isopropanol, n-butanol and tert-butanol, particularly preferably methanol, toluene and tetrahydrofuran.

Mixtures of the solvents mentioned can also be used.

With respect to the biological action against pests such as in particular harmful fungi, insects, nematodes and arachnida, those compounds I are particularly suitable in which the index and the substituents have the following meanings:

n is 0, 1, 2, 3 or 4, it being possible for the radicals R$^1$ to be different if n is greater than 1, in particular 0 or 1;

X is O or S;

Y is a five-membered ring heteroaromatic system such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-triazol-5-yl and 1,2,3-triazol-4-yl, in particular 2-furyl, 2-thienyl, 3-pyrrolyl, 3-isoxazolyl, 5-isoxazolyl, 3-isothiazolyl, 3-pyrazolyl, 4-pyrazolyl, 5-pyrazolyl, 2-oxazolyl, 4-oxazolyl, 2-thiazolyl, 4-thiazolyl, 1,2,4-oxadiazol-5-yl, 1,2,4-thiadiazol-5-yl, 1,2,4-triazol-3-yl, 1,3,4-oxadiazol-2-yl and 1,3,4-thiadiazol-2-yl;

$R^1$ is nitro;
  cyano;
  halogen such as fluorine, chlorine, bromine and iodine, in particular fluorine and chlorine;
  $C_1$–$C_4$-alkyl such as methyl, ethyl, propyl, 1-methylethyl, butyl, 1-methylpropyl, 2-methylpropyl and 1,1-dimethylethyl, preferably methyl and 1-methylethyl, in particular methyl;
  $C_1$–$C_4$-haloalkyl, particularly $C_1$–$C_2$-haloalkyl such as trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably difluoromethyl and trifluoromethyl, in particular trifluoromethyl;
  $C_1$–$C_4$-alkoxy such as methoxy, ethoxy, propyloxy, 1-methylethoxy, butyloxy, 1-methylpropyloxy, 2-methylpropyloxy and 1,1-dimethylethoxy, preferably methoxy and ethoxy, 1-methylethoxy, in particular methoxy;
  $C_1$–$C_4$-haloalkoxy, particularly $C_1$–$C_2$-haloalkoxy such as dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, preferably difluoromethoxy and chlorodifluoromethoxy, in particular difluoromethoxyoxy [sic];
  $C_1$–$C_4$-alkylthio such as methylthio, ethylthio, propylthio, 1-methylethylthio, butylthio, 1-methylpropylthio, 2-methylpropylthio and 1,1-dimethylethylthio, preferably methylthio, ethylthio and 1-methylethylthio, in particular methylthio;
  phenyl or phenoxy, where the aromatic rings can carry one to five halogen atoms such as fluorine, chlorine, bromine and iodine, in particular fluorine and chlorine or one to three of the following radicals:
    halogen such as mentioned above;
    $C_1$–$C_4$-alkyl such as mentioned above, in particular methyl;
    $C_1$–$C_4$-haloalkyl, particularly $C_1$–$C_2$-haloalkyl such as mentioned above, in particular trifluoromethyl;
    $C_1$–$C_4$-alkoxy such as mentioned above, in particular methoxy;

or, if n>1, a 1,3-butadiene-1,4-diyl group which is bonded to two adjacent C atoms of the parent structure and which for its part can carry one to four halogen atoms such as fluorine, chlorine, bromine and iodine, in particular fluorine and chlorine, or one or two of the following radicals:
    halogen such as mentioned above,
    nitro,
    cyano,
    $C_1$–$C_4$-alkyl such as mentioned above, in particular methyl;
    $C_1$–$C_4$-haloalkyl, particularly $C_1$–$C_2$-haloalkyl such as mentioned above, in particular trifluoromethyl;
    $C_1$–$C_4$-alkoxy such as mentioned above, in particular methoxy;

$R^2$ is unsubstituted or substituted alkyl, in particular $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably methyl, ethyl, 1-methylethyl, 1-methylpropyl, 1,1-dimethylethyl, 1,1-dimethylpropyl and 2,3-dimethylbutyl, in particular methyl, 1-methylethyl and 1,1-dimethylethyl;

unsubstituted or substituted alkenyl, particularly $C_2$–$C_6$-alkenyl such as ethenyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, preferably 1-propenyl, 1-methyl-2-propenyl, 1,1-dimethyl-2-propenyl, 1,1-dimethyl-2-butenyl, in particular 2-propenyl and 1,1-dimethyl-2-propenyl;

or unsubstituted or substituted alkynyl, particularly $C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, preferably 2-propynyl, 1-methyl-2-propynyl, 1-methyl-2-butynyl, 1,1-dimethyl-2-propynyl and 1,1-dimethyl-2-butynyl, in particular 2-propynyl, 1-methyl-2-propynyl and 1,1-dimethyl-2-propynyl;

an unsubstituted or substituted, saturated or mono- or diunsaturated ring which, in addition to carbon atoms, can contain one to three of the following hetero atoms as ring members: oxygen, sulfur and nitrogen, for example carbocycles such as cyclopropyl, cyclopentyl, cyclohexyl, cyclopent-2-enyl, cyclohex-2-enyl, 5- to 6-membered, saturated or unsaturated heterocycles, containing one to three nitrogen atoms and/or an oxygen or sulfur atom such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl;

or an unsubstituted or substituted mono- or binuclear aromatic ring system which, in addition to carbon atoms, can contain one to four nitrogen atoms or one or two nitrogen atoms and an oxygen or sulfur atom or an oxygen or sulfur atom as ring members, ie. aryl radicals such as phenyl and naphthyl, preferably phenyl or 1- or 2-naphthyl, and hetaryl radicals, for example 5-membered ring heteroaromatics containing one to three nitrogen atoms and/or an oxygen or sulfur atom such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered ring heteroaromatics containing one to four nitrogen atoms as hetero atoms such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The mono- or binuclear aromatic or heteroaromatic systems mentioned under the radicals can for their part be partially or completely halogenated, ie. the hydrogen atoms of these groups can be replaced partially or completely by halogen atoms such as fluorine, chlorine, bromine and iodine, preferably fluorine and chlorine.

In addition to the designated halogen atoms, these mono- or bi-nuclear aromatic or heteroaromatic systems can additionally carry one to three of the following substituents:

nitro;

cyano, thiocyanato;

alkyl, particularly $C_1$–$C_6$-alkyl such as mentioned above, preferably methyl, ethyl, 1-methylethyl, 1,1-dimethylethyl, butyl, hexyl, in particular methyl and 1-methylethyl;

alkenyl, particularly preferably $C_2$–$C_6$-alkenyl such as mentioned above, preferably ethenyl, 1-propenyl, 2-propenyl, 1-methyl-2-propenyl, 2-butenyl, 3-butenyl, 3-hexenyl, in particular ethenyl, 2-propenyl and 2-butenyl;

alkynyl, particularly $C_2$–$C_6$-alkynyl such as mentioned above, preferably ethynyl, 2-propynyl, 1-methyl-2-butynyl, 1,1-dimethyl-2-butynyl, in particular ethynyl and 1,1-dimethyl-2-butynyl;

$C_1$–$C_4$-haloalkyl such as mentioned above, preferably trichloromethyl, difluoromethyl, trifluoromethyl, 2,2-difluoroethyl, 2,2,2-trifluoroethyl and pentafluoroethyl;

$C_1$–$C_4$-alkoxy, preferably methoxy, ethoxy, 1-methylethoxy and 1,1-dimethylethoxy, in particular methoxy;

$C_1$–$C_4$-haloalkoxy, particularly $C_1$–$C_2$-haloalkoxy, preferably difluoromethoxy, trifluoromethoxy and 2,2,2-trifluoroethoxy, in particular difluoromethoxy;

$C_1$–$C_4$-alkylthio, preferably methylthio and 1-methylethylthio, in particular methylthio;

$C_1$–$C_4$-alkylamino such as methylamino, ethylamino, propylamino, 1-methylethylamino, butylamino, 1-methylpropylamino, 2-methylpropylamino and 1,1-dimethylethylamino, preferably methylamino and 1,1-dimethylethylamino, in particular methylamino;

di-$C_1$–$C_4$-alkylamino such as N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably N,N-dimethylamino and N,N-diethylamino, in particular N,N-dimethylamino;

$C_3$–$C_6$-alkenyloxy such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 3,3-dimethyl-2-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy and 1-ethyl-2-methyl-2-propenyloxy, preferably 2-propenyloxy and 3-methyl-2-butenyloxy, in particular 2-propenyloxy;

$C_3$–$C_6$-alkynyloxy such as 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl-3-butynyloxy, 2-methyl-3-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-1-methyl-2-propynyloxy, preferably 2-propynyloxy and 2-butynyloxy, in particular 2-propynyloxy;

$C_1$–$C_6$-alkylcarbonyl such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, preferably methylcarbonyl, ethylcarbonyl and 1,1-dimethylcarbonyl, in particular ethylcarbonyl;

$C_1$–$C_6$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl, pentyloxycarbonyl, 1-methylbutyloxycarbonyl, 2-methylbutyloxycarbonyl, 3-methylbutyloxycarbonyl, 2,2-dimethylpropyloxycarbonyl, 1-ethylpropyloxycarbonyl, hexyloxycarbonyl, 1,1-dimethylpropoxycarbonyl, 1,2-dimethylpropyloxycarbonyl, 1-methylpentyloxycarbonyl, 2-methylpentyloxycarbonyl, 3-methylpentyloxycarbonyl, 4-methylpentyloxycarbonyl, 1,1-dimethylbutyloxycarbonyl, 1,2-dimethylbutyloxycarbonyl, 1,3-dimethylbutyloxycarbonyl, 2,2-dimethylbutyloxycarbonyl, 2,3-dimethylbutyloxycarbonyl, 3,3-dimethylbutyloxycarbonyl, 1-ethylbutyloxycarbonyl, 2-ethylbutyloxycarbonyl, 1,1,2-trimethylpropyloxycarbonyl, 1,2,2-trimethylpropyloxycarbonyl, 1-ethyl-1-methylpropyloxycarbonyl and 1-ethyl-2-methylpropyloxycarbonyl, preferably methoxycarbonyl, ethoxycarbonyl and 1,1-dimethylethoxycarbonyl, in particular ethoxycarbonyl;

$C_1$–$C_6$-alkylthiocarbonyl such as methylthiocarbonyl, ethylthiocarbonyl, propylthiocarbonyl, 1-methylethylthiocarbonyl, butylthiocarbonyl, 1-methylpropylthiocarbonyl, 2-methylpropylthiocarbonyl, 1,1-dimethylethylthiocarbonyl, pentylthiocarbonyl, 1-methylbutylthiocarbonyl, 2-methylbutylthiocarbonyl, 3-methylbutylthiocarbonyl, 2,2-dimethylpropylthiocarbonyl, 1-ethylpropylthiocarbonyl, hexylthiocarbonyl, 1,1-dimethylpropthiocarbonyl [sic], 1,2-dimethylpropylthiocarbonyl, 1-methylpentylthiocarbonyl, 2-methylpentylthiocarbonyl, 3-methylpentylthiocarbonyl, 4-methylpentylthiocarbonyl, 1,1-dimethylbutylthiocarbonyl, 1,2-dimethylbutylthiocarbonyl, 1,3-dimethylbutylthiocarbonyl, 2,2-dimethylbutylthiocarbonyl, 2,3-dimethylbutylthiocarbonyl, 3,3-dimethylbutylthiocarbonyl, 1-ethylbutylthiocarbonyl, 2-ethylbutylthiocarbonyl, 1,1,2-trimethylpropylthiocarbonyl, 1,2,2-trimethylpropylthiocarbonyl, 1-ethyl-1-methylpropylthiocarbonyl and 1-ethyl-2-methylpropylthiocarbonyl, preferably methylthiocarbonyl and 1-methylethylthiocarbonyl, in particular methylthiocarbonyl;

$C_1$–$C_6$-alkylaminocarbonyl such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1,-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl and 1-ethyl-2-methylpropylaminocarbonyl, preferably methylaminecarbonyl [sic] and ethylaminecarbonyl [sic], in particular methylaminocarbonyl;

di-$C_1$–$C_6$-alkylaminocarbonyl, particularly di-$C_1$–$C_4$-alkylaminocarbonyl such as N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl and N-(1,1-dimethylethyl)-N-(2-methylpropyl)aminocarbonyl, preferably N,N-dimethylaminocarbonyl and N,N-diethylaminocarbonyl, in particular N,N-dimethylaminocarbonyl;

$C_1$–$C_6$-alkylcarboxyl such as methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl and 1-ethyl-2-methylpropylcarboxyl, preferably methylcarboxyl, ethylcarboxyl and 1,1-dimethylethylcarbonyl [sic], in particular methylcarboxyl and 1,1-dimethylethylcarboxyl;

$C_1$–$C_6$-alkylcarbonylamino such as methylcarbonylamino, ethylcarbonylamino, propylcarbonylamino, 1-methylethylcarbonylamino, butylcarbonylamino, 1-methylpropylcarbonylamino, 2-methylpropylcarbonylamino, 1,1-dimethylethylcarbonylamino, pentylcarbonylamino, 1-methylbutylcarbonylamino, 2-methylbutylcarbonylamino, 3-methylbutylcarbonylamino, 2,2-dimethylpropylcarbonylamino, 1-ethylpropylcarbonylamino, hexylcarbonylamino, 1,1-dimethylpropylcarbonylamino, 1,2-dimethylpropylcarbonylamino, 1-methylpentylcarbonylamino, 2-methylpentylcarbonylamino, 3-methylpentylcarbonylamino, 4-methylpentylcarbonylamino, 1,1-dimethylbutylcarbonylamino, 1,2-dimethylbutylcarbonylamino, 1,3- dimethylbutylcarbonylamino, 2,2-dimethylbutylcarbonylamino, 2,3-dimethylbutylcarbonylamino, 3,3-dimethylbutylcarbonylamino, 1-ethylbutylcarbonylamino, 2-ethylbutylcarbonylamino, 1,1,2-trimethylpropylcarbonylamino, 1,2,2-trimethylpropylcarbonylamino, 1-ethyl-1-methylpropylcarbonylamino and 1-ethyl-2-methylpropylcarbonylamino, preferably methylcarbonylamino and ethylcarbonylamino, in particular ethylcarbonylamino;

$C_3$–$C_7$-cycloalkyl such as cyclopropyl, cyclobutyl, cyclopentyl, cyclohexyl and cycloheptyl, preferably cyclopropyl, cyclopentyl and cyclohexyl, in particular cyclopropyl;

$C_3$–$C_7$-cycloalkoxy such as cyclopropyloxy, cyclobutyloxy, cyclopentyloxy, cyclohexyloxy and cycloheptyloxy, preferably cyclopentyloxy and cyclohexyloxy, in particular cyclohexyloxy;

$C_3$–$C_7$-cycloalkylthio such as cyclopropylthio, cyclobutylthio, cyclopentylthio, cyclohexylthio and cycloheptylthio, preferably cyclohexylthio;

$C_3$–$C_7$-cycloalkylamino such as cyclopropylamino, cyclobutylamino, cyclopentylamino, cyclohexylamino and cycloheptylamino, preferably cyclopropylamino and cyclohexylamino, in particular cyclopropylamino;

$C_5$–$C_7$-cycloalkenyl such as cyclopenten-1-yl, cyclopenten-2-yl, cyclopenten-3-yl, cyclohexen-1-yl, cyclohexen-2-yl, cyclohexen-3-yl, cyclohepten-1-yl, cyclohepten-2-yl, cyclohepten-3-yl and cyclohepten-4-yl, preferably cyclopenten-1-yl, cyclopenten-3-yl and cyclohexen-2-yl, in particular cyclopenten-1-yl;

5- to 6-membered, saturated or unsaturated heterocycles containing one to three nitrogen atoms and/or an oxygen or sulfur atom such as mentioned above, preferably tetrahydropyrazin-1-yl and 2-tetrahydrofuranyl, tetrahydropyran-4-yl and 1,3-dioxan-2-yl;

phenyl;

5-membered ring heteroaromatics containing one to three nitrogen atoms and/or an oxygen or sulfur atom such as mentioned above, preferably 3-furyl, 3-thienyl, 5-isoxazolyl, 3-isoxazolyl, 4-oxazolyl, 1,3,4-thiadiazol-3-yl and 2-thienyl, it being possible for a benzene ring to be fused to the abovementioned 5-membered heteroaromatic;

6-membered ring heteroaromatics containing one to three nitrogen atoms as hetero atoms, preferably 5-pyrimidyl and 3-pyridinyl, it being possible for the abovementioned aryl and heteroaryl rings to carry one to three of the following groups: fluorine, chlorine, cyano, methyl, methoxy, trifluoromethyl and trifluoromethoxy.

Two adjacent radicals $R^2$ can have the meaning of an oxy-$C_1$–$C_2$-alkylidenoxy chain which is unsubstituted or substituted by flurine [sic], such as eg. —O—CH$_2$—O—, —O—CF$_2$—O—, —O—CH$_2$CH$_2$—O— or —O—CF$_2$CF$_2$—O—, or of a $C_3$–$C_4$-alkylidene chain, such as eg. propylidene or butylidene.

The alkyl, alkenyl and alkynyl groups mentioned under the radical $R^2$ can for their part be partially or completely halogenated, ie. the hydrogen atoms of these groups can be partially or completely replaced by halogen atoms such as fluorine, chlorine, bromine and iodine, preferably fluorine and chlorine.

In addition to the designated halogen atoms, the said alkyl, alkenyl and alkynyl groups can additionally carry one to three of the following substituents:

nitro;

cyano; thicyanato [sic];

$C_1$–$C_4$-alkoxy, preferably methoxy, ethoxy and 1-methylethoxy, in particular methoxy;

$C_1$–$C_4$-haloalkoxy, particularly $C_1$–$C_2$-haloalkoxy, in particular difluoromethoxy;

$C_1$–$C_4$-alkylthio, preferably methylthio and 1,1-dimethylethylthio, in particular methylthio;

$C_1$–$C_4$-alkylamino;

di-$C_1$–$C_4$-alkylamino;

$C_3$–$C_6$-alkenyloxy, in particular 2-propenyloxy;

$C_3$–$C_6$-alkynyloxy, in particular 2-propynyloxy;

$C_1$–$C_6$-alkylcarbonyl;

$C_1$–$C_6$-alkoxyimino (alkyl-O—N=) such as methoxyimino, ethoxyimino, propyloxyimino, 1-methylethoxyimino, butyloxyimino, 1-methylpropyloxyimino, 2-methylpropyloxyimino, 1,1-dimethylethoxyimino, pentyloxyimino, 1-methylbutyloxyimino, 2-methylbutyloxyimino, 3-methylbutyloxyimino, 2,2-dimethylpropyloxyimino, 1-ethylpropyloxyimino, hexyloxyimino, 1,1-dimethylpropoxyimino, 1,2-dimethylpropyloxyimino, 1-methylpentyloxyimino, 2-methylpentyloxyimino, 3-methylpentyloxyimino, 4-methylpentyloxyimino, 1,1-dimethylbutyloxyimino, 1,2-dimethylbutyloxyimino, 1,3-dimethylbutyloxyimino, 2,2-dimethylbutyloxyimino, 2,3-dimethylbutyloxyimino, 3,3-dimethylbutyloxyimino, 1-ethylbutyloxyimino, 2-ethylbutyloxyimino, 1,1,2-trimethylpropyloxyimino, 1,2,2-trimethylpropyloxyimino, 1-ethyl-1-methylpropyloxyimino and 1-ethyl-2-methylpropyloxyimino, preferably methoxyimino, ethoxyimino, propyloximino, 1,1-dimethylethyloximino and 1-methylethyloximino, in particular methyloximino and ethyloximino;

$C_3$–$C_6$-alkenyloxyimino, ie. $C_3$–$C_6$-alkenyloxy such as mentioned above, which is bonded to the structure via —N= (imino);

$C_3$–$C_6$-alkynyloxyimino, ie. $C_3$–$C_6$-alkynyloxy such as mentioned above, which is bonded to the structure via —N= (imino);

$C_1$–$C_6$-alkoxycarbonyl, in particular methoxycarbonyl, ethoxycarbonyl and 1,1-dimethylethoxycarbonyl, in particular methoxycarbonyl and 1,1-dimethylethoxycarbonyl;

$C_1$–$C_6$-alkylthiocarbonyl, in particular methylthiocarbonyl;

$C_1$–$C_6$-alkylaminocarbonyl, in particular methyliminocarbonyl;

di-$C_1$–$C_6$-alkylaminocarbonyl, in particular N,N-dimethylaminocarbonyl;

$C_1$–$C_6$-alkylcarboxyl, preferably methylcarboxyl and 1,1-dimethylethylcarboxyl, in particular methylcarboxyl;

$C_1$–$C_6$-alkylcarbonylamino, preferably methylcarbonylamino and 1,1-dimethylethylcarbonylamino, in particular methylcarbonylamino;

$C_3$–$C_7$-cycloalkyl, preferably cyclopropyl, cyclopentyl and cyclohexyl, in particular cyclopropyl;

$C_3$–$C_7$-cycloalkoxy, in particular cyclohexyloxy;

$C_3$–$C_7$-cycloalkylthio, in particular cyclohexylthio;

$C_3$–$C_7$-cycloalkylamino;

$C_5$–$C_7$-cycloalkenyl, preferably cyclopent-1-enyl, cyclopent-2-enyl and cyclohex-2-enyl, in particular cyclopent-1-entyl [sic];

5- to 6-membered, saturated or unsaturated heterocycles containing one to three nitrogen atoms and/or an oxygen or sulfur atom, such as mentioned above, preferably tetrahydropyran-4-yl, 2-tetrahydrofuranyl and 1,3-dioxan-2-yl;

aromatic systems such as phenyl, 1-naphthyl and 2-naphthyl;

5-membered ring heteroaromatics containing one to three nitrogen atoms and/or an oxygen or sulfur atom, such as mentioned above, preferably 2-furyl, 3-furyl, 2-thienyl, 3-thienyl, 5-isoxazolyl and 4-oxazolyl, in particular 2-furyl and 2-thienyl, it being possible for a benzene ring to be fused to the abovementioned 5-membered heteroaromatics;

6-membered ring heteroaromatics containing one to three nitrogen atoms as hetero atoms such as preferably 2-pyrimidinyl, 5-pyrimidinyl and 3-pyridyl, it being possible for a benzene ring to be fused to the abovementioned 6-membered heteroaromatics.

The saturated or mono- or diunsaturated alicyclic or heterocyclic systems mentioned under the radical $R^2$ can for their part be partially or completely halogenated, ie. the hydrogen atoms of these groups can be replaced partially or completely by halogen atoms such as fluorine, chlorine, bromine and iodine, preferably fluorine and chlorine.

In addition to the designated halogen atoms, these mono- or diunsaturated alicyclic or heterocyclic systems can additionally carry one to three of the following substituents:

nitro;

cyano;

$C_1$–$C_6$-alkyl, preferably methyl and ethyl, in particular methyl;

$C_1$–$C_4$-haloalkyl, particularly $C_1$–$C_2$-haloalkyl, in particular trifluoromethyl;

$C_1$–$C_4$-alkoxy, in particular methoxy;

$C_1$–$C_4$-alkylthio;

di-$C_1$–$C_4$-alkylamino;

$C_2$–$C_6$-alkenyl, preferably ethenyl, 1-propenyl, 2-propenyl and 1-methylethynyl [sic], in particular ethenyl and 1-methylethenyl;

$C_2$–$C_6$-alkynyl, preferably ethynyl, 2-propynyl, 1-butynyl, in particular ethynyl;

$C_1$–$C_6$-alkoxycarbonyl, preferably methoxycarbonyl, ethoxycarbonyl, 1-methylethoxycarbonyl and 1,1-dimethylethoxycarbonyl, in particular ethoxycarbonyl;

$C_1$–$C_6$-alkylaminocarbonyl;

di-$C_1$–$C_6$-alkylaminocarbonyl;

$C_1$–$C_6$-alkylcarboxyl, in particular methylcarboxyl;

$C_1$–$C_6$-alkylcarbonylamino, in particular methylcarbonylamino and 1,1-dimethylcarbonylamino;

$C_3$–$C_7$-cycloalkyl, preferably cyclopropyl and cyclohexyl, in particular cyclopropyl;

aromatic systems such as, in particular, phenyl.

In addition, compounds I are preferred in which $R^1$ is halogen, $C_1$–$C_4$-alkyl, $C_1$–$C_2$-haloalkyl, $C_1$–$C_4$-alkoxy, $C_1$–$C_2$-haloalkoxy or phenyl.

Those compounds I are additionally preferred in which X is oxygen.

Of particular interest are those compounds I in which Y is 3-isoxazolyl, 1-pyrazolyl, 3-pyrazolyl, 4-pyrazolyl, 2-oxazolyl, 2-thiazolyl, 4-thiazolyl, 1,2,4-triazol-3-yl, 1,3,4-oxadiazol-2-yl, 1,2,4-oxadiazol-5-yl and 1,2,4-thiadiazol-5-yl, in particular 3-pyrazolyl, 4-thiazolyl and 1,2,4-triazol-3-yl.

Those compounds I are particularly preferred in which $R^2$ is unsubstituted or substituted phenyl. Suitable substituents of the phenyl radical are preferably halogen, cyano, $C_1$–$C_4$-alkyl, $C_1$–$C_4$-alkoxy, $C_1$–$C_2$-haloalkyl, $C_1$–$C_2$-haloalkoxy, phenyl and oxy-$C_1$–$C_2$-alkylidenoxy.

Likewise preferred are those compounds I in which $R^2$ is unsubstituted or substituted five-membered ring heteroaromatics such as eg. thiazolyl, isoxazolyl, oxazolyl or 1,2,4-oxadiazolyl. Suitable substituents of the five-membered ring heteroaromatics are preferably halogen, cyano, $C_1$–$C_6$-alkyl, $C_1$–$C_6$-alkoxy, $C_1$–$C_4$-haloalkyl, $C_1$–$C_2$-haloalkoxy and phenyl.

Likewise preferred are those compounds I in which $R^2$ is unsubstituted or substituted six-membered ring heteroaromatics, such as eg. pyridyl, pyrimidyl, pyridazinyl or pyrazinyl. Suitable substituents of the six-membered ring heteroaromatics are preferably halogen, cyano, $C_1$–$C_4$-alkyl, $C_1$–$C_4$-alkoxy, $C_1$–$C_2$-haloalkyl, $C_1$–$C_2$-haloalkoxy and phenyl.

Likewise preferred are those compounds I in which $R^2$ is $C_1$–$C_6$-alkoxyimino-, $C_3$–$C_6$-alkenyloxyimino- or $C_3$–$C_6$-alkynyloxyimino-substituted alkyl, such as eg. methoxyiminoethyl, ethoxyiminoethyl, propoxyiminoethyl, i-propoxyiminoethyl, (2-propen)oxyiminoethyl, (2-butene)oxyiminoethyl, (2-propyn)oxyiminoethyl, methoxyiminopropyl, ethoxyiminopropyl, propoxyiminopropyl, (2-propen)oxyiminopropyl or (2-propyn)oxyiminopropyl.

Compounds of the general formula I are additionally preferred in which

Y is a five-membered ring heteroaromatic system which, in addition to $R^2$, can also carry one or two radicals from the group consisting of Cl, $CH_3$, $CF_3$ and $OCH_3$;

$R^1$ is halogen, $C_1$–$C_4$-alkyl, $C_1$–$C_2$-haloalkyl, $C_1$–$C_2$-alkoxy, $C_1$–$C_2$-haloalkoxy, $C_1$–$C_2$-alkylthio or phenyl;

n is 0 or 1;

X is O or S;

$R^2$ is unsubstituted or substituted $C_1$–$C_4$-alkyl or unsubstituted or substituted $C_3$–$C_6$-cycloalkyl.

In addition, compounds of the general formula I are preferred in which $R^2$—Y— is one of the following five-membered ring heteroaromatic systems

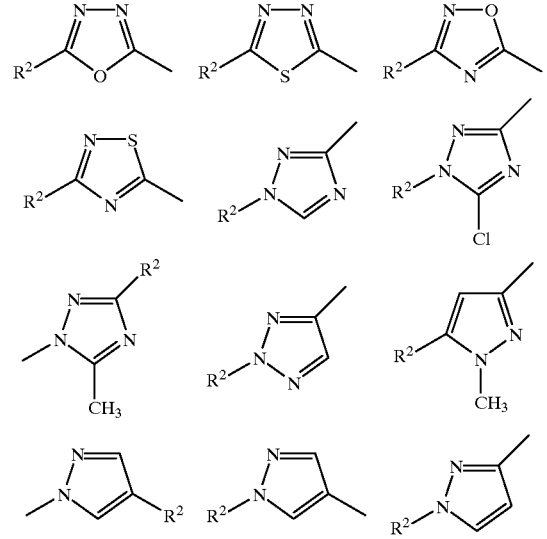

-continued

[Chemical structures of various heteroaromatic rings with R² substituents, including pyrazoles, thiazoles, oxazoles, isoxazoles, and thiophene]

In addition, compounds of the general formula I are preferred in which
  n is 0 or 1;
  X is O or S;
  Y is a five-membered ring heteroaromatic system which, in addition to R², can also carry one or two radicals from the group consisting of Cl, CH₃, CF₃ and OCH₃;
  $R^1$ is halogen, $C_1$–$C_4$-alkyl, $C_1$–$C_2$-haloalkyl, $C_1$–$C_4$-alkoxy, $C_1$–$C_2$-haloalkoxy, $C_1$–$C_2$-alkylthio or phenyl;
  $R^2$ is an unsubstituted or substituted, mono- or binuclear aromatic ring system which, in addition to carbon atoms, can contain one to four nitrogen atoms or one or two nitrogen atoms and an oxygen or sulfur atom or an oxygen or sulfur atom as ring members.

Additionally, compounds of the general formula I are preferred in which
  n is 0;
  X is O;
  Y is a five-membered ring heteroaromatic system which, in addition to R², can also carry one or two radicals from the group consisting of Cl, CH₃, CF₃ and OCH₃;
  $R^2$ is an unsubstituted or substituted, mono- or binuclear aromatic ring system which, in addition to carbon atoms, can contain one to four nitrogen atoms or one or two nitrogen atoms and an oxygen or sulfur atom or an oxygen or sulfur atom as ring members.

In addition, compounds of the general formula I are preferred in which
  n is 0 or 1;
  X is O or S;
  Y is a five-membered ring heteroaromatic system which, in addition to R², can also carry one or two radicals from the group consisting of Cl, CH₃, CF₃ and OCH₃;
  $R^1$ is halogen, $C_1$–$C_4$-alkyl, $C_1$–$C_2$-haloalkyl, $C_1$–$C_4$-alkoxy, $C_1$–$C_2$-haloalkoxy, $C_1$–$C_2$-alkylthio or phenyl;
  $R^2$ is unsubstituted or substituted phenyl.

In addition, compounds of the general formula I are preferred in which
  n is 0;
  X is O;
  Y is a five-membered ring heteroaromatic system which, in addition to R², can also carry one or two radicals from the group consisting of Cl, CH₃, CF₃ and OCH₃;
  $R^2$ is unsubstituted or substituted phenyl.

Compounds of the general formula I are further preferred in which
  n is 0 or 1;
  X is O or S;
  Y is a five-membered ring heteroaromatic system which, in addition to R², can also carry one or two radicals from the group consisting of Cl, CH₃, CF₃ or OCH₃;
  $R^1$ is halogen, $C_1$–$C_4$-alkyl, $C_1$–$C_2$-haloalkyl, $C_1$–$C_4$-alkoxy, $C_1$–$C_2$-haloalkoxy, $C_1$–$C_2$-alkylthio or phenyl;
  $R^2$ is unsubstituted or substituted five-membered ring heteroaromatics.

Compounds of the general formula I are additionally preferred in which
  n is 0 or 1;
  X is O or S;
  Y is a six-membered ring heteroaromatic system which, in addition to R², can also carry one or two radicals from the group consisting of Cl, CH₃, CF₃ and OCH₃;
  $R^2$ is unsubstituted or substituted six-membered ring heteroaromatics.

Particularly preferred compounds of the formula I.1, I.2, I.3, I.4, I.5, I.6, I.7, I.8, I.9, I.10, I.11 and I.12 are summarized in the Tables A.1, A.2, A.3, A.4, A.5, A.6, A.7, A.8, A.9, A.10, A.11 and A.12 below.

TABLES

TABLE A.1

[Chemical structure labeled I.1]

| No. | R¹ₙ | R² |
|---|---|---|
| 1.001 | H | $C_6H_5$ |
| 1.002 | 3-Cl | $C_6H_5$ |
| 1.003 | 4-Cl | $C_6H_5$ |
| 1.004 | 6-Cl | $C_6H_5$ |
| 1.005 | 4-F | $C_6H_5$ |
| 1.006 | 4-$OCH_3$ | $C_6H_5$ |
| 1.007 | 3-$CH_3$ | $C_6H_5$ |
| 1.008 | 6-$CH_3$ | $C_6H_5$ |
| 1.009 | H | 2-F—$C_6H_4$ |
| 1.010 | H | 3-F—$C_6H_4$ |
| 1.011 | H | 4-F—$C_6H_4$ |
| 1.012 | H | 2,3-$F_2$—$C_6H_3$ |
| 1.013 | H | 2,4-$F_2$—$C_6H_3$ |
| 1.014 | H | 2,5-$F_2$—$C_6H_3$ |
| 1.015 | H | 2,6-$F_2$—$C_6H_3$ |
| 1.016 | H | 3,4-$F_2$—$C_6H_3$ |
| 1.017 | H | 3,5-$F_2$—$C_6H_3$ |
| 1.018 | H | 2-Cl—$C_6H_4$ |
| 1.019 | H | 3-Cl—$C_6H_4$ |
| 1.020 | H | 4-Cl—$C_6H_4$ |
| 1.021 | 3-Cl | 4-Cl—$C_6H_4$ |
| 1.022 | 4-Cl | 4-Cl—$C_6H_4$ |
| 1.023 | 6-Cl | 4-Cl—$C_6H_4$ |
| 1.024 | 4-F | 4-Cl—$C_6H_4$ |
| 1.025 | 4-$OCH_3$ | 4-Cl—$C_6H_4$ |
| 1.026 | 3-$CH_3$ | 4-Cl—$C_6H_4$ |
| 1.027 | 6-$CH_3$ | 4-Cl—$C_6H_4$ |
| 1.028 | H | 2,3-$Cl_2$—$C_6H_3$ |
| 1.029 | H | 2,4-$Cl_2$—$C_6H_3$ |
| 1.030 | H | 2,5-$Cl_2$—$C_6H_3$ |
| 1.031 | H | 2,6-$Cl_2$—$C_6H_3$ |
| 1.032 | H | 3,4-$Cl_2$—$C_6H_3$ |
| 1.033 | H | 3,5-$Cl_2$—$C_6H_3$ |
| 1.034 | H | 2,3,4-$Cl_3$—$C_6H_2$ |
| 1.035 | H | 2,3,5-$Cl_3$—$C_6H_2$ |
| 1.036 | H | 2,3,6-$Cl_3$—$C_6H_2$ |
| 1.037 | H | 2,4,5-$Cl_3$—$C_6H_2$ |
| 1.038 | H | 2,4,6-$Cl_3$—$C_6H_2$ |
| 1.039 | H | 3,4,5-$Cl_3$—$C_6H_2$ |
| 1.040 | H | 2-Br—$C_6H_4$ |
| 1.041 | H | 3-Br—$C_6H_4$ |
| 1.042 | H | 4-Br—$C_6H_4$ |
| 1.043 | H | 2,4-$Br_2$—$C_6H_3$ |
| 1.044 | H | 2-Br, 4-F—$C_6H_3$ |
| 1.045 | H | 2-Br, 4-Cl—$C_6H_3$ |
| 1.046 | H | 2-F, 4-Cl—$C_6H_3$ |
| 1.047 | H | 3-F, 4-Cl—$C_6H_3$ |
| 1.048 | H | 3-Cl, 5-F—$C_6H_3$ |
| 1.049 | H | 2-Cl, 4-F—$C_6H_3$ |
| 1.050 | H | 2-CN—$C_6H_4$ |
| 1.051 | H | 3-CN—$C_6H_4$ |
| 1.052 | H | 4-CN—$C_6H_4$ |
| 1.053 | H | 3-CN, 4-Cl—$C_6H_3$ |
| 1.054 | H | 4-$NO_2$—$C_6H_4$ |
| 1.055 | H | 4-$H_2$N—C(=S)—$C_6H_4$ |
| 1.056 | H | 2-$CH_3$—$C_6H_4$ |
| 1.057 | H | 3-$CH_3$—$C_6H_4$ |
| 1.058 | H | 4-$CH_3$—$C_6H_4$ |
| 1.059 | H | 2,4-$(CH_3)_2$—$C_6H_3$ |
| 1.060 | H | 2,5-$(CH_3)_2$—$C_6H_3$ |
| 1.061 | H | 2,5-$(CH_3)_2$—$C_6H_3$ |
| 1.062 | H | 2,6-$(CH_3)_2$—$C_6H_3$ |
| 1.063 | H | 3,4-$(CH_3)_2$—$C_6H_3$ |
| 1.064 | H | 3,5-$(CH_3)_2$—$C_6H_3$ |
| 1.065 | H | 2,4,6-$(CH_3)_3$—$C_6H_2$ |
| 1.066 | H | 3,4,5-$(CH_3)_3$—$C_6H_2$ |
| 1.067 | H | 2-$CH_3$, 4-Cl—$C_6H_3$ |
| 1.068 | H | 2-Cl, 4-$CH_3$—$C_6H_3$ |
| 1.069 | H | 3-$CH_3$, 4-Cl—$C_6H_3$ |
| 1.070 | H | 3-Cl, 5-$CH_3$—$C_6H_3$ |
| 1.071 | H | 2-CN, 4-$CH_3$—$C_6H_3$ |
| 1.072 | H | 2-$CH_3$, 4-CN—$C_6H_3$ |
| 1.073 | H | 4-$(C_2H_5)$—$C_6H_4$ |
| 1.074 | H | 4-$[C(CH_3)_3]$—$C_6H_4$ |
| 1.075 | H | 3-$(C_6H_5)$—$C_6H_4$ |
| 1.076 | H | 4-$(C_6H_5)$—$C_6H_4$ |
| 1.077 | H | 2-$CF_3$—$C_6H_4$ |
| 1.078 | H | 3-$CF_3$—$C_6H_4$ |
| 1.079 | H | 4-$CF_3$—$C_6H_4$ |
| 1.080 | H | 3,5-$(CF_3)_2$—$C_6H_3$ |
| 1.081 | H | 2-Cl, 4-$CF_3$—$C_6H_3$ |
| 1.082 | H | 2-$OCH_3$—$C_6H_4$ |
| 1.083 | H | 3-$OCH_3$—$C_6H_4$ |
| 1.084 | H | 4-$OCH_3$—$C_6H_4$ |
| 1.085 | H | 2,4-$(OCH_3)_2$—$C_6H_3$ |
| 1.086 | H | 3,4-$(OCH_3)_2$—$C_6H_3$ |
| 1.087 | H | 2,5-$(OCH_3)_2$—$C_6H_3$ |
| 1.088 | H | 3,5-$(OCH_3)_2$—$C_6H_3$ |
| 1.089 | H | 3,4,5-$(OCH_3)_3$—$C_6H_2$ |
| 1.090 | H | 2-$CH_3$, 4-$OCH_3$—$C_6H_3$ |
| 1.091 | H | 2-Cl, 4-$OCH_3$—$C_6H_3$ |
| 1.092 | H | 4-$OCF_3$—$C_6H_4$ |
| 1.093 | H | 2-$OCHF_2$—$C_6H_4$ |
| 1.094 | H | 3-$OCHF_2$—$C_6H_4$ |
| 1.095 | H | 4-$OCHF_2$—$C_6H_4$ |
| 1.096 | H | 4-$(OCF_2CHF_2)$—$C_6H_4$ |
| 1.097 | H | 2-F, 4-$OCHF_2$—$C_6H_3$ |
| 1.098 | H | 4-$(OCH_2CH_3)$—$C_6H_4$ |
| 1.099 | H | 4-$[OC(CH_3)_3]$—$C_6H_4$ |
| 1.100 | H | 3-$(CO_2CH_3)$—$C_6H_4$ |
| 1.101 | H | 4-$(CO_2CH_3)$—$C_6H_4$ |
| 1.102 | H | 4-$[CO_2C(CH_3)_3]$—$C_6H_4$ |
| 1.103 | H | 2,3-$[O—CH_2—O)$—$C_6H_3$ |
| 1.104 | H | 3,4-$[O—CH_2—O)$—$C_6H_3$ |
| 1.105 | H | 3,4-$[O—C(CH_3)_2—O]$—$C_6H_3$ |
| 1.106 | H | 3,4-$[O—CH_2CH_2—O]$—$C_6H_3$ |
| 1.107 | H | 2,3-$[(CH_2)_4]$—$C_6H_3$ |
| 1.108 | H | 3,4-$[(CH_2)_4]$—$C_6H_3$ |
| 1.109 | H | 2,3-(CH=$CH_2$—CH=CH)—$C_6H_3$ |
| 1.110 | H | 3,4-(CH=CH—CH=CH)—$C_6H_3$ |
| 1.111 | H | $CH_3$ |
| 1.112 | H | $CH_2CH_3$ |
| 1.113 | H | $CH_2CH_2CH_3$ |
| 1.114 | H | $C(CH_3)_2$ |
| 1.115 | H | $CH_2CH_2CH_2CH_3$ |
| 1.116 | H | $CHCH(CH_3)_2$ |
| 1.117 | H | $CH(CH_3)CH_2CH_3$ |
| 1.118 | H | $C(CH_3)_3$ |
| 1.119 | H | cyclopropyl |
| 1.120 | H | cyclohexyl |
| 1.121 | H | 2-tetrahydrofuranyl |
| 1.122 | H | 3-tetrahydrofuranyl |
| 1.123 | H | 3-tetrahydrothienyl |
| 1.124 | H | 2-1,3-dioxolenyl [sic] |
| 1.125 | H | 2-1,3-dioxanyl |
| 1.126 | H | 4-tetrahydropyranyl |

TABLE A.2

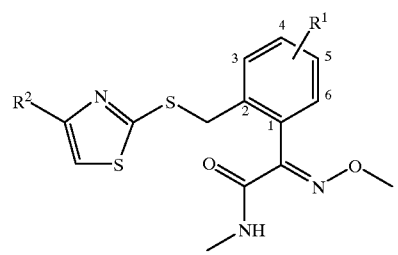

I.2

| No. | R¹ₙ | R² |
|---|---|---|
| 2.001 | H | $C_6H_5$ |
| 2.002 | 3-Cl | $C_6H_5$ |
| 2.003 | 4-Cl | $C_6H_5$ |
| 2.004 | 6-Cl | $C_6H_5$ |
| 2.005 | 4-F | $C_6H_5$ |
| 2.006 | 4-$OCH_3$ | $C_6H_5$ |
| 2.007 | 3-$CH_3$ | $C_6H_5$ |
| 2.008 | 6-$CH_3$ | $C_6H_5$ |
| 2.009 | H | 2-F—$C_6H_4$ |
| 2.010 | H | 3-F—$C_6H_4$ |
| 2.011 | H | 4-F—$C_6H_4$ |
| 2.012 | H | 2,3-$F_2$—$C_6H_3$ |

| No. | | |
|---|---|---|
| 2.013 | H | 2,4-F$_2$—C$_6$H$_3$ |
| 2.014 | H | 2,5-F$_2$—C$_6$H$_3$ |
| 2.015 | H | 2,6-F$_2$—C$_6$H$_3$ |
| 2.016 | H | 3,4-F$_2$—C$_6$H$_3$ |
| 2.017 | H | 3,5-F$_2$—C$_6$H$_3$ |
| 2.018 | H | 2-Cl—C$_6$H$_4$ |
| 2.019 | H | 3-Cl—C$_6$H$_4$ |
| 2.020 | H | 4-Cl—C$_6$H$_4$ |
| 2.021 | 3-Cl | 4-Cl—C$_6$H$_4$ |
| 2.022 | 4-Cl | 4-Cl—C$_6$H$_4$ |
| 2.023 | 6-Cl | 4-Cl—C$_6$H$_4$ |
| 2.024 | 4-F | 4-Cl—C$_6$H$_4$ |
| 2.025 | 4-OCH$_3$ | 4-Cl—C$_6$H$_4$ |
| 2.026 | 3-CH$_3$ | 4-Cl—C$_6$H$_4$ |
| 2.027 | 6-CH$_3$ | 4-Cl—C$_6$H$_4$ |
| 2.028 | H | 2,3-Cl$_2$—C$_6$H$_3$ |
| 2.029 | H | 2,4-Cl$_2$—C$_6$H$_3$ |
| 2.030 | H | 2,5-Cl$_2$—C$_6$H$_3$ |
| 2.031 | H | 2,6-Cl$_2$—C$_6$H$_3$ |
| 2.032 | H | 3,4-Cl$_2$—C$_6$H$_3$ |
| 2.033 | H | 3,5-Cl$_2$—C$_6$H$_3$ |
| 2.034 | H | 2,3,4-Cl$_3$—C$_6$H$_2$ |
| 2.035 | H | 2,3,5-Cl$_3$—C$_6$H$_2$ |
| 2.036 | H | 2,3,6-Cl$_3$—C$_6$H$_2$ |
| 2.037 | H | 2,4,5-Cl$_3$—C$_6$H$_2$ |
| 2.038 | H | 2,4,6-Cl$_3$—C$_6$H$_2$ |
| 2.039 | H | 3,4,5-Cl$_3$—C$_6$H$_2$ |
| 2.040 | H | 2-Br—C$_6$H$_4$ |
| 2.041 | H | 3-Br—C$_6$H$_4$ |
| 2.042 | H | 4-Br—C$_6$H$_4$ |
| 2.043 | H | 2,4-Br$_2$—C$_6$H$_3$ |
| 2.044 | H | 2-Br, 4-F—C$_6$H$_3$ |
| 2.045 | H | 2-Br, 4-Cl—C$_6$H$_3$ |
| 2.046 | H | 2-F, 4-Cl—C$_6$H$_3$ |
| 2.047 | H | 3-F, 4-Cl—C$_6$H$_3$ |
| 2.048 | H | 3-Cl, 5-F—C$_6$H$_3$ |
| 2.049 | H | 2-Cl, 4-F—C$_6$H$_3$ |
| 2.050 | H | 2-CN—C$_6$H$_4$ |
| 2.051 | H | 3-CN—C$_6$H$_4$ |
| 2.052 | H | 4-CN—C$_6$H$_4$ |
| 2.053 | H | 3-CN, 4-Cl—C$_6$H$_3$ |
| 2.054 | H | 4-NO$_2$—C$_6$H$_4$ |
| 2.055 | H | 4-H$_2$N—C(=S)—C$_6$H$_4$ |
| 2.056 | H | 2-CH$_3$—C$_6$H$_4$ |
| 2.057 | H | 3-CH$_3$—C$_6$H$_4$ |
| 2.058 | H | 4-CH$_3$—C$_6$H$_4$ |
| 2.059 | H | 2,4-(CH$_3$)$_2$—C$_6$H$_3$ |
| 2.060 | H | 2,5-(CH$_3$)$_2$—C$_6$H$_3$ |
| 2.061 | H | 2,5-(CH$_3$)$_2$—C$_6$H$_3$ |
| 2.062 | H | 2,6-(CH$_3$)$_2$—C$_6$H$_3$ |
| 2.063 | H | 3,4-(CH$_3$)$_2$—C$_6$H$_3$ |
| 2.064 | H | 3,5-(CH$_3$)$_2$—C$_6$H$_3$ |
| 2.065 | H | 2,4,6-(CH$_3$)$_3$—C$_6$H$_2$ |
| 2.066 | H | 3,4,5-(CH$_3$)$_3$—C$_6$H$_2$ |
| 2.067 | H | 2-CH$_3$, 4-Cl—C$_6$H$_3$ |
| 2.068 | H | 2-Cl, 4-CH$_3$—C$_6$H$_3$ |
| 2.069 | H | 3-CH$_3$, 4-Cl—C$_6$H$_3$ |
| 2.070 | H | 3-Cl, 5-CH$_3$—C$_6$H$_3$ |
| 2.071 | H | 2-CN, 4-CH$_3$—C$_6$H$_3$ |
| 2.072 | H | 2-CH$_3$, 4-CN—C$_6$H$_3$ |
| 2.073 | H | 4-(C$_2$H$_5$)—C$_6$H$_4$ |
| 2.074 | H | 4-[C(CH$_3$)$_3$]—C$_6$H$_4$ |
| 2.075 | H | 3-(C$_6$H$_5$)—C$_6$H$_4$ |
| 2.076 | H | 4-(C$_6$H$_5$)—C$_6$H$_4$ |
| 2.077 | H | 2-CF$_3$—C$_6$H$_4$ |
| 2.078 | H | 3-CF$_3$—C$_6$H$_4$ |
| 2.079 | H | 4-CF$_3$—C$_6$H$_4$ |
| 2.080 | H | 3,5-(CF$_3$)$_2$—C$_6$H$_3$ |
| 2.081 | H | 2-Cl, 4-CF$_3$—C$_6$H$_3$ |
| 2.082 | H | 2-OCH$_3$—C$_6$H$_4$ |
| 2.083 | H | 3-OCH$_3$—C$_6$H$_4$ |
| 2.084 | H | 4-OCH$_3$—C$_6$H$_4$ |
| 2.085 | H | 2,4-(OCH$_3$)$_2$—C$_6$H$_3$ |
| 2.086 | H | 3,4-(OCH$_3$)$_2$—C$_6$H$_3$ |
| 2.087 | H | 2,5-(OCH$_3$)$_2$—C$_6$H$_3$ |
| 2.088 | H | 3,5-(OCH$_3$)$_2$—C$_6$H$_3$ |
| 2.089 | H | 3,4,5-(OCH$_3$)$_3$—C$_6$H$_2$ |
| 2.090 | H | 2-CH$_3$, 4-OCH$_3$—C$_6$H$_3$ |
| 2.091 | H | 2-Cl, 4-OCH$_3$—C$_6$H$_3$ |
| 2.092 | H | 4-OCF$_3$—C$_6$H$_4$ |
| 2.093 | H | 2-OCHF$_2$—C$_6$H$_4$ |
| 2.094 | H | 3-OCHF$_2$—C$_6$H$_4$ |
| 2.095 | H | 4-OCHF$_2$—C$_6$H$_4$ |
| 2.096 | H | 4-(OCF$_2$CHF$_2$)—C$_6$H$_4$ |
| 2.097 | H | 2-F, 4-OCHF$_2$—C$_6$H$_3$ |
| 2.098 | H | 4-(OCH$_2$CH$_3$)—C$_6$H$_4$ |
| 2.099 | H | 4-[OC(CH$_3$)$_3$]—C$_6$H$_4$ |
| 2.100 | H | 3-(CO$_2$CH$_3$)—C$_6$H$_4$ |
| 2.101 | H | 4-(CO$_2$CH$_3$)—C$_6$H$_4$ |
| 2.102 | H | 4-[CO$_2$C(CH$_3$)$_3$]—C$_6$H$_4$ |
| 2.103 | H | 2,3-[O—CH$_2$—O]—C$_6$H$_3$ |
| 2.104 | H | 3,4-[O—CH$_2$—O]—C$_6$H$_3$ |
| 2.105 | H | 3,4-[O—C(CH$_3$)$_2$—O]—C$_6$H$_3$ |
| 2.106 | H | 3,4-[O—CH$_2$CH$_2$—O]—C$_6$H$_3$ |
| 2.107 | H | 2,3-[(CH$_2$)$_4$]—C$_6$H$_3$ |
| 2.108 | H | 3,4-[(CH$_2$)$_4$]—C$_6$H$_3$ |
| 2.109 | H | 2,3-(CH=CH$_2$—CH=CH)—C$_6$H$_3$ |
| 2.110 | H | 3,4-(CH=CH—CH=CH)—C$_6$H$_3$ |
| 2.111 | H | CH$_3$ |
| 2.112 | H | CH$_2$CH$_3$ |
| 2.113 | H | CH$_2$CH$_2$CH$_3$ |
| 2.114 | H | C(CH$_3$)$_2$ |
| 2.115 | H | CH$_2$CH$_2$CH$_2$CH$_3$ |
| 2.116 | H | CHCH(CH$_3$)$_2$ |
| 2.117 | H | CH(CH$_3$)CH$_2$CH$_3$ |
| 2.118 | H | C(CH$_3$)$_3$ |
| 2.119 | H | cyclopropyl |
| 2.120 | H | cyclohexyl |
| 2.121 | H | 2-tetrahydrofuranyl |
| 2.122 | H | 3-tetrahydrofuranyl |
| 2.123 | H | 3-tetrahydrothienyl |
| 2.124 | H | 2-1,3-dioxolanyl |
| 2.125 | H | 2-1,3-dioxanyl |
| 2.126 | H | 4-tetrahydropyranyl |

TABLE A.3

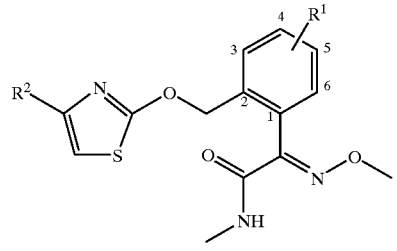

I.3

| No. | R$^1$$_n$ | R$^2$ |
|---|---|---|
| 3.001 | H | C$_6$H$_5$ |
| 3.002 | 3-Cl | C$_6$H$_5$ |
| 3.003 | 4-Cl | C$_6$H$_5$ |
| 3.004 | 6-Cl | C$_6$H$_5$ |
| 3.005 | 4-F | C$_6$H$_5$ |
| 3.006 | 4-OCH$_3$ | C$_6$H$_5$ |
| 3.007 | 3-CH$_3$ | C$_6$H$_5$ |
| 3.008 | 6-CH$_3$ | C$_6$H$_5$ |
| 3.009 | H | 2-F—C$_6$H$_4$ |
| 3.010 | H | 3-F—C$_6$H$_4$ |
| 3.011 | H | 4-F—C$_6$H$_4$ |
| 3.012 | H | 2,3-F$_2$—C$_6$H$_3$ |
| 3.013 | H | 2,4-F$_2$—C$_6$H$_3$ |
| 3.014 | H | 2,5-F$_2$—C$_6$H$_3$ |
| 3.015 | H | 2,6-F$_2$—C$_6$H$_3$ |
| 3.016 | H | 3,4-F$_2$—C$_6$H$_3$ |
| 3.017 | H | 3,5-F$_2$—C$_6$H$_3$ |
| 3.018 | H | 2-Cl—C$_6$H$_4$ |
| 3.019 | H | 3-Cl—C$_6$H$_4$ |
| 3.020 | H | 4-Cl—C$_6$H$_4$ |
| 3.021 | 3-Cl | 4-Cl—C$_6$H$_4$ |
| 3.022 | 4-Cl | 4-Cl—C$_6$H$_4$ |
| 3.023 | 6-Cl | 4-Cl—C$_6$H$_4$ |
| 3.024 | 4-F | 4-Cl—C$_6$H$_4$ |
| 3.025 | 4-OCH$_3$ | 4-Cl—C$_6$H$_4$ |
| 3.026 | 3-CH$_3$ | 4-Cl—C$_6$H$_4$ |
| 3.027 | 6-CH$_3$ | 4-Cl—C$_6$H$_4$ |

TABLE A.3-continued

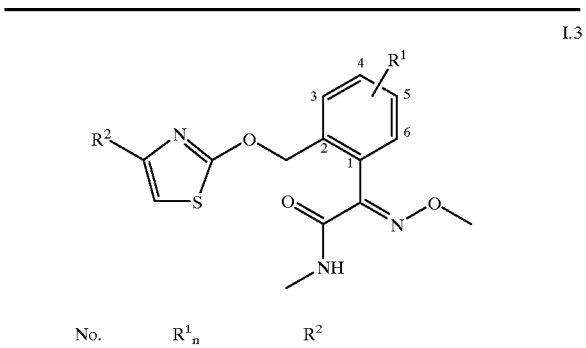

I.3

| No. | $R^1_n$ | $R^2$ |
|---|---|---|
| 3.028 | H | 2,3-Cl$_2$—C$_6$H$_3$ |
| 3.029 | H | 2,4-Cl$_2$—C$_6$H$_3$ |
| 3.030 | H | 2,5-Cl$_2$—C$_6$H$_3$ |
| 3.031 | H | 2,6-Cl$_2$—C$_6$H$_3$ |
| 3.032 | H | 3,4-Cl$_2$—C$_6$H$_3$ |
| 3.033 | H | 3,5-Cl$_2$—C$_6$H$_3$ |
| 3.034 | H | 2,3,4-Cl$_3$—C$_6$H$_2$ |
| 3.035 | H | 2,3,5-Cl$_3$—C$_6$H$_2$ |
| 3.036 | H | 2,3,6-Cl$_3$—C$_6$H$_2$ |
| 3.037 | H | 2,4,5-Cl$_3$—C$_6$H$_2$ |
| 3.038 | H | 2,4,6-Cl$_3$—C$_6$H$_2$ |
| 3.039 | H | 3,4,5-Cl$_3$—C$_6$H$_2$ |
| 3.040 | H | 2-Br—C$_6$H$_4$ |
| 3.041 | H | 3-Br—C$_6$H$_4$ |
| 3.042 | H | 4-Br—C$_6$H$_4$ |
| 3.043 | H | 2,4-Br$_2$—C$_6$H$_3$ |
| 3.044 | H | 2-Br, 4-F—C$_6$H$_3$ |
| 3.045 | H | 2-Br, 4-Cl—C$_6$H$_3$ |
| 3.046 | H | 2-F, 4-Cl—C$_6$H$_3$ |
| 3.047 | H | 3-F, 4-Cl—C$_6$H$_3$ |
| 3.048 | H | 3-Cl, 5-F—C$_6$H$_3$ |
| 3.049 | H | 2-Cl, 4-F—C$_6$H$_3$ |
| 3.050 | H | 2-CN—C$_6$H$_4$ |
| 3.051 | H | 3-CN—C$_6$H$_4$ |
| 3.052 | H | 4-CN—C$_6$H$_4$ |
| 3.053 | H | 3-CN, 4-Cl—C$_6$H$_3$ |
| 3.054 | H | 4-NO$_2$—C$_6$H$_4$ |
| 3.055 | H | 4-H$_2$N—C(=S)—C$_6$H$_4$ |
| 3.056 | H | 2-CH$_3$—C$_6$H$_4$ |
| 3.057 | H | 3-CH$_3$—C$_6$H$_4$ |
| 3.058 | H | 4-CH$_3$—C$_6$H$_4$ |
| 3.059 | H | 2,4-(CH$_3$)$_2$—C$_6$H$_3$ |
| 3.060 | H | 2,5-(CH$_3$)$_2$—C$_6$H$_3$ |
| 3.061 | H | 2,5-(CH$_3$)$_2$—C$_6$H$_3$ |
| 3.062 | H | 2,6-(CH$_3$)$_2$—C$_6$H$_3$ |
| 3.063 | H | 3,4-(CH$_3$)$_2$—C$_6$H$_3$ |
| 3.064 | H | 3,5-(CH$_3$)$_2$—C$_6$H$_3$ |
| 3.065 | H | 2,4,6-(CH$_3$)$_3$—C$_6$H$_2$ |
| 3.066 | H | 3,4,5-(CH$_3$)$_3$—C$_6$H$_2$ |
| 3.067 | H | 2-CH$_3$, 4-Cl—C$_6$H$_3$ |
| 3.068 | H | 2-Cl, 4-CH$_3$—C$_6$H$_3$ |
| 3.069 | H | 3-CH$_3$, 4-Cl—C$_6$H$_3$ |
| 3.070 | H | 3-Cl, 5-CH$_3$—C$_6$H$_3$ |
| 3.071 | H | 2-CN, 4-CH$_3$—C$_6$H$_3$ |
| 3.072 | H | 2-CH$_3$, 4-CN—C$_6$H$_3$ |
| 3.073 | H | 4-(C$_2$H$_5$)—C$_6$H$_4$ |
| 3.074 | H | 4-[C(CH$_3$)$_3$]—C$_6$H$_4$ |
| 3.075 | H | 3-(C$_6$H$_5$)—C$_6$H$_4$ |
| 3.076 | H | 4-(C$_6$H$_5$)—C$_6$H$_4$ |
| 3.077 | H | 2-CF$_3$—C$_6$H$_4$ |
| 3.078 | H | 3-CF$_3$—C$_6$H$_4$ |
| 3.079 | H | 4-CF$_3$—C$_6$H$_4$ |
| 3.080 | H | 3,5-(CF$_3$)$_2$—C$_6$H$_3$ |
| 3.081 | H | 2-Cl, 4-CF$_3$—C$_6$H$_3$ |
| 3.082 | H | 2-OCH$_3$—C$_6$H$_4$ |
| 3.083 | H | 3-OCH$_3$—C$_6$H$_4$ |
| 3.084 | H | 4-OCH$_3$—C$_6$H$_4$ |
| 3.085 | H | 2,4-(OCH$_3$)$_2$—C$_6$H$_3$ |
| 3.086 | H | 3,4-(OCH$_3$)$_2$—C$_6$H$_3$ |
| 3.087 | H | 2,5-(OCH$_3$)$_2$—C$_6$H$_3$ |
| 3.088 | H | 3,5-(OCH$_3$)$_2$—C$_6$H$_3$ |
| 3.089 | H | 3,4,5-(OCH$_3$)$_3$—C$_6$H$_2$ |

TABLE A.3-continued

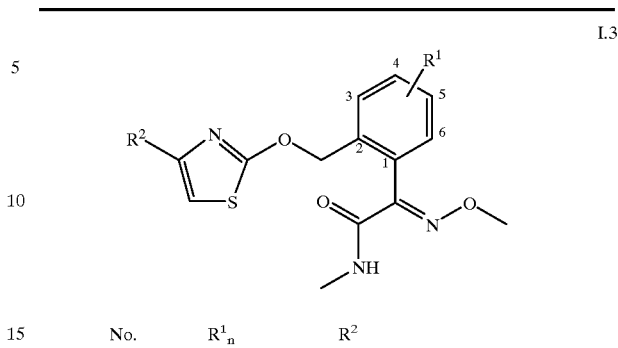

I.3

| No. | $R^1_n$ | $R^2$ |
|---|---|---|
| 3.090 | H | 2-CH$_3$, 4-OCH$_3$—C$_6$H$_3$ |
| 3.091 | H | 2-Cl, 4-OCH$_3$—C$_6$H$_3$ |
| 3.092 | H | 4-OCF$_3$—C$_6$H$_4$ |
| 3.093 | H | 2-OCHF$_2$—C$_6$H$_4$ |
| 3.094 | H | 3-OCHF$_2$—C$_6$H$_4$ |
| 3.095 | H | 4-OCHF$_2$—C$_6$H$_4$ |
| 3.096 | H | 4-(OCF$_2$CHF$_2$)—C$_6$H$_4$ |
| 3.097 | H | 2-F, 4-OCHF$_2$—C$_6$H$_3$ |
| 3.098 | H | 4-(OCH$_2$CH$_3$)—C$_6$H$_4$ |
| 3.099 | H | 4-[OC(CH$_3$)$_3$]—C$_6$H$_4$ |
| 3.100 | H | 3-(CO$_2$CH$_3$)—C$_6$H$_4$ |
| 3.101 | H | 4-(CO$_2$CH$_3$)—C$_6$H$_4$ |
| 3.102 | H | 4-[CO$_2$C(CH$_3$)$_3$]—C$_6$H$_4$ |
| 3.103 | H | 2,3-[O—CH$_2$—O]—C$_6$H$_3$ |
| 3.104 | H | 3,4-[O—CH$_2$—O]—C$_6$H$_3$ |
| 3.105 | H | 3,4-[O—C(CH$_3$)$_2$—O]—C$_6$H$_3$ |
| 3.106 | H | 3,4-[O—CH$_2$CH$_2$—O]—C$_6$H$_3$ |
| 3.107 | H | 2,3-[(CH$_2$)$_4$]—C$_6$H$_3$ |
| 3.108 | H | 3,4-[(CH$_2$)$_4$]—C$_6$H$_3$ |
| 3.109 | H | 2,3-(CH=CH—CH=CH)—C$_6$H$_3$ |
| 3.110 | H | 3,4-(CH=CH—CH=CH)—C$_6$H$_3$ |
| 3.111 | H | CH$_3$ |
| 3.112 | H | CH$_2$CH$_3$ |
| 3.113 | H | CH$_2$CH$_2$CH$_3$ |
| 3.114 | H | C(CH$_3$)$_2$ |
| 3.115 | H | CH$_2$CH$_2$CH$_2$CH$_3$ |
| 3.116 | H | CHCH(CH$_3$)$_2$ |
| 3.117 | H | CH(CH$_3$)CH$_2$CH$_3$ |
| 3.118 | H | C(CH$_3$)$_3$ |
| 3.119 | H | cyclopropyl |
| 3.120 | H | cyclohexyl |
| 3.121 | H | 2-tetrahydrofuranyl |
| 3.122 | H | 3-tetrahydrofuranyl |
| 3.123 | H | 3-tetrahydrothienyl |
| 3.124 | H | 2-1,3-dioxolanyl |
| 3.125 | H | 2-1,3-dioxanyl |
| 3.126 | H | 4-tetrahydropyranyl |

TABLE A.4

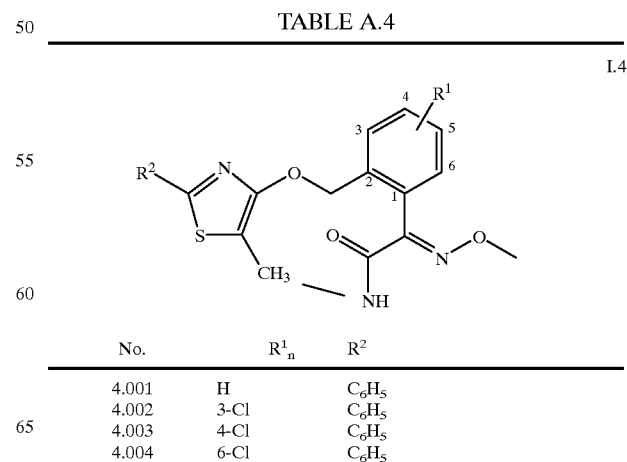

I.4

| No. | $R^1_n$ | $R^2$ |
|---|---|---|
| 4.001 | H | C$_6$H$_5$ |
| 4.002 | 3-Cl | C$_6$H$_5$ |
| 4.003 | 4-Cl | C$_6$H$_5$ |
| 4.004 | 6-Cl | C$_6$H$_5$ |

TABLE A.4-continued

| No. | $R^1_n$ | $R^2$ |
|---|---|---|
| 4.005 | 4-F | $C_6H_5$ |
| 4.006 | 4-OCH$_3$ | $C_6H_5$ |
| 4.007 | 3-CH$_3$ | $C_6H_5$ |
| 4.008 | 6-CH$_3$ | $C_6H_5$ |
| 4.009 | H | 2-F—C$_6$H$_4$ |
| 4.010 | H | 3-F—C$_6$H$_4$ |
| 4.011 | H | 4-F—C$_6$H$_4$ |
| 4.012 | H | 2,3-F$_2$—C$_6$H$_3$ |
| 4.013 | H | 2,4-F$_2$—C$_6$H$_3$ |
| 4.014 | H | 2,5-F$_2$—C$_6$H$_3$ |
| 4.015 | H | 2,6-F$_2$—C$_6$H$_3$ |
| 4.016 | H | 3,4-F$_2$—C$_6$H$_3$ |
| 4.017 | H | 3,5-F$_2$—C$_6$H$_3$ |
| 4.018 | H | 2-Cl—C$_6$H$_4$ |
| 4.019 | H | 3-Cl—C$_6$H$_4$ |
| 4.020 | H | 4-Cl—C$_6$H$_4$ |
| 4.021 | 3-Cl | 4-Cl—C$_6$H$_4$ |
| 4.022 | 4-Cl | 4-Cl—C$_6$H$_4$ |
| 4.023 | 6-Cl | 4-Cl—C$_6$H$_4$ |
| 4.024 | 4-F | 4-Cl—C$_6$H$_4$ |
| 4.025 | 4-OCH$_3$ | 4-Cl—C$_6$H$_4$ |
| 4.026 | 3-CH$_3$ | 4-Cl—C$_6$H$_4$ |
| 4.027 | 6-CH$_3$ | 4-Cl—C$_6$H$_4$ |
| 4.028 | H | 2,3-Cl$_2$—C$_6$H$_3$ |
| 4.029 | H | 2,4-Cl$_2$—C$_6$H$_3$ |
| 4.030 | H | 2,5-Cl$_2$—C$_6$H$_3$ |
| 4.031 | H | 2,6-Cl$_2$—C$_6$H$_3$ |
| 4.032 | H | 3,4-Cl$_2$—C$_6$H$_3$ |
| 4.033 | H | 3,5-Cl$_2$—C$_6$H$_3$ |
| 4.034 | H | 2,3,4-Cl$_3$—C$_6$H$_2$ |
| 4.035 | H | 2,3,5-Cl$_3$—C$_6$H$_2$ |
| 4.036 | H | 2,3,6-Cl$_3$—C$_6$H$_2$ |
| 4.037 | H | 2,4,5-Cl$_3$—C$_6$H$_2$ |
| 4.038 | H | 2,4,6-Cl$_3$—C$_6$H$_2$ |
| 4.039 | H | 3,4,5-Cl$_3$—C$_6$H$_2$ |
| 4.040 | H | 2-Br—C$_6$H$_4$ |
| 4.041 | H | 3-Br—C$_6$H$_4$ |
| 4.042 | H | 4-Br—C$_6$H$_4$ |
| 4.043 | H | 2,4-Br$_2$—C$_6$H$_3$ |
| 4.044 | H | 2-Br, 4-F—C$_6$H$_3$ |
| 4.045 | H | 2-Br, 4-Cl—C$_6$H$_3$ |
| 4.046 | H | 2-F, 4-Cl—C$_6$H$_3$ |
| 4.047 | H | 3-F, 4-Cl—C$_6$H$_3$ |
| 4.048 | H | 3-Cl, 5-F—C$_6$H$_3$ |
| 4.049 | H | 2-Cl, 4-F—C$_6$H$_3$ |
| 4.050 | H | 2-CN—C$_6$H$_4$ |
| 4.051 | H | 3-CN—C$_6$H$_4$ |
| 4.052 | H | 4-CN—C$_6$H$_4$ |
| 4.053 | H | 3-CN, 4-Cl—C$_6$H$_3$ |
| 4.054 | H | 4-NO$_2$—C$_6$H$_4$ |
| 4.055 | H | 4-H$_2$N—C(=S)—C$_6$H$_4$ |
| 4.056 | H | 2-CH$_3$—C$_6$H$_4$ |
| 4.057 | H | 3-CH$_3$—C$_6$H$_4$ |
| 4.058 | H | 4-CH$_3$—C$_6$H$_4$ |
| 4.059 | H | 2,4-(CH$_3$)$_2$—C$_6$H$_3$ |
| 4.060 | H | 2,5-(CH$_3$)$_2$—C$_6$H$_3$ |
| 4.061 | H | 2,5-(CH$_3$)$_2$—C$_6$H$_3$ |
| 4.062 | H | 2,6-(CH$_3$)$_2$—C$_6$H$_3$ |
| 4.063 | H | 3,4-(CH$_3$)$_2$—C$_6$H$_3$ |
| 4.064 | H | 3,5-(CH$_3$)$_2$—C$_6$H$_3$ |
| 4.065 | H | 2,4,6-(CH$_3$)$_3$—C$_6$H$_2$ |
| 4.066 | H | 3,4,5-(CH$_3$)$_3$—C$_6$H$_2$ |
| 4.067 | H | 2-CH$_3$, 4-Cl—C$_6$H$_3$ |
| 4.068 | H | 2-Cl, 4-CH$_3$—C$_6$H$_3$ |
| 4.069 | H | 3-CH$_3$, 4-Cl—C$_6$H$_3$ |
| 4.070 | H | 3-Cl, 5-CH$_3$—C$_6$H$_3$ |
| 4.071 | H | 2-CN, 4-CH$_3$—C$_6$H$_3$ |
| 4.072 | H | 2-CH$_3$, 4-CN—C$_6$H$_3$ |
| 4.073 | H | 4-(C$_2$H$_5$)—C$_6$H$_4$ |
| 4.074 | H | 4-[C(CH$_3$)$_3$]—C$_6$H$_4$ |
| 4.075 | H | 3-(C$_6$H$_5$)—C$_6$H$_4$ |
| 4.076 | H | 4-(C$_6$H$_5$)—C$_6$H$_4$ |
| 4.077 | H | 2-CF$_3$—C$_6$H$_4$ |
| 4.078 | H | 3-CF$_3$—C$_6$H$_4$ |
| 4.079 | H | 4-CF$_3$—C$_6$H$_4$ |
| 4.080 | H | 3,5-(CF$_3$)$_2$—C$_6$H$_3$ |
| 4.081 | H | 2-Cl, 4-CF$_3$—C$_6$H$_3$ |
| 4.082 | H | 2-OCH$_3$—C$_6$H$_4$ |
| 4.083 | H | 3-OCH$_3$—C$_6$H$_4$ |
| 4.084 | H | 4-OCH$_3$—C$_6$H$_4$ |
| 4.085 | H | 2,4-(OCH$_3$)$_2$—C$_6$H$_3$ |
| 4.086 | H | 3,4-(OCH$_3$)$_2$—C$_6$H$_3$ |
| 4.087 | H | 2,5-(OCH$_3$)$_2$—C$_6$H$_3$ |
| 4.088 | H | 3,5-(OCH$_3$)$_2$—C$_6$H$_3$ |
| 4.089 | H | 3,4,5-(OCH$_3$)$_3$—C$_6$H$_2$ |
| 4.090 | H | 2-CH$_3$, 4-OCH$_3$—C$_6$H$_3$ |
| 4.091 | H | 2-Cl, 4-OCH$_3$—C$_6$H$_3$ |
| 4.092 | H | 4-OCF$_3$—C$_6$H$_4$ |
| 4.093 | H | 2-OCHF$_2$—C$_6$H$_4$ |
| 4.094 | H | 3-OCHF$_2$—C$_6$H$_4$ |
| 4.095 | H | 4-OCHF$_2$—C$_6$H$_4$ |
| 4.096 | H | 4-(OCF$_2$CHF$_2$)—C$_6$H$_4$ |
| 4.097 | H | 2-F, 4-OCHF$_2$—C$_6$H$_3$ |
| 4.098 | H | 4-(OCH$_2$CH$_3$)—C$_6$H$_4$ |
| 4.099 | H | 4-[OC(CH$_3$)$_3$]—C$_6$H$_4$ |
| 4.100 | H | 3-(CO$_2$CH$_3$)—C$_6$H$_4$ |
| 4.101 | H | 4-(CO$_2$CH$_3$)—C$_6$H$_4$ |
| 4.102 | H | 4-[CO$_2$C(CH$_3$)$_3$]—C$_6$H$_4$ |
| 4.103 | H | 2,3-[O—CH$_2$—O]—C$_6$H$_3$ |
| 4.104 | H | 3,4-[O—CH$_2$—O]—C$_6$H$_3$ |
| 4.105 | H | 3,4-[O—C(CH$_3$)$_2$—O]—C$_6$H$_3$ |
| 4.106 | H | 3,4-[O—CH$_2$CH$_2$—O]—C$_6$H$_3$ |
| 4.107 | H | 2,3-[(CH$_2$)$_4$]—C$_6$H$_3$ |
| 4.108 | H | 3,4-[(CH$_2$)$_4$]—C$_6$H$_3$ |
| 4.109 | H | 2,3-(CH=CH$_2$—CH=CH)—C$_6$H$_3$ |
| 4.110 | H | 3,4-(CH=CH—CH=CH)—C$_6$H$_3$ |
| 4.111 | H | CH$_3$ |
| 4.112 | H | CH$_2$CH$_3$ |
| 4.113 | H | CH$_2$CH$_2$CH$_3$ |
| 4.114 | H | C(CH$_3$)$_2$ |
| 4.115 | H | CH$_2$CH$_2$CH$_2$CH$_3$ |
| 4.116 | H | CHCH(CH$_3$)$_2$ |
| 4.117 | H | CH(CH$_3$)CH$_2$CH$_3$ |
| 4.118 | H | C(CH$_3$)$_3$ |
| 4.119 | H | cyclopropyl |
| 4.120 | H | cyclohexyl |
| 4.121 | H | 2-tetrahydrofuranyl |
| 4.122 | H | 3-tetrahydrofuranyl |
| 4.123 | H | 3-tetrahydrothienyl |
| 4.124 | H | 2-1,3-doxolanyl [sic] |
| 4.125 | H | 2-1,3-dioxanyl |
| 4.126 | H | 4-tetrahydropyranyl |

TABLE A.5

I.5

| No. | $R^1_n$ | $R^2$ |
|---|---|---|
| 5.001 | H | $C_6H_5$ |
| 5.002 | 3-Cl | $C_6H_5$ |
| 5.003 | 4-Cl | $C_6H_5$ |
| 5.004 | 6-Cl | $C_6H_5$ |
| 5.005 | 4-F | $C_6H_5$ |
| 5.006 | 4-OCH$_3$ | $C_6H_5$ |
| 5.007 | 3-CH$_3$ | $C_6H_5$ |
| 5.008 | 6-CH$_3$ | $C_6H_5$ |
| 5.009 | H | 2-F—$C_6H_4$ |
| 5.010 | H | 3-F—$C_6H_4$ |
| 5.011 | H | 4-F—$C_6H_4$ |
| 5.012 | H | 2,3-F$_2$—$C_6H_3$ |
| 5.013 | H | 2,4-F$_2$—$C_6H_3$ |
| 5.014 | H | 2,5-F$_2$—$C_6H_3$ |
| 5.015 | H | 2,6-F$_2$—$C_6H_3$ |
| 5.016 | H | 3,4-F$_2$—$C_6H_3$ |
| 5.017 | H | 3,5-F$_2$—$C_6H_3$ |
| 5.018 | H | 2-Cl—$C_6H_4$ |
| 5.019 | H | 3-Cl—$C_6H_4$ |
| 5.020 | H | 4-Cl—$C_6H_4$ |
| 5.021 | 3-Cl | 4-Cl—$C_6H_4$ |
| 5.022 | 4-Cl | 4-Cl—$C_6H_4$ |
| 5.023 | 6-Cl | 4-Cl—$C_6H_4$ |
| 5.024 | 4-F | 4-Cl—$C_6H_4$ |
| 5.025 | 4-OCH$_3$ | 4-Cl—$C_6H_4$ |
| 5.026 | 3-CH$_3$ | 4-Cl—$C_6H_4$ |
| 5.027 | 6-CH$_3$ | 4-Cl—$C_6H_4$ |
| 5.028 | H | 2,3-Cl$_2$—$C_6H_3$ |
| 5.029 | H | 2,4-Cl$_2$—$C_6H_3$ |
| 5.030 | H | 2,5-Cl$_2$—$C_6H_3$ |
| 5.031 | H | 2,6-Cl$_2$—$C_6H_3$ |
| 5.032 | H | 3,4-Cl$_2$—$C_6H_3$ |
| 5.033 | H | 3,5-Cl$_2$—$C_6H_3$ |
| 5.034 | H | 2,3,4-Cl$_3$—$C_6H_2$ |
| 5.035 | H | 2,3,5-Cl$_3$—$C_6H_2$ |
| 5.036 | H | 2,3,6-Cl$_3$—$C_6H_2$ |
| 5.037 | H | 2,4,5-Cl$_3$—$C_6H_2$ |
| 5.038 | H | 2,4,6-Cl$_3$—$C_6H_2$ |
| 5.039 | H | 3,4,5-Cl$_3$—$C_6H_2$ |
| 5.040 | H | 2-Br—$C_6H_4$ |
| 5.041 | H | 3-Br—$C_6H_4$ |
| 5.042 | H | 4-Br—$C_6H_4$ |
| 5.043 | H | 2,4-Br$_2$—$C_6H_3$ |
| 5.044 | H | 2-Br, 4-F—$C_6H_3$ |
| 5.045 | H | 2-Br, 4-Cl—$C_6H_3$ |
| 5.046 | H | 2-F, 4-Cl—$C_6H_3$ |
| 5.047 | H | 3-F, 4-Cl—$C_6H_3$ |
| 5.048 | H | 3-Cl, 5-F—$C_6H_3$ |
| 5.049 | H | 2-Cl, 4-F—$C_6H_3$ |
| 5.050 | H | 2-CN—$C_6H_4$ |
| 5.051 | H | 3-CN—$C_6H_4$ |
| 5.052 | H | 4-CN—$C_6H_4$ |
| 5.053 | H | 3-CN, 4-Cl—$C_6H_3$ |
| 5.054 | H | 4-NO$_2$—$C_6H_4$ |
| 5.055 | H | 4-H$_2$N—C(=S)—$C_6H_4$ |
| 5.056 | H | 2-CH$_3$—$C_6H_4$ |
| 5.057 | H | 3-CH$_3$—$C_6H_4$ |
| 5.058 | H | 4-CH$_3$—$C_6H_4$ |
| 5.059 | H | 2,4-(CH$_3$)$_2$—$C_6H_3$ |
| 5.060 | H | 2,5-(CH$_3$)$_2$—$C_6H_3$ |
| 5.061 | H | 2,5-(CH$_3$)$_2$—$C_6H_3$ |
| 5.062 | H | 2,6-(CH$_3$)$_2$—$C_6H_3$ |
| 5.063 | H | 3,4-(CH$_3$)$_2$—$C_6H_3$ |
| 5.064 | H | 3,5-(CH$_3$)$_2$—$C_6H_3$ |
| 5.065 | H | 2,4,6-(CH$_3$)$_3$—$C_6H_2$ |
| 5.066 | H | 3,4,5-(CH$_3$)$_3$—$C_6H_2$ |
| 5.067 | H | 2-CH$_3$, 4-Cl—$C_6H_3$ |
| 5.068 | H | 2-Cl, 4-CH$_3$—$C_6H_3$ |
| 5.069 | H | 3-CH$_3$, 4-Cl—$C_6H_3$ |
| 5.070 | H | 3-Cl, 5-CH$_3$—$C_6H_3$ |
| 5.071 | H | 2-CN, 4-CH$_3$—$C_6H_3$ |
| 5.072 | H | 2-CH$_3$, 4-CN—$C_6H_3$ |
| 5.073 | H | 4-(C$_2$H$_5$)—$C_6H_4$ |
| 5.074 | H | 4-[C(CH$_3$)$_3$]—$C_6H_4$ |
| 5.075 | H | 3-(C$_6$H$_5$)—$C_6H_4$ |
| 5.076 | H | 4-(C$_6$H$_5$)—$C_6H_4$ |
| 5.077 | H | 2-CF$_3$—$C_6H_4$ |
| 5.078 | H | 3-CF$_3$—$C_6H_4$ |
| 5.079 | H | 4-CF$_3$—$C_6H_4$ |
| 5.080 | H | 3,5-(CF$_3$)$_2$—$C_6H_3$ |
| 5.081 | H | 2-Cl, 4-CF$_3$—$C_6H_3$ |
| 5.082 | H | 2-OCH$_3$—$C_6H_4$ |
| 5.083 | H | 3-OCH$_3$—$C_6H_4$ |
| 5.084 | H | 4-OCH$_3$—$C_6H_4$ |
| 5.085 | H | 2,4-(OCH$_3$)$_2$—$C_6H_3$ |
| 5.086 | H | 3,4-(OCH$_3$)$_2$—$C_6H_3$ |
| 5.087 | H | 2,5-(OCH$_3$)$_2$—$C_6H_3$ |
| 5.088 | H | 3,5-(OCH$_3$)$_2$—$C_6H_3$ |
| 5.089 | H | 3,4,5-(OCH$_3$)$_3$—$C_6H_2$ |
| 5.090 | H | 2-CH$_3$, 4-OCH$_3$—$C_6H_3$ |
| 5.091 | H | 2-Cl, 4-OCH$_3$—$C_6H_3$ |
| 5.092 | H | 4-OCF$_3$—$C_6H_4$ |
| 5.093 | H | 2-OCHF$_2$—$C_6H_4$ |
| 5.094 | H | 3-OCHF$_2$—$C_6H_4$ |
| 5.095 | H | 4-OCHF$_2$—$C_6H_4$ |
| 5.096 | H | 4-(OCF$_2$CHF$_2$)—$C_6H_4$ |
| 5.097 | H | 2-F, 4-OCHF$_2$—$C_6H_3$ |
| 5.098 | H | 4-(OCH$_2$CH$_3$)—$C_6H_4$ |
| 5.099 | H | 4-[OC(CH$_3$)$_3$]—$C_6H_4$ |
| 5.100 | H | 3-(CO$_2$CH$_3$)—$C_6H_4$ |
| 5.101 | H | 4-(CO$_2$CH$_3$)—$C_6H_4$ |
| 5.102 | H | 4-[CO$_2$C(CH$_3$)$_3$]—$C_6H_4$ |
| 5.103 | H | 2,3-[O—CH$_2$—O]—$C_6H_3$ |
| 5.104 | H | 3,4-[O—CH$_2$—O]—$C_6H_3$ |
| 5.105 | H | 3,4-[O—C(CH$_3$)$_2$—O]—$C_6H_3$ |
| 5.106 | H | 3,4-[O—CH$_2$CH$_2$—O]—$C_6H_3$ |
| 5.107 | H | 2,3-[(CH$_2$)$_4$]—$C_6H_3$ |
| 5.108 | H | 3,4-[(CH$_2$)$_4$]—$C_6H_3$ |
| 5.109 | H | 2,3-(CH=CH—CH=CH)—$C_6H_3$ |
| 5.110 | H | 3,4-(CH=CH—CH=CH)—$C_6H_3$ |
| 5.111 | H | CH$_3$ |
| 5.112 | H | CH$_2$CH$_3$ |
| 5.113 | H | CH$_2$CH$_2$CH$_3$ |
| 5.114 | H | C(CH$_3$)$_2$ |
| 5.115 | H | CH$_2$CH$_2$CH$_2$CH$_3$ |
| 5.116 | H | CHCH(CH$_3$)$_2$ |
| 5.117 | H | CH(CH$_3$)CH$_2$CH$_3$ |
| 5.118 | H | C(CH$_3$)$_3$ |
| 5.119 | H | cyclopropyl |
| 5.120 | H | cyclohexyl |
| 5.121 | H | 2-tetrahydrofuranyl |
| 5.122 | H | 3-tetrahydrofuranyl |
| 5.123 | H | 3-tetrahydrothienyl |
| 5.124 | H | 2-1,3-dioxolanyl |

TABLE A.5-continued

I.5

| No. | $R^1_n$ | $R^2$ |
|---|---|---|
| 5.125 | H | 2-1,3-dioxanyl |
| 5.126 | H | 4-tetrahydropyranyl |

TABLE A.6

I.6

| No. | $R^1_n$ | $R^2$ |
|---|---|---|
| 6.001 | H | $C_6H_5$ |
| 6.002 | 3-Cl | $C_6H_5$ |
| 6.003 | 4-Cl | $C_6H_5$ |
| 6.004 | 6-Cl | $C_6H_5$ |
| 6.005 | 4-F | $C_6H_5$ |
| 6.006 | 4-$OCH_3$ | $C_6H_5$ |
| 6.007 | 3-$CH_3$ | $C_6H_5$ |
| 6.008 | 6-$CH_3$ | $C_6H_5$ |
| 6.009 | H | 2-F—$C_6H_4$ |
| 6.010 | H | 3-F—$C_6H_4$ |
| 6.011 | H | 4-F—$C_6H_4$ |
| 6.012 | H | 2,3-$F_2$—$C_6H_3$ |
| 6.013 | H | 2,4-$F_2$—$C_6H_3$ |
| 6.014 | H | 2,5-$F_2$—$C_6H_3$ |
| 6.015 | H | 2,6-$F_2$—$C_6H_3$ |
| 6.016 | H | 3,4-$F_2$—$C_6H_3$ |
| 6.017 | H | 3,5-$F_2$—$C_6H_3$ |
| 6.018 | H | 2-Cl—$C_6H_4$ |
| 6.019 | H | 3-Cl—$C_6H_4$ |
| 6.020 | H | 4-Cl—$C_6H_4$ |
| 6.021 | 3-Cl | 4-Cl—$C_6H_4$ |
| 6.022 | 4-Cl | 4-Cl—$C_6H_4$ |
| 6.023 | 6-Cl | 4-Cl—$C_6H_4$ |
| 6.024 | 4-F | 4-Cl—$C_6H_4$ |
| 6.025 | 4-$OCH_3$ | 4-Cl—$C_6H_4$ |
| 6.026 | 3-$CH_3$ | 4-Cl—$C_6H_4$ |
| 6.027 | 6-$CH_3$ | 4-Cl—$C_6H_4$ |
| 6.028 | H | 2,3-$Cl_2$—$C_6H_3$ |
| 6.029 | H | 2,4-$Cl_2$—$C_6H_3$ |
| 6.030 | H | 2,5-$Cl_2$—$C_6H_3$ |
| 6.031 | H | 2,6-$Cl_2$—$C_6H_3$ |
| 6.032 | H | 3,4-$Cl_2$—$C_6H_3$ |
| 6.033 | H | 3,5-$Cl_2$—$C_6H_3$ |
| 6.034 | H | 2,3,4-$Cl_3$—$C_6H_2$ |
| 6.035 | H | 2,3,5-$Cl_3$—$C_6H_2$ |
| 6.036 | H | 2,3,6-$Cl_3$—$C_6H_2$ |
| 6.037 | H | 2,4,5-$Cl_3$—$C_6H_2$ |
| 6.038 | H | 2,4,6-$Cl_3$—$C_6H_2$ |

TABLE A.6-continued

I.6

| No. | $R^1_n$ | $R^2$ |
|---|---|---|
| 6.039 | H | 3,4,5-$Cl_3$—$C_6H_2$ |
| 6.040 | H | 2-Br—$C_6H_4$ |
| 6.041 | H | 3-Br—$C_6H_4$ |
| 6.042 | H | 4-Br—$C_6H_4$ |
| 6.043 | H | 2,4-$Br_2$—$C_6H_3$ |
| 6.044 | H | 2-Br, 4-F—$C_6H_3$ |
| 6.045 | H | 2-Br, 4-Cl—$C_6H_3$ |
| 6.046 | H | 2-F, 4-Cl—$C_6H_3$ |
| 6.047 | H | 3-F, 4-Cl—$C_6H_3$ |
| 6.048 | H | 3-Cl, 5-F—$C_6H_3$ |
| 6.049 | H | 2-Cl, 4-F—$C_6H_3$ |
| 6.050 | H | 2-CN—$C_6H_4$ |
| 6.051 | H | 3-CN—$C_6H_4$ |
| 6.052 | H | 4-CN—$C_6H_4$ |
| 6.053 | H | 3-CN, 4-Cl—$C_6H_3$ |
| 6.054 | H | 4-$NO_2$—$C_6H_4$ |
| 6.055 | H | 4-$H_2N$—C(=S)—$C_6H_4$ |
| 6.056 | H | 2-$CH_3$—$C_6H_4$ |
| 6.057 | H | 3-$CH_3$—$C_6H_4$ |
| 6.058 | H | 4-$CH_3$—$C_6H_4$ |
| 6.059 | H | 2,4-$(CH_3)_2$—$C_6H_3$ |
| 6.060 | H | 2,5-$(CH_3)_2$—$C_6H_3$ |
| 6.061 | H | 2,5-$(CH_3)_2$—$C_6H_3$ |
| 6.062 | H | 2,6-$(CH_3)_2$—$C_6H_3$ |
| 6.063 | H | 3,4-$(CH_3)_2$—$C_6H_3$ |
| 6.064 | H | 3,5-$(CH_3)_2$—$C_6H_3$ |
| 6.065 | H | 2,4,6-$(CH_3)_3$—$C_6H_2$ |
| 6.066 | H | 3,4,5-$(CH_3)_3$—$C_6H_2$ |
| 6.067 | H | 2-$CH_3$, 4-Cl—$C_6H_3$ |
| 6.068 | H | 2-Cl, 4-$CH_3$—$C_6H_3$ |
| 6.069 | H | 3-$CH_3$, 4-Cl—$C_6H_3$ |
| 6.070 | H | 3-Cl, 5-$CH_3$—$C_6H_3$ |
| 6.071 | H | 2-CN, 4-$CH_3$—$C_6H_3$ |
| 6.072 | H | 2-$CH_3$, 4-CN—$C_6H_3$ |
| 6.073 | H | 4-$(C_2H_5)$—$C_6H_4$ |
| 6.074 | H | 4-$[C(CH_3)_3]$—$C_6H_4$ |
| 6.075 | H | 3-$(C_6H_5)$—$C_6H_4$ |
| 6.076 | H | 4-$(C_6H_5)$—$C_6H_4$ |
| 6.077 | H | 2-$CF_3$—$C_6H_4$ |
| 6.078 | H | 3-$CF_3$—$C_6H_4$ |
| 6.079 | H | 4-$CF_3$—$C_6H_4$ |
| 6.080 | H | 3,5-$(CF_3)_2$—$C_6H_3$ |
| 6.081 | H | 2-Cl, 4-$CF_3$—$C_6H_3$ |
| 6.082 | H | 2-$OCH_3$—$C_6H_4$ |
| 6.083 | H | 3-$OCH_3$—$C_6H_4$ |
| 6.084 | H | 4-$OCH_3$—$C_6H_4$ |
| 6.085 | H | 2,4-$(OCH_3)_2$—$C_6H_3$ |
| 6.086 | H | 3,4-$(OCH_3)_2$—$C_6H_3$ |
| 6.087 | H | 2,5-$(OCH_3)_2$—$C_6H_3$ |
| 6.088 | H | 3,5-$(OCH_3)_2$—$C_6H_3$ |
| 6.089 | H | 3,4,5-$(OCH_3)_3$—$C_6H_2$ |
| 6.090 | H | 2-$CH_3$, 4-$OCH_3$—$C_6H_3$ |
| 6.091 | H | 2-Cl, 4-$OCH_3$—$C_6H_3$ |
| 6.092 | H | 4-$OCF_3$—$C_6H_4$ |
| 6.093 | H | 2-$OCHF_2$—$C_6H_4$ |
| 6.094 | H | 3-$OCHF_2$—$C_6H_4$ |
| 6.095 | H | 4-$OCHF_2$—$C_6H_4$ |
| 6.096 | H | 4-$(OCF_2CHF_2)$—$C_6H_4$ |
| 6.097 | H | 2-F, 4-$OCHF_2$—$C_6H_3$ |
| 6.098 | H | 4-$(OCH_2CH_3)$—$C_6H_4$ |
| 6.099 | H | 4-$[OC(CH_3)_3]$—$C_6H_4$ |
| 6.100 | H | 3-$(CO_2CH_3)$—$C_6H_4$ |

TABLE A.6-continued

I.6

| No. | $R^1_n$ | $R^2$ |
|---|---|---|
| 6.101 | H | 4-(CO$_2$CH$_3$)—C$_6$H$_4$ |
| 6.102 | H | 4-[CO$_2$C(CH$_3$)$_3$]—C$_6$H$_4$ |
| 6.103 | H | 2,3-[O—CH$_2$—O]—C$_6$H$_3$ |
| 6.104 | H | 3,4-[O—CH$_2$—O]—C$_6$H$_3$ |
| 6.105 | H | 3,4-[O—C(CH$_3$)$_2$—O]—C$_6$H$_3$ |
| 6.106 | H | 3,4-[O—CH$_2$CH$_2$—O]—C$_6$H$_3$ |
| 6.107 | H | 2,3-[(CH$_2$)$_4$]—C$_6$H$_3$ |
| 6.108 | H | 3,4-[(CH$_2$)$_4$]—C$_6$H$_3$ |
| 6.109 | H | 2,3-(CH=CH—CH=CH)—C$_6$H$_3$ |
| 6.110 | H | 3,4-(CH=CH—CH=CH)—C$_6$H$_3$ |
| 6.111 | H | CH$_3$ |
| 6.112 | H | CH$_2$CH$_3$ |
| 6.113 | H | CH$_2$CH$_2$CH$_3$ |
| 6.114 | H | C(CH$_3$)$_2$ |
| 6.115 | H | CH$_2$CH$_2$CH$_2$CH$_3$ |
| 6.116 | H | CHCH(CH$_3$)$_2$ |
| 6.117 | H | CH(CH$_3$)CH$_2$CH$_3$ |
| 6.118 | H | C(CH$_3$)$_3$ |
| 6.119 | H | cyclopropyl |
| 6.120 | H | cyclohexyl |
| 6.121 | H | 2-tetrahydrofuranyl |
| 6.122 | H | 3-tetrahydrofuranyl |
| 6.123 | H | 3-tetrahydrothienyl |
| 6.124 | H | 2-1,3-dioxolanyl |
| 6.125 | H | 2-1,3-dioxanyl |
| 6.126 | H | 4-tetrahydropyranyl |

TABLE A.7

I.7

| No. | $R^1_n$ | $R^2$ |
|---|---|---|
| 7.001 | H | C$_6$H$_5$ |
| 7.002 | 3-Cl | C$_6$H$_5$ |
| 7.003 | 4-Cl | C$_6$H$_5$ |
| 7.004 | 6-Cl | C$_6$H$_5$ |
| 7.005 | 4-F | C$_6$H$_5$ |
| 7.006 | 4-OCH$_3$ | C$_6$H$_5$ |
| 7.007 | 3-CH$_3$ | C$_6$H$_5$ |
| 7.008 | 6-CH$_3$ | C$_6$H$_5$ |
| 7.009 | H | 2-F—C$_6$H$_4$ |
| 7.010 | H | 3-F—C$_6$H$_4$ |
| 7.011 | H | 4-F—C$_6$H$_4$ |
| 7.012 | H | 2,3-F$_2$—C$_6$H$_3$ |
| 7.013 | H | 2,4-F$_2$—C$_6$H$_3$ |
| 7.014 | H | 2,5-F$_2$—C$_6$H$_3$ |
| 7.015 | H | 2,6-F$_2$—C$_6$H$_3$ |

TABLE A.7-continued

I.7

| No. | $R^1_n$ | $R^2$ |
|---|---|---|
| 7.016 | H | 3,4-F$_2$—C$_6$H$_3$ |
| 7.017 | H | 3,5-F$_2$—C$_6$H$_3$ |
| 7.018 | H | 2-Cl—C$_6$H$_4$ |
| 7.019 | H | 3-Cl—C$_6$H$_4$ |
| 7.020 | H | 4-Cl—C$_6$H$_4$ |
| 7.021 | 3-Cl | 4-Cl—C$_6$H$_4$ |
| 7.022 | 4-Cl | 4-Cl—C$_6$H$_4$ |
| 7.023 | 6-Cl | 4-Cl—C$_6$H$_4$ |
| 7.024 | 4-F | 4-Cl—C$_6$H$_4$ |
| 7.025 | 4-OCH$_3$ | 4-Cl—C$_6$H$_4$ |
| 7.026 | 3-CH$_3$ | 4-Cl—C$_6$H$_4$ |
| 7.027 | 6-CH$_3$ | 4-Cl—C$_6$H$_4$ |
| 7.028 | H | 2,3-Cl$_2$—C$_6$H$_3$ |
| 7.029 | H | 2,4-Cl$_2$—C$_6$H$_3$ |
| 7.030 | H | 2,5-Cl$_2$—C$_6$H$_3$ |
| 7.031 | H | 2,6-Cl$_2$—C$_6$H$_3$ |
| 7.032 | H | 3,4-Cl$_2$—C$_6$H$_3$ |
| 7.033 | H | 3,5-Cl$_2$—C$_6$H$_3$ |
| 7.034 | H | 2,3,4-Cl$_3$—C$_6$H$_2$ |
| 7.035 | H | 2,3,5-Cl$_3$—C$_6$H$_2$ |
| 7.036 | H | 2,3,6-Cl$_3$—C$_6$H$_2$ |
| 7.037 | H | 2,4,5-Cl$_3$—C$_6$H$_2$ |
| 7.038 | H | 2,4,6-Cl$_3$—C$_6$H$_2$ |
| 7.039 | H | 3,4,5-Cl$_3$—C$_6$H$_2$ |
| 7.040 | H | 2-Br—C$_6$H$_4$ |
| 7.041 | H | 3-Br—C$_6$H$_4$ |
| 7.042 | H | 4-Br—C$_6$H$_4$ |
| 7.043 | H | 2,4-Br$_2$—C$_6$H$_3$ |
| 7.044 | H | 2-Br, 4-F—C$_6$H$_3$ |
| 7.045 | H | 2-Br, 4-Cl—C$_6$H$_3$ |
| 7.046 | H | 2-F, 4-Cl—C$_6$H$_3$ |
| 7.047 | H | 3-F, 4-Cl—C$_6$H$_3$ |
| 7.048 | H | 3-Cl, 5-F—C$_6$H$_3$ |
| 7.049 | H | 2-Cl, 4-F—C$_6$H$_3$ |
| 7.050 | H | 2-CN—C$_6$H$_4$ |
| 7.051 | H | 3-CN—C$_6$H$_4$ |
| 7.052 | H | 4-CN—C$_6$H$_4$ |
| 7.053 | H | 3-CN, 4-Cl—C$_6$H$_3$ |
| 7.054 | H | 4-NO$_2$—C$_6$H$_4$ |
| 7.055 | H | 4-H$_2$N—C(=S)—C$_6$H$_4$ |
| 7.056 | H | 2-CH$_3$—C$_6$H$_4$ |
| 7.057 | H | 3-CH$_3$—C$_6$H$_4$ |
| 7.058 | H | 4-CH$_3$—C$_6$H$_4$ |
| 7.059 | H | 2,4-(CH$_3$)$_2$—C$_6$H$_3$ |
| 7.060 | H | 2,5-(CH$_3$)$_2$—C$_6$H$_3$ |
| 7.061 | H | 2,5-(CH$_3$)$_2$—C$_6$H$_3$ |
| 7.062 | H | 2,6-(CH$_3$)$_2$—C$_6$H$_3$ |
| 7.063 | H | 3,4-(CH$_3$)$_2$—C$_6$H$_3$ |
| 7.064 | H | 3,5-(CH$_3$)$_2$—C$_6$H$_3$ |
| 7.065 | H | 2,4,6-(CH$_3$)$_3$—C$_6$H$_2$ |
| 7.066 | H | 3,4,5-(CH$_3$)$_3$—C$_6$H$_2$ |
| 7.067 | H | 2-CH$_3$, 4-Cl—C$_6$H$_3$ |
| 7.068 | H | 2-Cl, 4-CH$_3$—C$_6$H$_3$ |
| 7.069 | H | 3-CH$_3$, 4-Cl—C$_6$H$_3$ |
| 7.070 | H | 3-Cl, 5-CH$_3$—C$_6$H$_3$ |
| 7.071 | H | 2-CN, 4-CH$_3$—C$_6$H$_3$ |
| 7.072 | H | 2-CH$_3$, 4-CN—C$_6$H$_3$ |
| 7.073 | H | 4-(C$_2$H$_5$)—C$_6$H$_4$ |
| 7.074 | H | 4-[C(CH$_3$)$_3$]—C$_6$H$_4$ |
| 7.075 | H | 3-(C$_6$H$_5$)—C$_6$H$_4$ |
| 7.076 | H | 4-(C$_6$H$_5$)—C$_6$H$_4$ |
| 7.077 | H | 2-CF$_3$—C$_6$H$_4$ |

TABLE A.7-continued

I.7

Structure: thiadiazole-O-CH2-phenyl(R1n) with C(=NOCH3)C(=O)NHCH3 substituent; R2 on thiadiazole

| No. | R1n | R2 |
|---|---|---|
| 7.078 | H | 3-CF$_3$—C$_6$H$_4$ |
| 7.079 | H | 4-CF$_3$—C$_6$H$_4$ |
| 7.080 | H | 3,5-(CF$_3$)$_2$—C$_6$H$_3$ |
| 7.081 | H | 2-Cl, 4-CF$_3$—C$_6$H$_3$ |
| 7.082 | H | 2-OCH$_3$—C$_6$H$_4$ |
| 7.083 | H | 3-OCH$_3$—C$_6$H$_4$ |
| 7.084 | H | 4-OCH$_3$—C$_6$H$_4$ |
| 7.085 | H | 2,4-(OCH$_3$)$_2$—C$_6$H$_3$ |
| 7.086 | H | 3,4-(OCH$_3$)$_2$—C$_6$H$_3$ |
| 7.087 | H | 2,5-(OCH$_3$)$_2$—C$_6$H$_3$ |
| 7.088 | H | 3,5-(OCH$_3$)$_2$—C$_6$H$_3$ |
| 7.089 | H | 3,4,5-(OCH$_3$)$_3$—C$_6$H$_2$ |
| 7.090 | H | 2-CH$_3$, 4-OCH$_3$—C$_6$H$_3$ |
| 7.091 | H | 2-Cl, 4-OCH$_3$—C$_6$H$_3$ |
| 7.092 | H | 4-OCF$_3$—C$_6$H$_4$ |
| 7.093 | H | 2-OCHF$_2$—C$_6$H$_4$ |
| 7.094 | H | 3-OCHF$_2$—C$_6$H$_4$ |
| 7.095 | H | 4-OCHF$_2$—C$_6$H$_4$ |
| 7.096 | H | 4-(OCF$_2$CHF$_2$)—C$_6$H$_4$ |
| 7.097 | H | 2-F, 4-OCHF$_2$—C$_6$H$_3$ |
| 7.098 | H | 4-(OCH$_2$CH$_3$)—C$_6$H$_4$ |
| 7.099 | H | 4-[OC(CH$_3$)$_3$]—C$_6$H$_4$ |
| 7.100 | H | 3-(CO$_2$CH$_3$)—C$_6$H$_4$ |
| 7.101 | H | 4-(CO$_2$CH$_3$)—C$_6$H$_4$ |
| 7.102 | H | 4-[CO$_2$C(CH$_3$)$_3$]—C$_6$H$_4$ |
| 7.103 | H | 2,3-[O—CH$_2$—O]—C$_6$H$_3$ |
| 7.104 | H | 3,4-[O—CH$_2$—O]—C$_6$H$_3$ |
| 7.105 | H | 3,4-[O—C(CH$_3$)$_2$—O]—C$_6$H$_3$ |
| 7.106 | H | 3,4-[O—CH$_2$CH$_2$—O]—C$_6$H$_3$ |
| 7.107 | H | 2,3-[(CH$_2$)$_4$]—C$_6$H$_3$ |
| 7.108 | H | 3,4-[(CH$_2$)$_4$]—C$_6$H$_3$ |
| 7.109 | H | 2,3-(CH=CH—CH=CH)—C$_6$H$_3$ |
| 7.110 | H | 3,4-(CH=CH—CH=CH)—C$_6$H$_3$ |
| 7.111 | H | CH$_3$ |
| 7.112 | H | CH$_2$CH$_3$ |
| 7.113 | H | CH$_2$CH$_2$CH$_3$ |
| 7.114 | H | C(CH$_3$)$_2$ |
| 7.115 | H | CH$_2$CH$_2$CH$_2$CH$_3$ |
| 7.116 | H | CHCH(CH$_3$)$_2$ |
| 7.117 | H | CH(CH$_3$)CH$_2$CH$_3$ |
| 7.118 | H | C(CH$_3$)$_3$ |
| 7.119 | H | cyclopropyl |
| 7.120 | H | cyclohexyl |
| 7.121 | H | 2-tetrahydrofuranyl |
| 7.122 | H | 3-tetrahydrofuranyl |
| 7.123 | H | 3-tetrahydrothienyl |
| 7.124 | H | 2-1,3-dioxolanyl |
| 7.125 | H | 2-1,3-dioxanyl |
| 7.126 | H | 4-tetrahydropyranyl |

TABLE A.8

I.8

Structure: isoxazole-O-CH2-phenyl(R1n) with C(=NOCH3)C(=O)NHCH3 substituent; R2 on isoxazole

| No. | R1n | R2 |
|---|---|---|
| 8.001 | H | C$_6$H$_5$ |
| 8.002 | 3-Cl | C$_6$H$_5$ |
| 8.003 | 4-Cl | C$_6$H$_5$ |
| 8.004 | 6-Cl | C$_6$H$_5$ |
| 8.005 | 4-F | C$_6$H$_5$ |
| 8.006 | 4-OCH$_3$ | C$_6$H$_5$ |
| 8.007 | 3-CH$_3$ | C$_6$H$_5$ |
| 8.008 | 6-CH$_3$ | C$_6$H$_5$ |
| 8.009 | H | 2-F—C$_6$H$_4$ |
| 8.010 | H | 3-F—C$_6$H$_4$ |
| 8.011 | H | 4-F—C$_6$H$_4$ |
| 8.012 | H | 2,3-F$_2$—C$_6$H$_3$ |
| 8.013 | H | 2,4-F$_2$—C$_6$H$_3$ |
| 8.014 | H | 2,5-F$_2$—C$_6$H$_3$ |
| 8.015 | H | 2,6-F$_2$—C$_6$H$_3$ |
| 8.016 | H | 3,4-F$_2$—C$_6$H$_3$ |
| 8.017 | H | 3,5-F$_2$—C$_6$H$_3$ |
| 8.018 | H | 2-Cl—C$_6$H$_4$ |
| 8.019 | H | 3-Cl—C$_6$H$_4$ |
| 8.020 | H | 4-Cl—C$_6$H$_4$ |
| 8.021 | 3-Cl | 4-Cl—C$_6$H$_4$ |
| 8.022 | 4-Cl | 4-Cl—C$_6$H$_4$ |
| 8.023 | 6-Cl | 4-Cl—C$_6$H$_4$ |
| 8.024 | 4-F | 4-Cl—C$_6$H$_4$ |
| 8.025 | 4-OCH$_3$ | 4-Cl—C$_6$H$_4$ |
| 8.026 | 3-CH$_3$ | 4-Cl—C$_6$H$_4$ |
| 8.027 | 6-CH$_3$ | 4-Cl—C$_6$H$_4$ |
| 8.028 | H | 2,3-Cl$_2$—C$_6$H$_3$ |
| 8.029 | H | 2,4-Cl$_2$—C$_6$H$_3$ |
| 8.030 | H | 2,5-Cl$_2$—C$_6$H$_3$ |
| 8.031 | H | 2,6-Cl$_2$—C$_6$H$_3$ |
| 8.032 | H | 3,4-Cl$_2$—C$_6$H$_3$ |
| 8.033 | H | 3,5-Cl$_2$—C$_6$H$_3$ |
| 8.034 | H | 2,3,4-Cl$_3$—C$_6$H$_2$ |
| 8.035 | H | 2,3,5-Cl$_3$—C$_6$H$_2$ |
| 8.036 | H | 2,3,6-Cl$_3$—C$_6$H$_2$ |
| 8.037 | H | 2,4,5-Cl$_3$—C$_6$H$_2$ |
| 8.038 | H | 2,4,6-Cl$_3$—C$_6$H$_2$ |
| 8.039 | H | 3,4,5-Cl$_3$—C$_6$H$_2$ |
| 8.040 | H | 2-Br—C$_6$H$_4$ |
| 8.041 | H | 3-Br—C$_6$H$_4$ |
| 8.042 | H | 4-Br—C$_6$H$_4$ |
| 8.043 | H | 2,4-Br$_2$—C$_6$H$_3$ |
| 8.044 | H | 2-Br, 4-F—C$_6$H$_3$ |
| 8.045 | H | 2-Br, 4-Cl—C$_6$H$_3$ |
| 8.046 | H | 2-F, 4-Cl—C$_6$H$_3$ |
| 8.047 | H | 3-F, 4-Cl—C$_6$H$_3$ |
| 8.048 | H | 3-Cl, 5-F—C$_6$H$_3$ |
| 8.049 | H | 2-Cl, 4-F—C$_6$H$_3$ |
| 8.050 | H | 2-CN—C$_6$H$_4$ |
| 8.051 | H | 3-CN—C$_6$H$_4$ |
| 8.052 | H | 4-CN—C$_6$H$_4$ |
| 8.053 | H | 3-CN, 4-Cl—C$_6$H$_3$ |
| 8.054 | H | 4-NO$_2$—C$_6$H$_4$ |
| 8.055 | H | 4-H$_2$N—C(=S)—C$_6$H$_4$ |
| 8.056 | H | 2-CH$_3$—C$_6$H$_4$ |
| 8.057 | H | 3-CH$_3$—C$_6$H$_4$ |
| 8.058 | H | 4-CH$_3$—C$_6$H$_4$ |
| 8.059 | H | 2,4-(CH$_3$)$_2$—C$_6$H$_3$ |
| 8.060 | H | 2,5-(CH$_3$)$_2$—C$_6$H$_3$ |
| 8.061 | H | 2,5-(CH$_3$)$_2$—C$_6$H$_3$ |

TABLE A.8-continued

L.8

| No. | R¹ₙ | R² |
|---|---|---|
| 8.062 | H | 2,6-(CH₃)₂—C₆H₃ |
| 8.063 | H | 3,4-(CH₃)₂—C₆H₃ |
| 8.064 | H | 3,5-(CH₃)₂—C₆H₃ |
| 8.065 | H | 2,4,6-(CH₃)₃—C₆H₂ |
| 8.066 | H | 3,4,5-(CH₃)₃—C₆H₂ |
| 8.067 | H | 2-CH₃, 4-Cl—C₆H₃ |
| 8.068 | H | 2-Cl, 4-CH₃—C₆H₃ |
| 8.069 | H | 3-CH₃, 4-Cl—C₆H₃ |
| 8.070 | H | 3-Cl, 5-CH₃—C₆H₃ |
| 8.071 | H | 2-CN, 4-CH₃—C₆H₃ |
| 8.072 | H | 2-CH₃, 4-CN—C₆H₃ |
| 8.073 | H | 4-(C₂H₅)—C₆H₄ |
| 8.074 | H | 4-[C(CH₃)₃]—C₆H₄ |
| 8.075 | H | 3-(C₆H₅)—C₆H₄ |
| 8.076 | H | 4-(C₆H₅)—C₆H₄ |
| 8.077 | H | 2-CF₃—C₆H₄ |
| 8.078 | H | 3-CF₃—C₆H₄ |
| 8.079 | H | 4-CF₃—C₆H₄ |
| 8.080 | H | 3,5-(CF₃)₂—C₆H₃ |
| 8.081 | H | 2-Cl, 4-CF₃—C₆H₃ |
| 8.082 | H | 2-OCH₃—C₆H₄ |
| 8.083 | H | 3-OCH₃—C₆H₄ |
| 8.084 | H | 4-OCH₃—C₆H₄ |
| 8.085 | H | 2,4-(OCH₃)₂—C₆H₃ |
| 8.086 | H | 3,4-(OCH₃)₂—C₆H₃ |
| 8.087 | H | 2,5-(OCH₃)₂—C₆H₃ |
| 8.088 | H | 3,5-(OCH₃)₂—C₆H₃ |
| 8.089 | H | 3,4,5-(OCH₃)₃—C₆H₂ |
| 8.090 | H | 2-CH₃, 4-OCH₃—C₆H₃ |
| 8.091 | H | 2-Cl, 4-OCH₃—C₆H₃ |
| 8.092 | H | 4-OCF₃—C₆H₄ |
| 8.093 | H | 2-OCHF₂—C₆H₄ |
| 8.094 | H | 3-OCHF₂—C₆H₄ |
| 8.095 | H | 4-OCHF₂—C₆H₄ |
| 8.096 | H | 4-(OCF₂CHF₂)—C₆H₄ |
| 8.097 | H | 2-F, 4-OCHF₂—C₆H₃ |
| 8.098 | H | 4-(OCH₂CH₃)—C₆H₄ |
| 8.099 | H | 4-[OC(CH₃)₃]—C₆H₄ |
| 8.100 | H | 3-(CO₂CH₃)—C₆H₄ |
| 8.101 | H | 4-(CO₂CH₃)—C₆H₄ |
| 8.102 | H | 4-[CO₂C(CH₃)₃]—C₆H₄ |
| 8.103 | H | 2,3-[O—CH₂—O]—C₆H₃ |
| 8.104 | H | 3,4-[O—CH₂—O]—C₆H₃ |
| 8.105 | H | 3,4-[O—C(CH₃)₂—O]—C₆H₃ |
| 8.106 | H | 3,4-[O—CH₂CH₂—O]—C₆H₃ |
| 8.107 | H | 2,3-[(CH₂)₄]—C₆H₃ |
| 8.108 | H | 3,4-[(CH₂)₄]—C₆H₃ |
| 8.109 | H | 2,3-(CH=CH—CH=CH)—C₆H₃ |
| 8.110 | H | 3,4-(CH=CH—CH=CH)—C₆H₃ |
| 8.111 | H | CH₃ |
| 8.112 | H | CH₂CH₃ |
| 8.113 | H | CH₂CH₂CH₃ |
| 8.114 | H | C(CH₃)₂ |
| 8.115 | H | CH₂CH₂CH₂CH₃ |
| 8.116 | H | CHCH(CH₃)₂ |
| 8.117 | H | CH(CH₃)CH₂CH₃ |
| 8.118 | H | C(CH₃)₃ |
| 8.119 | H | cyclopropyl |
| 8.120 | H | cyclohexyl |
| 8.121 | H | 2-tetrahydrofuranyl |
| 8.122 | H | 3-tetrahydrofuranyl |
| 8.123 | H | 3-tetrahydrothienyl |

TABLE A.8-continued

L.8

| No. | R¹ₙ | R² |
|---|---|---|
| 8.124 | H | 2-1,3-dioxolanyl |
| 8.125 | H | 2-1,3-dioxanyl |
| 8.126 | H | 4-tetrahydropyranyl |

TABLE A.9

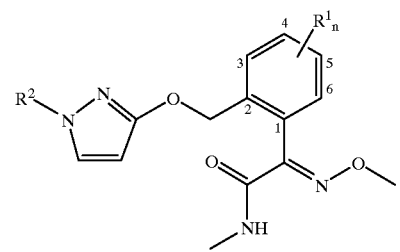

L.9

| No. | R¹ₙ | R² |
|---|---|---|
| 9.001 | H | C₆H₅ |
| 9.002 | 3-Cl | C₆H₅ |
| 9.003 | 4-Cl | C₆H₅ |
| 9.004 | 6-Cl | C₆H₅ |
| 9.005 | 4-F | C₆H₅ |
| 9.006 | 4-OCH₃ | C₆H₅ |
| 9.007 | 3-CH₃ | C₆H₅ |
| 9.008 | 6-CH₃ | C₆H₅ |
| 9.009 | H | 2-F—C₆H₄ |
| 9.010 | H | 3-F—C₆H₄ |
| 9.011 | H | 4-F—C₆H₄ |
| 9.012 | H | 2,3-F₂—C₆H₃ |
| 9.013 | H | 2,4-F₂—C₆H₃ |
| 9.014 | H | 2,5-F₂—C₆H₃ |
| 9.015 | H | 2,6-F₂—C₆H₃ |
| 9.016 | H | 3,4-F₂—C₆H₃ |
| 9.017 | H | 3,5-F₂—C₆H₃ |
| 9.018 | H | 2-Cl—C₆H₄ |
| 9.019 | H | 3-Cl—C₆H₄ |
| 9.020 | H | 4-Cl—C₆H₄ |
| 9.021 | 3-Cl | 4-Cl—C₆H₄ |
| 9.022 | 4-Cl | 4-Cl—C₆H₄ |
| 9.023 | 6-Cl | 4-Cl—C₆H₄ |
| 9.024 | 4-F | 4-Cl—C₆H₄ |
| 9.025 | 4-OCH₃ | 4-Cl—C₆H₄ |
| 9.026 | 3-CH₃ | 4-Cl—C₆H₄ |
| 9.027 | 6-CH₃ | 4-Cl—C₆H₄ |
| 9.028 | H | 2,3-Cl₂—C₆H₃ |
| 9.029 | H | 2,4-Cl₂—C₆H₃ |
| 9.030 | H | 2,5-Cl₂—C₆H₃ |
| 9.031 | H | 2,6-Cl₂—C₆H₃ |
| 9.032 | H | 3,4-Cl₂—C₆H₃ |
| 9.033 | H | 3,5-Cl₂—C₆H₃ |
| 9.034 | H | 2,3,4-Cl₃—C₆H₂ |
| 9.035 | H | 2,3,5-Cl₃—C₆H₂ |
| 9.036 | H | 2,3,6-Cl₃—C₆H₂ |
| 9.037 | H | 2,4,5-Cl₃—C₆H₂ |

TABLE A.9-continued

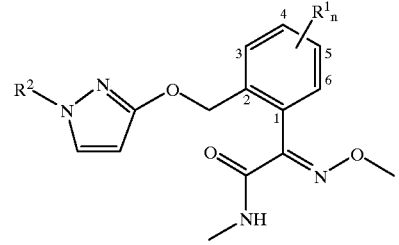

I.9

| No. | R¹ₙ | R² |
|---|---|---|
| 9.038 | H | 2,4,6-Cl₃—C₆H₂ |
| 9.039 | H | 3,4,5-Cl₃—C₆H₂ |
| 9.040 | H | 2-Br—C₆H₄ |
| 9.041 | H | 3-Br—C₆H₄ |
| 9.042 | H | 4-Br—C₆H₄ |
| 9.043 | H | 2,4-Br₂—C₆H₃ |
| 9.044 | H | 2-Br, 4-F—C₆H₃ |
| 9.045 | H | 2-Br, 4-Cl—C₆H₃ |
| 9.046 | H | 2-F, 4-Cl—C₆H₃ |
| 9.047 | H | 3-F, 4-Cl—C₆H₃ |
| 9.048 | H | 3-Cl, 5-F—C₆H₃ |
| 9.049 | H | 2-Cl, 4-F—C₆H₃ |
| 9.050 | H | 2-CN—C₆H₄ |
| 9.051 | H | 3-CN—C₆H₄ |
| 9.052 | H | 4-CN—C₆H₄ |
| 9.053 | H | 3-CN, 4-Cl—C₆H₃ |
| 9.054 | H | 4-NO₂—C₆H₄ |
| 9.055 | H | 4-H₂N—C(=S)—C₆H₄ |
| 9.056 | H | 2-CH₃—C₆H₄ |
| 9.057 | H | 3-CH₃—C₆H₄ |
| 9.058 | H | 4-CH₃—C₆H₄ |
| 9.059 | H | 2,4-(CH₃)₂—C₆H₃ |
| 9.060 | H | 2,5-(CH₃)₂—C₆H₃ |
| 9.061 | H | 2,5-(CH₃)₂—C₆H₃ |
| 9.062 | H | 2,6-(CH₃)₂—C₆H₃ |
| 9.063 | H | 3,4-(CH₃)₂—C₆H₃ |
| 9.064 | H | 3,5-(CH₃)₂—C₆H₃ |
| 9.065 | H | 2,4,6-(CH₃)₃—C₆H₂ |
| 9.066 | H | 3,4,5-(CH₃)₃—C₆H₂ |
| 9.067 | H | 2-CH₃, 4-Cl—C₆H₃ |
| 9.068 | H | 2-Cl, 4-CH₃—C₆H₃ |
| 9.069 | H | 3-CH₃, 4-Cl—C₆H₃ |
| 9.070 | H | 3-Cl, 5-CH₃—C₆H₃ |
| 9.071 | H | 2-CN, 4-CH₃—C₆H₃ |
| 9.072 | H | 2-CH₃, 4-CN—C₆H₃ |
| 9.073 | H | 4-(C₂H₅)—C₆H₄ |
| 9.074 | H | 4-[C(CH₃)₃]—C₆H₄ |
| 9.075 | H | 3-(C₆H₅)—C₆H₄ |
| 9.076 | H | 4-(C₆H₅)—C₆H₄ |
| 9.077 | H | 2-CF₃—C₆H₄ |
| 9.078 | H | 3-CF₃—C₆H₄ |
| 9.079 | H | 4-CF₃—C₆H₄ |
| 9.080 | H | 3,5-(CF₃)₂—C₆H₃ |
| 9.081 | H | 2-Cl, 4-CF₃—C₆H₃ |
| 9.082 | H | 2-OCH₃—C₆H₄ |
| 9.083 | H | 3-OCH₃—C₆H₄ |
| 9.084 | H | 4-OCH₃—C₆H₄ |
| 9.085 | H | 2,4-(OCH₃)₂—C₆H₃ |
| 9.086 | H | 3,4-(OCH₃)₂—C₆H₃ |
| 9.087 | H | 2,5-(OCH₃)₂—C₆H₃ |
| 9.088 | H | 3,5-(OCH₃)₂—C₆H₃ |
| 9.089 | H | 3,4,5-(OCH₃)₃—C₆H₂ |
| 9.090 | H | 2-CH₃, 4-OCH₃—C₆H₃ |
| 9.091 | H | 2-Cl, 4-OCH₃—C₆H₃ |
| 9.092 | H | 4-OCF₃—C₆H₄ |
| 9.093 | H | 2-OCHF₂—C₆H₄ |
| 9.094 | H | 3-OCHF₂—C₆H₄ |
| 9.095 | H | 4-OCHF₂—C₆H₄ |
| 9.096 | H | 4-(OCF₂CHF₂)—C₆H₄ |
| 9.097 | H | 2-F, 4-OCHF₂—C₆H₃ |
| 9.098 | H | 4-(OCH₂CH₃)—C₆H₄ |
| 9.099 | H | 4-[OC(CH₃)₃]—C₆H₄ |

TABLE A.9-continued

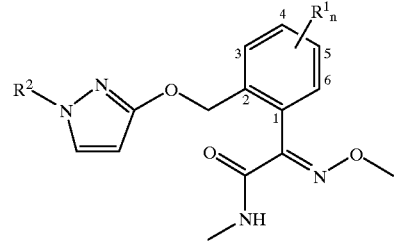

I.9

| No. | R¹ₙ | R² |
|---|---|---|
| 9.100 | H | 3-(CO₂CH₃)—C₆H₄ |
| 9.101 | H | 4-(CO₂CH₃)—C₆H₄ |
| 9.102 | H | 4-[CO₂C(CH₃)₃]—C₆H₄ |
| 9.103 | H | 2,3-[O—CH₂—O]—C₆H₃ |
| 9.104 | H | 3,4-[O—CH₂—O]—C₆H₃ |
| 9.105 | H | 3,4-[O—C(CH₃)₂—O]—C₆H₃ |
| 9.106 | H | 3,4-[O—CH₂CH₂—O]—C₆H₃ |
| 9.107 | H | 2,3-[(CH₂)₄]—C₆H₃ |
| 9.108 | H | 3,4-[(CH₂)₄]—C₆H₃ |
| 9.109 | H | 2,3-(CH=CH—CH=CH)—C₆H₃ |
| 9.110 | H | 3,4-(CH=CH—CH=CH)—C₆H₃ |
| 9.111 | H | CH₃ |
| 9.112 | H | CH₂CH₃ |
| 9.113 | H | CH₂CH₂CH₃ |
| 9.114 | H | C(CH₃)₂ |
| 9.115 | H | CH₂CH₂CH₂CH₃ |
| 9.116 | H | CHCH(CH₃)₂ |
| 9.117 | H | CH(CH₃)CH₂CH₃ |
| 9.118 | H | C(CH₃)₃ |
| 9.119 | H | cyclopropyl |
| 9.120 | H | cyclohexyl |
| 9.121 | H | 2-tetrahydrofuranyl |
| 9.122 | H | 3-tetrahydrofuranyl |
| 9.123 | H | 3-tetrahydrothienyl |
| 9.124 | H | 2-1,3-dioxolanyl |
| 9.125 | H | 2-1,3-dioxanyl |
| 9.126 | H | 4-tetrahydropyranyl |

TABLE A.10

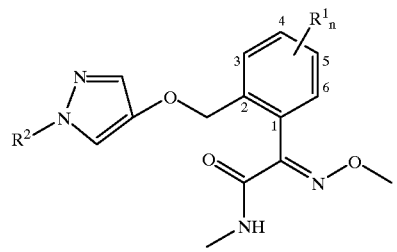

I.10

| No. | R¹ₙ | R² |
|---|---|---|
| 10.001 | H | C₆H₅ |
| 10.002 | 3-Cl | C₆H₅ |
| 10.003 | 4-Cl | C₆H₅ |
| 10.004 | 6-Cl | C₆H₅ |
| 10.005 | 4-F | C₆H₅ |
| 10.006 | 4-OCH₃ | C₆H₅ |
| 10.007 | 3-CH₃ | C₆H₅ |
| 10.008 | 6-CH₃ | C₆H₅ |
| 10.009 | H | 2-F—C₆H₄ |
| 10.010 | H | 3-F—C₆H₄ |
| 10.011 | H | 4-F—C₆H₄ |
| 10.012 | H | 2,3-F₂—C₆H₃ |
| 10.013 | H | 2,4-F₂—C₆H₃ |

TABLE A.10-continued

I.10

| No. | $R^1_n$ | $R^2$ |
|---|---|---|
| 10.014 | H | 2,5-F$_2$—C$_6$H$_3$ |
| 10.015 | H | 2,6-F$_2$—C$_6$H$_3$ |
| 10.016 | H | 3,4-F$_2$—C$_6$H$_3$ |
| 10.017 | H | 3,5-F$_2$—C$_6$H$_3$ |
| 10.018 | H | 2-Cl—C$_6$H$_4$ |
| 10.019 | H | 3-Cl—C$_6$H$_4$ |
| 10.020 | H | 4-Cl—C$_6$H$_4$ |
| 10.021 | 3-Cl | 4-Cl—C$_6$H$_4$ |
| 10.022 | 4-Cl | 4-Cl—C$_6$H$_4$ |
| 10.023 | 6-Cl | 4-Cl—C$_6$H$_4$ |
| 10.024 | 4-F | 4-Cl—C$_6$H$_4$ |
| 10.025 | 4-OCH$_3$ | 4-Cl—C$_6$H$_4$ |
| 10.026 | 3-CH$_3$ | 4-Cl—C$_6$H$_4$ |
| 10.027 | 6-CH$_3$ | 4-Cl—C$_6$H$_4$ |
| 10.028 | H | 2,3-Cl$_2$—C$_6$H$_3$ |
| 10.029 | H | 2,4-Cl$_2$—C$_6$H$_3$ |
| 10.030 | H | 2,5-Cl$_2$—C$_6$H$_3$ |
| 10.031 | H | 2,6-Cl$_2$—C$_6$H$_3$ |
| 10.032 | H | 3,4-Cl$_2$—C$_6$H$_3$ |
| 10.033 | H | 3,5-Cl$_2$—C$_6$H$_3$ |
| 10.034 | H | 2,3,4-Cl$_3$—C$_6$H$_2$ |
| 10.035 | H | 2,3,5-Cl$_3$—C$_6$H$_2$ |
| 10.036 | H | 2,3,6-Cl$_3$—C$_6$H$_2$ |
| 10.037 | H | 2,4,5-Cl$_3$—C$_6$H$_2$ |
| 10.038 | H | 2,4,6-Cl$_3$—C$_6$H$_2$ |
| 10.039 | H | 3,4,5-Cl$_3$—C$_6$H$_2$ |
| 10.040 | H | 2-Br—C$_6$H$_4$ |
| 10.041 | H | 3-Br—C$_6$H$_4$ |
| 10.042 | H | 4-Br—C$_6$H$_4$ |
| 10.043 | H | 2,4-Br$_2$—C$_6$H$_3$ |
| 10.044 | H | 2-Br, 4-F—C$_6$H$_3$ |
| 10.045 | H | 2-Br, 4-Cl—C$_6$H$_3$ |
| 10.046 | H | 2-F, 4-Cl—C$_6$H$_3$ |
| 10.047 | H | 3-F, 4-Cl—C$_6$H$_3$ |
| 10.048 | H | 3-Cl, 5-F—C$_6$H$_3$ |
| 10.049 | H | 2-Cl, 4-F—C$_6$H$_3$ |
| 10.050 | H | 2-CN—C$_6$H$_4$ |
| 10.051 | H | 3-CN—C$_6$H$_4$ |
| 10.052 | H | 4-CN—C$_6$H$_4$ |
| 10.053 | H | 3-CN, 4-Cl—C$_6$H$_3$ |
| 10.054 | H | 4-NO$_2$—C$_6$H$_4$ |
| 10.055 | H | 4-H$_2$N—C(=S)—C$_6$H$_4$ |
| 10.056 | H | 2-CH$_3$—C$_6$H$_4$ |
| 10.057 | H | 3-CH$_3$—C$_6$H$_4$ |
| 10.058 | H | 4-CH$_3$—C$_6$H$_4$ |
| 10.059 | H | 2,4-(CH$_3$)$_2$—C$_6$H$_3$ |
| 10.060 | H | 2,5-(CH$_3$)$_2$—C$_6$H$_3$ |
| 10.061 | H | 2,5-(CH$_3$)$_2$—C$_6$H$_3$ |
| 10.062 | H | 2,6-(CH$_3$)$_2$—C$_6$H$_3$ |
| 10.063 | H | 3,4-(CH$_3$)$_2$—C$_6$H$_3$ |
| 10.064 | H | 3,5-(CH$_3$)$_2$—C$_6$H$_3$ |
| 10.065 | H | 2,4,6-(CH$_3$)$_3$—C$_6$H$_2$ |
| 10.066 | H | 3,4,5-(CH$_3$)$_3$—C$_6$H$_2$ |
| 10.067 | H | 2-CH$_3$, 4-Cl—C$_6$H$_3$ |
| 10.068 | H | 2-Cl, 4-CH$_3$—C$_6$H$_3$ |
| 10.069 | H | 3-CH$_3$, 4-Cl—C$_6$H$_3$ |
| 10.070 | H | 3-Cl, 5-CH$_3$—C$_6$H$_3$ |
| 10.071 | H | 2-CN, 4-CH$_3$—C$_6$H$_3$ |
| 10.072 | H | 2-CH$_3$, 4-CN—C$_6$H$_3$ |
| 10.073 | H | 4-(C$_2$H$_5$)—C$_6$H$_4$ |
| 10.074 | H | 4-[C(CH$_3$)$_3$]—C$_6$H$_4$ |
| 10.075 | H | 3-(C$_6$H$_5$)—C$_6$H$_4$ |
| 10.076 | H | 4-(C$_6$H$_5$)—C$_6$H$_4$ |
| 10.077 | H | 2-CF$_3$—C$_6$H$_4$ |
| 10.078 | H | 3-CF$_3$—C$_6$H$_4$ |
| 10.079 | H | 4-CF$_3$—C$_6$H$_4$ |
| 10.080 | H | 3,5-(CF$_3$)$_2$—C$_6$H$_3$ |
| 10.081 | H | 2-Cl, 4-CF$_3$—C$_6$H$_3$ |
| 10.082 | H | 2-OCH$_3$—C$_6$H$_4$ |
| 10.083 | H | 3-OCH$_3$—C$_6$H$_4$ |
| 10.084 | H | 4-OCH$_3$—C$_6$H$_4$ |
| 10.085 | H | 2,4-(OCH$_3$)$_2$—C$_6$H$_3$ |
| 10.086 | H | 3,4-(OCH$_3$)$_2$—C$_6$H$_3$ |
| 10.087 | H | 2,5-(OCH$_3$)$_2$—C$_6$H$_3$ |
| 10.088 | H | 3,5-(OCH$_3$)$_2$—C$_6$H$_3$ |
| 10.089 | H | 3,4,5-(OCH$_3$)$_3$—C$_6$H$_2$ |
| 10.090 | H | 2-CH$_3$, 4-OCH$_3$—C$_6$H$_3$ |
| 10.091 | H | 2-Cl, 4-OCH$_3$—C$_6$H$_3$ |
| 10.092 | H | 4-OCF$_3$—C$_6$H$_4$ |
| 10.093 | H | 2-OCHF$_2$—C$_6$H$_4$ |
| 10.094 | H | 3-OCHF$_2$—C$_6$H$_4$ |
| 10.095 | H | 4-OCHF$_2$—C$_6$H$_4$ |
| 10.096 | H | 4-(OCF$_2$CHF$_2$)—C$_6$H$_4$ |
| 10.097 | H | 2-F, 4-OCHF$_2$—C$_6$H$_3$ |
| 10.098 | H | 4-(OCH$_2$CH$_3$)—C$_6$H$_4$ |
| 10.099 | H | 4-[OC(CH$_3$)$_3$]—C$_6$H$_4$ |
| 10.100 | H | 3-(CO$_2$CH$_3$)—C$_6$H$_4$ |
| 10.101 | H | 4-(CO$_2$CH$_3$)—C$_6$H$_4$ |
| 10.102 | H | 4-[CO$_2$C(CH$_3$)$_3$]—C$_6$H$_4$ |
| 10.103 | H | 2,3-[O—CH$_2$—O]—C$_6$H$_3$ |
| 10.104 | H | 3,4-[O—CH$_2$—O]—C$_6$H$_3$ |
| 10.105 | H | 3,4-[O—C(CH$_3$)$_2$—O]—C$_6$H$_3$ |
| 10.106 | H | 3,4-[O—CH$_2$CH$_2$—O]—C$_6$H$_3$ |
| 10.107 | H | 2,3-[(CH$_2$)$_4$]—C$_6$H$_3$ |
| 10.108 | H | 3,4-[(CH$_2$)$_4$]—C$_6$H$_3$ |
| 10.109 | H | 2,3-(CH=CH—CH=CH)—C$_6$H$_3$ |
| 10.110 | H | 3,4-(CH=CH—CH=CH)—C$_6$H$_3$ |
| 10.111 | H | CH$_3$ |
| 10.112 | H | CH$_2$CH$_3$ |
| 10.113 | H | CH$_2$CH$_2$CH$_3$ |
| 10.114 | H | C(CH$_3$)$_2$ |
| 10.115 | H | CH$_2$CH$_2$CH$_2$CH$_3$ |
| 10.116 | H | CHCH(CH$_3$)$_2$ |
| 10.117 | H | CH(CH$_3$)CH$_2$CH$_3$ |
| 10.118 | H | C(CH$_3$)$_3$ |
| 10.119 | H | cyclopropyl |
| 10.120 | H | cyclohexyl |
| 10.121 | H | 2-tetrahydrofuranyl |
| 10.122 | H | 3-tetrahydrofuranyl |
| 10.123 | H | 3-tetrahydrothienyl |
| 10.124 | H | 2-1,3-dioxolanyl |
| 10.125 | H | 2-1,3-dioxanyl |
| 10.126 | H | 4-tetrahydropyranyl |

TABLE A.11

I.11

| No. | $R_n^1$ | $R^2$ |
|---|---|---|
| 11.001 | H | $C_6H_5$ |
| 11.002 | 3-Cl | $C_6H_5$ |
| 11.003 | 4-Cl | $C_6H_5$ |
| 11.004 | 6-Cl | $C_6H_5$ |
| 11.005 | 4-F | $C_6H_5$ |
| 11.006 | 4-OCH$_3$ | $C_6H_5$ |
| 11.007 | 3-CH$_3$ | $C_6H_5$ |
| 11.008 | 6-CH$_3$ | $C_6H_5$ |
| 11.009 | H | 2-F—$C_6H_4$ |
| 11.010 | H | 3-F—$C_6H_4$ |
| 11.011 | H | 4-F—$C_6H_4$ |
| 11.012 | H | 2,3-F$_2$—$C_6H_3$ |
| 11.013 | H | 2,4-F$_2$—$C_6H_3$ |
| 11.014 | H | 2,5-F$_2$—$C_6H_3$ |
| 11.015 | H | 2,6-F$_2$—$C_6H_3$ |
| 11.016 | H | 3,4-F$_2$—$C_6H_3$ |
| 11.017 | H | 3,5-F$_2$—$C_6H_3$ |
| 11.018 | H | 2-Cl—$C_6H_4$ |
| 11.019 | H | 3-Cl—$C_6H_4$ |
| 11.020 | H | 4-Cl—$C_6H_4$ |
| 11.021 | 3-Cl | 4-Cl—$C_6H_4$ |
| 11.022 | 4-Cl | 4-Cl—$C_6H_4$ |
| 11.023 | 6-Cl | 4-Cl—$C_6H_4$ |
| 11.024 | 4-F | 4-Cl—$C_6H_4$ |
| 11.025 | 4-OCH$_3$ | 4-Cl—$C_6H_4$ |
| 11.026 | 3-CH$_3$ | 4-Cl—$C_6H_4$ |
| 11.027 | 6-CH$_3$ | 4-Cl—$C_6H_4$ |
| 11.028 | H | 2,3-Cl$_2$—$C_6H_3$ |
| 11.029 | H | 2,4-Cl$_2$—$C_6H_3$ |
| 11.030 | H | 2,5-Cl$_2$—$C_6H_3$ |
| 11.031 | H | 2,6-Cl$_2$—$C_6H_3$ |
| 11.032 | H | 3,4-Cl$_2$—$C_6H_3$ |
| 11.033 | H | 3,5-Cl$_2$—$C_6H_3$ |
| 11.034 | H | 2,3,4-Cl$_3$—$C_6H_2$ |
| 11.035 | H | 2,3,5-Cl$_3$—$C_6H_2$ |
| 11.036 | H | 2,3,6-Cl$_3$—$C_6H_2$ |
| 11.037 | H | 2,4,5-Cl$_3$—$C_6H_2$ |
| 11.038 | H | 2,4,6-Cl$_3$—$C_6H_2$ |
| 11.039 | H | 3,4,5-Cl$_3$—$C_6H_2$ |
| 11.040 | H | 2-Br—$C_6H_4$ |
| 11.041 | H | 3-Br—$C_6H_4$ |
| 11.042 | H | 4-Br—$C_6H_4$ |
| 11.043 | H | 2,4-Br$_2$—$C_6H_3$ |
| 11.044 | H | 2-Br, 4-F—$C_6H_3$ |
| 11.045 | H | 2-Br, 4-Cl—$C_6H_3$ |
| 11.046 | H | 2-F, 4-Cl—$C_6H_3$ |
| 11.047 | H | 3-F, 4-Cl—$C_6H_3$ |
| 11.048 | H | 3-Cl, 5-F—$C_6H_3$ |
| 11.049 | H | 2-Cl, 4-F—$C_6H_3$ |
| 11.050 | H | 2-CN—$C_6H_4$ |
| 11.051 | H | 3-CN—$C_6H_4$ |
| 11.052 | H | 4-CN—$C_6H_4$ |
| 11.053 | H | 3-CN, 4-Cl—$C_6H_3$ |
| 11.054 | H | 4-NO$_2$—$C_6H_4$ |
| 11.055 | H | 4-H$_2$N—C(=S)—$C_6H_4$ |
| 11.056 | H | 2-CH$_3$—$C_6H_4$ |
| 11.057 | H | 3-CH$_3$—$C_6H_4$ |
| 11.058 | H | 4-CH$_3$—$C_6H_4$ |
| 11.059 | H | 2,4-(CH$_3$)$_2$—$C_6H_3$ |
| 11.060 | H | 2,5-(CH$_3$)$_2$—$C_6H_3$ |
| 11.061 | H | 2,5-(CH$_3$)$_2$—$C_6H_3$ |
| 11.062 | H | 2,6-(CH$_3$)$_2$—$C_6H_3$ |
| 11.063 | H | 3,4-(CH$_3$)$_2$—$C_6H_3$ |
| 11.064 | H | 3,5-(CH$_3$)$_2$—$C_6H_3$ |
| 11.065 | H | 2,4,6-(CH$_3$)$_3$—$C_6H_2$ |
| 11.066 | H | 3,4,5-(CH$_3$)$_3$—$C_6H_2$ |
| 11.067 | H | 2-CH$_3$, 4-Cl—$C_6H_3$ |
| 11.068 | H | 2-Cl, 4-CH$_3$—$C_6H_3$ |
| 11.069 | H | 3-CH$_3$, 4-Cl—$C_6H_3$ |
| 11.070 | H | 3-Cl, 5-CH$_3$—$C_6H_3$ |
| 11.071 | H | 2-CN, 4-CH$_3$—$C_6H_3$ |
| 11.072 | H | 2-CH$_3$, 4-CN—$C_6H_3$ |
| 11.073 | H | 4-(C$_2$H$_5$)—$C_6H_4$ |
| 11.074 | H | 4-[C(CH$_3$)$_3$]—$C_6H_4$ |
| 11.075 | H | 3-(C$_6$H$_5$)—$C_6H_4$ |
| 11.076 | H | 4-(C$_6$H$_5$)—$C_6H_4$ |
| 11.077 | H | 2-CF$_3$—$C_6H_4$ |
| 11.078 | H | 3-CF$_3$—$C_6H_4$ |
| 11.079 | H | 4-CF$_3$—$C_6H_4$ |
| 11.080 | H | 3,5-(CF$_3$)$_2$—$C_6H_3$ |
| 11.081 | H | 2-Cl, 4-CF$_3$—$C_6H_3$ |
| 11.082 | H | 2-OCH$_3$—$C_6H_4$ |
| 11.083 | H | 3-OCH$_3$—$C_6H_4$ |
| 11.084 | H | 4-OCH$_3$—$C_6H_4$ |
| 11.085 | H | 2,4-(OCH$_3$)$_2$—$C_6H_3$ |
| 11.086 | H | 3,4-(OCH$_3$)$_2$—$C_6H_3$ |
| 11.087 | H | 2,5-(OCH$_3$)$_2$—$C_6H_3$ |
| 11.088 | H | 3,5-(OCH$_3$)$_2$—$C_6H_3$ |
| 11.089 | H | 3,4,5-(OCH$_3$)$_3$—$C_6H_2$ |
| 11.090 | H | 2-CH$_3$, 4-OCH$_3$—$C_6H_3$ |
| 11.091 | H | 2-Cl, 4-OCH$_3$—$C_6H_3$ |
| 11.092 | H | 4-OCF$_3$—$C_6H_4$ |
| 11.093 | H | 2-OCHF$_2$—$C_6H_4$ |
| 11.094 | H | 3-OCHF$_2$—$C_6H_4$ |
| 11.095 | H | 4-OCHF$_2$—$C_6H_4$ |
| 11.096 | H | 4-(OCF$_2$CHF$_2$)—$C_6H_4$ |
| 11.097 | H | 2-F, 4-OCHF$_2$—$C_6H_3$ |
| 11.098 | H | 4-(OCH$_2$CH$_3$)—$C_6H_4$ |
| 11.099 | H | 4-[OC(CH$_3$)$_3$]—$C_6H_4$ |
| 11.100 | H | 3-(CO$_2$CH$_3$)—$C_6H_4$ |
| 11.101 | H | 4-(CO$_2$CH$_3$)—$C_6H_4$ |
| 11.102 | H | 4-[CO$_2$C(CH$_3$)$_3$]—$C_6H_4$ |
| 11.103 | H | 2,3-[O—CH$_2$—O]—$C_6H_3$ |
| 11.104 | H | 3,4-[O—CH$_2$—O]—$C_6H_3$ |
| 11.105 | H | 3,4-[O—C(CH$_3$)$_2$—O]—$C_6H_3$ |
| 11.106 | H | 3,4-[O—CH$_2$CH$_2$—O]—$C_6H_3$ |
| 11.107 | H | 2,3-[(CH$_2$)$_4$]—$C_6H_3$ |
| 11.108 | H | 3,4-[(CH$_2$)$_4$]—$C_6H_3$ |
| 11.109 | H | 2,3-(CH=CH$_2$—CH=CH)—$C_6H_3$ |
| 11.110 | H | 3,4-(CH=CH—CH=CH)—$C_6H_3$ |
| 11.111 | H | CH$_3$ |
| 11.112 | H | CH$_2$CH$_3$ |
| 11.113 | H | CH$_2$CH$_2$CH$_3$ |
| 11.114 | H | C(CH$_3$)$_2$ |
| 11.115 | H | CH$_2$CH$_2$CH$_2$CH$_3$ |
| 11.116 | H | CHCH(CH$_3$)$_2$ |
| 11.117 | H | CH(CH$_3$)CH$_2$CH$_3$ |
| 11.118 | H | C(CH$_3$)$_3$ |
| 11.119 | H | cyclopropyl |
| 11.120 | H | cyclohexyl |
| 11.121 | H | 2-tetrahydrofuranyl |
| 11.122 | H | 3-tetrahydrofuranyl |
| 11.123 | H | 3-tetrahydrothienyl |

TABLE A.11-continued

I.11

R²—N(triazole)—O—CH₂—[phenyl(R¹ₙ)]—C(=N—OMe)—C(=O)—NH—Me

| No. | Rₙ¹ | R² |
|---|---|---|
| 11.124 | H | 2-1,3-dioxolanyl |
| 11.125 | H | 2-1,3-dioxanyl |
| 11.126 | H | 4-tetrahydropyranyl |

TABLE A.12

I(X = O)

R²—Y—X—[phenyl(R¹)ₙ]—C(=O)—... —N—OMe, NH-Me

| No. | R²—Y |
|---|---|
| 12.001 | 1-(2-pyridyl)pyrazol-4-yl |
| 12.002 | 1-(3,5-di-trifluoromethyl-2-pyridyl)pyrazol-4-yl |
| 12.003 | 1-(5-chloro-3-trifluoromethyl-2-pyridyl)pyrazol-4-yl |
| 12.004 | 1-(6-trifluoromethyl-2-pyridyl)pyrazol-4-yl |
| 12.005 | 1-(4-trifluoromethyl-6-methyl-2-pyridyl)pyrazol-4-yl |
| 12.006 | 1-(1-ethyl-2-pyridyl)pyrazol-4-yl |
| 12.007 | 1-(3-pyridyl)pyrazol-4-yl |
| 12.008 | 1-(6-methyl-3-pyridyl)pyrazol-4-yl |
| 12.009 | 1-(4-pyridyl)pyrazol-4-yl |
| 12.010 | 1-(2,6-dimethyl-4-pyridyl)pyrazol-4-yl |
| 12.011 | 1-(6-methyl-3-pyridazinyl)pyrazol-4-yl |
| 12.012 | 1-(6-chloro-3-pyridazinyl)pyrazol-4-yl |
| 12.013 | 1-(5-methoxycarbonyl-4-trifluoromethyl-2-pyrimidyl)-pyrazol-4-yl |
| 12.014 | 1-(4-trifluoromethyl-2-pyrimidyl)pyrazol-4-yl |
| 12.015 | 1-(5-chloro-2-pyrimidyl)pyrazol-4-yl |
| 12.016 | 1-(6-trifluoromethyl-4-pyrimidyl)pyrazol-4-yl |
| 12.017 | 1-(5-ethyl-2-pyrimidyl)pyrazol-4-yl |
| 12.018 | 1-(2-methyl-5-pyrimidyl)pyrazol-4-yl |
| 12.019 | 1-(5-methyl-2-pyrazinyl)pyrazol-4-yl |
| 12.020 | 1-(5-chloro-2-pyrazinyl)pyrazol-4-yl |
| 12.021 | 1-(4-methyl-2-thiazolyl)pyrazol-4-yl |
| 12.022 | 1-(5-methyl-3-thiazolyl)pyrazol-4-yl |
| 12.023 | 1-(5-cyclopropyl-3-isoxazolyl)pyrazol-4-yl |
| 12.024 | 1-(5-phenyl-3-isoxazolyl)pyrazol-4-yl |
| 12.025 | 4-methylpyrazol-1-yl |
| 12.026 | 4-chloropyrazol-1-yl |
| 12.027 | 3,5-dimethylpyrazol-1-yl |
| 12.028 | 4-phenylpyrazol-1-yl |
| 12.029 | 4-(3-methyl-5-isoxazolyl)pyrazol-1-yl |
| 12.030 | 4-(3-tert-butyl-5-isoxazolyl)pyrazol-1-yl |
| 12.031 | 4-(3-phenyl-5-isoxazolyl)pyrazol-1-yl |
| 12.032 | 4-(3-methyl-5-isoxazolyl)thiazol-2-yl |
| 12.033 | 4-(3-isoxazolyl-5-isoxazolyl)thiazol-2-yl |
| 12.034 | 4-(2-methyl-4-thiazolyl)thiazol-2-yl |
| 12.035 | 4-(2-hexyl-4-thiazolyl)thiazol-2-yl |
| 12.036 | 2-(2-methyl-4-thiazolyl)-5-methylthiazol-4-yl |

TABLE A.12-continued

I(X = O)

| No. | R²—Y |
|---|---|
| 12.037 | 4-(3-methyl-5-isoxazolyl)oxazol-2-yl |
| 12.038 | 4-(3-methyl-4-thiazolyl)oxazol-2-yl |
| 12.039 | 4-(2-cyclopropyl-4-thiazolyl)oxazol-2-yl |
| 12.040 | 4-(1-methoxyiminoethyl)thiazol-2-yl |
| 12.041 | 4-(1-ethoxyiminoethyl)thiazol-2-yl |
| 12.042 | 4-(1-prop-2-enyloxyiminoethyl)thiazol-2-yl |
| 12.043 | 4-(1-tert-butoxyiminoethyl)thiazol-2-yl |
| 12.044 | 4-(1-methoxyiminopropyl)thiazol-2-yl |
| 12.045 | 4-(1-methoxyiminoethyl)-5-methylthiazol-2-yl |
| 12.046 | 4-(1-prop-2-enyloxyiminoethyl)-5-methylthiazol-2-yl |

The starting compounds IA can be prepared, for example, as described below (Examples 1 to 3) from the easily accessible methyl E-2-methoxyimino-2-[(2-methylphenoxymethyl)phenyl]acetate (cf. EP 493 711) by aminolysis with methylamine and subsequent cleavage with boron trichloride or hydrogen bromide.

The procedures represented in the synthesis examples below were utilized with appropriate modification of the starting compounds for preparing further compounds I. The compounds thus obtained are listed in the Tables below with physical data.

EXAMPLE 1

E-2-Methoxyimino-2-[(2-methylphenoxymethyl)phenyl]-N-methylacetamide 250 g of methyl E-2-methoxyimino-2-[(2-methylphenoxymethyl)phenyl]acetate are suspended in 1 l of 40% strength aqueous methylamine solution and heated to 40° C. for 4 h. After cooling to room temperature (20° C.), the solid is filtered off with suction, washed several times with water and dried at 50° C. 229.8 g of the title compound are obtained as colorless crystals.

M.p.: 109–112° C.

$^1$H-NMR (CDCl$_3$, δ in ppm): 2.20 (s, 3H); 2.85 (d, 3H); 3.95 (s, 3H); 4.90 (s, 2H); 6.7 (NH); 6.8–7.6 (m, 8H).

EXAMPLE 2

E-2-Methoxyimino-2-[(2-chloromethyl)phenyl]-N-methylacetamide 2 g of E-2-methoxyimino-2-[(2-methylphenoxymethyl) phenyl]-N-methylacetamide from Example 1 are initially introduced into 30 ml of anhydrous dichloromethane at 10° C. 9.4 g of boron trichloride (as a 1-molar solution in n-hexane) are added dropwise to this solution, it is heated to reflux for 1.5 h and cooled to 10° C., a further 9.4 g of boron trichloride are added and the mixture is stirred overnight at room temperature (20° C.). After dropwise addition of 8.2 g of methanol, the batch is concentrated in a rotary evaporator. The residue is taken up in 100 ml of dichloromethane, and the solution is washed with 5% sodium hydroxide solution and then with water. The organic phase is finally dried over sodium sulfate. After stripping off the solvent, 1.2 g of the title compound remain as an oil.

$^1$H-NMR (CDCl$_3$, δ in ppm): 2.95 (d, 3H); 3.90 (s, 3H); 4.45 (s, 2H); 6.8 (NH); 7.1–7.6 (m, 4H).

EXAMPLE 3

E-2-Methoxyimino-2-[(2-bromomethyl)phenyl]-N-methylacetamide 10 g of E-2-methoxyimino-2-[(2-methylphenoxymethyl)phenyl]-N-methylacetamide from Example 1 are initially introduced into 50 ml of anhydrous dichloromethane. Hydrogen bromide is introduced into the solution up to the saturation concentration (about 9 g of HBr). After stirring at room temperature for 68 h, the starting material is completely reacted. After addition of a further 50 ml of dichloromethane, the mixture is worked up as in Example 2. 7.0 g of the title compound remain as an oil, which crystallizes completely on allowing to stand.

M.p.: 128–129° C.

$^1$H-NMR (CDCl$_3$, δ in ppm): 2.95 (d, 3H); 3.95 (s, 3H); 4.35 (s, 2H); 6.85 (NH); 7.1–7.5 (m, 4H).

EXAMPLE 4

Methyl E-2-methoxyimino-2-[(2-[5-(4-chlorophenyl)isoxazol-3-yl]oxymethyl)phenyl] acetate 1.8 g of 3-hydroxy-5-(4-chlorophenyl)isoxazole are dissolved in 10 ml of dimethylformamide. 1.6 g of finely powdered potassium carbonate and 2.8 g of methyl E-2-methoxyimino-2-[(2-bromomethyl)phenyl]acetate are added to this solution. The reaction mixture is stirred overnight at room temperature and then poured onto 50 ml of water for working up. After extracting three times with methyl tert-butyl ether, the combined organic phases are dried over sodium sulfate. After stripping off the solvent, the residue is triturated with methyl tert-butyl ether. After filtering off with suction, 1.8 g of the title compound remain.

M.p.: 155–157° C.

$^1$H-NMR (CDCl$_3$, δ in ppm):

3.85 (s, 3H); 4.06 (s, 3H); 5.2 (s, 2H); 6.1 (s, 1H); 7.2–7.7 (m, 8H).

EXAMPLE 5

E-2-Methoxyimino-2-[(2-[5-(4-chlorophenyl)isoxazol-3-yl]oxymethyl)phenyl]-N-methylacetamide 1.0g of the methyl ester from Example 4 are dissolved in 15 ml of tetrahydrofuran and treated with 1 ml of 40% strength aqueous methylamine solution. The mixture is stirred overnight at room temperature and concentrated, and the residue is taken up in 50 ml of methyl tert-butyl ether. The organic phase is extracted with water, dried over sodium sulfate and finally evaporated to dryness. 0.9 g of the title compound remains as a colorless solid.

M.p.: 195–198° C.

$^1$H-NMR (CDCl$_3$, δ in ppm): 2.95 (d, 3H); 3.95 (s, 3H); 5.2 (s, 2H); 6.15 (s, 1H); 6.85 (NH); 7.2–7.8 (m, 8H).

EXAMPLE 6

E-2-Methoxyimino-2-[(2-[5-(4-trifluoromethylphenyl)-1,3,4-oxadiazol-2-yl]thiomethyl)phenyl]-N-methylacetamide 1.35 g of 5-(4-trifluoromethylphenyl)-2-mercapto-1,3,4-oxadiazole and 1.43 g of the bromomethyl compound from Example 3 are dissolved in 30 ml of acetone. After addition of 0.8 g of finely powdered potassium carbonate, the batch is stirred overnight at RT. The solid is filtered off with suction and the filtrate is evaporated to dryness. The residue which remains is triturated with n-pentane and filtered off with suction. 2.2 g of the title compound remain as a colorless solid.

M.p.: 128–129° C.

$^1$H-NMR (CDCl$_3$, δ in ppm): [lacuna]

EXAMPLE 7

E-2-Methoxyimino-2-[(2-[1-(4-chloro-2-methylphenyl)pyrazol-4-yl]oxymethyl)phenyl]-N-methylacetamide 1.05 g of 1-(4-chloro-2-methylphenyl)-4-hydroxypyrazole are initially introduced into 20 ml of dichloromethane. After addition of 50 mg of tetra-n-butylammonium iodide and a solution of 1.43 g of bromomethyl compound from Example 3 in 10 ml of dichloromethane, the reaction is started using 20 ml of 10% strength sodium hydroxide solution. The two-phase system is vigorously stirred until conversion of the bromomethyl compound is complete. The organic phase is separated off and extracted a further two times with dichloromethane, and the combined organic phases are dried over sodium sulfate. The crude product which remains after stripping off the solvent is taken up in 70 ml of isopropyl ether/acetone (5:2, v/v). Insoluble constituents are decanted off, the liquid is concentrated and the residue is chromatographed on silica gel (eluent toluene/ethyl acetate, 9:1).

TABLE 1

[Structure: benzene ring with (R¹)ₙ substituent, bearing a -CH₂-X-Y-R² group and a -C(=N-OCH₃)-C(=O)-NH-CH₃ group]

| No. | Rₙ¹ | X | R²—Y | M.p. [° C.]/IR [cm⁻¹]/¹H—NMR [ppm] |
|---|---|---|---|---|
| 1 | H | O | 5-Methylisoxazol-3-yl | 112–115 |
| 2 | H | O | 5-(4-chlorophenyl)isoxazol-3-yl | 195–198 |
| 3 | H | O | 3-Phenyl-1,2,4-thiadiazol-5-yl | 3230,1652,1588,1462,1351 |
| 5 | H | S | 5-(4-chlorophenyl)-1,3,4-oxadiazol-2-yl | 186–188 |
| 6 | H | S | 5-(4-Methylphenyl)-1,3,4-oxadiazol-2-yl | 176–177 |
| 7 | H | O | 4-(4-Fluorophenyl)-1,3-thiazol-2-yl | 118–120 |
| 8 | H | O | 4-(4-chlorophenyl)-1,3-thiazol-2-yl | 121–123 |
| 9 | H | O | 4-(2,4-Dichlorophenyl)-1,3-thiazol-2-yl | 120–121 |
| 10 | H | O | 1-Phenyl-1,2,4-triazol-3-yl | 1667,1545,1329,1069,1038 |
| 11 | H | O | 1-Phenylpyrazol-4-yl | 1667,1597,1580,1503,1400, 1357,1035 |
| 12 | H | O | 1-(4-Fluorophenyl)pyrazol-4-yl | 1667,1514,1403,1358,1227, 1033 |
| 14 | H | O | 1-(4-Trifluoromethylphenyl)pyrazol-4-yl | 98–100 |
| 15 | H | O | 1-(4-Cyanophenyl)pyrazol-4-yl | 130–135 |
| 16 | H | O | 1-(4-Methylphenyl)pyrazol-4-yl | 102–105 |
| 17 | H | O | 1-(4-Chlorophenyl)pyrazol-4-yl | 111–114 |
| 18 | H | O | 1-(2,4-Dichlorophenyl)pyrazol-4-yl | 104–106 |
| 19 | H | O | 5-Trifluoromethylisooxazol-3-yl [sic] | 97–98 |
| 20 | H | O | 5-Phenylisoxazol-3-yl | 121–123 |
| 21 | H | O | 1-(6-Chloro-2-pyridyl)-1,2,4-triazol-3-yl | 153–155 |
| 22 | H | O | 1-(2-Chloro-4-methylphenyl)pyrazol-4-yl | |
| 23 | H | O | 1-(2,4-Dichlorophenyl)pyrazol-3-yl | 99–102 |
| 24 | H | O | 1-(4-Chlorophenyl)pyrazol-3-yl | 110–122 |
| 25 | H | O | 1-(3-Chlorophenyl)pyrazol-3-yl | 1670,1596,1547,1475,1036 |
| 26 | H | O | 1-(4-Fluorophenyl)pyrazol-3-yl | 80–83 |
| 27 | H | d | 1-(4-Methylphenyl)pyrazol-3-yl | 3379,1662,1540,1353,1033 |
| 28 | H | S | 1-Methylimidazol-2-yl | 124–126 |
| 29 | H | S | 4-Methyl-1,2,4-triazol-3-yl | 131–135 |
| 30 | H | S | 5-(4-Trifluoromethylphenyl)-1,3,4-oxadiazol-2-yl | 128–129 |
| 31 | H | O | 4-Acetylthiazol-2-yl | 83–85 |
| 32 | H | O | 4-Isopropylthiazol-2-yl | 73–74 |
| 33 | H | O | 4-Isobutylthiazol-2-yl | 51–52 |
| 34 | H | O | 4-Phenylthiazol-2-yl | 128–130 |
| 35 | H | O | 4-(2-Methylphenyl)thiazol-2-yl | 88–89 |
| 36 | H | O | 4-(3-Methylphenyl)thiazol-2-yl | 91–92 |
| 37 | H | O | 4-(4-Methylphenyl)thiazol-2-yl | 118–119 |
| 38 | H | O | 4-(2-Methoxyphenyl)thiazol-2-yl | 1671,1533,1487,1462,1244, 1185,1036 |
| 39 | H | O | 4-(3-Methoxyphenyl)thiazol-2-yl | 113–114 |
| 40 | H | O | 4-(4-Methoxyphenyl)thiazol-2-yl | 105–106 |
| 41 | H | O | 4-(3-Bromophenyl)thiazol-2-yl | 110–112 |
| 42 | H | O | 4-(4-Bromophenyl)thiazol-2-yl | 122–124 |
| 43 | H | O | 4-(3-Trifluoromethylphenyl)thiazol-2-yl | 99–100 |
| 44 | H | O | 4-(4-Trifluoromethylphenyl)thiazol-2-y [sic] | 115–117 |
| 45 | H | O | 2-(4-Fluorophenyl)-5-methylthiazol-4-yl | 126 |
| 46 | H | O | 4-Phenyloxazol-2-yl | 1670,1619,1602,1348,1036 |
| 47 | H | O | 5-Cyclopropylisoxazol-3-yl | 3300,1671,1618,1509,1038 |
| 48 | H | O | 3-(4-Chlorophenyl)-1,2,4-thiadiazol-5-yl | 138–140 |
| 49 | H | O | 1-Phenylpyrazol-3-yl | 80–83 |
| 50 | H | O | 5-Methyl-1-phenylpyrazol-4-yl | 3340,1668,1598,1503,1409, 1036 |
| 51 | H | O | 3-(4-Fluorophenyl)-1,2,4-thiadiazol-5-yl | 105–110 |
| 52 | 3-Cl | O | 1-(4-Chlorophenyl)pyrazol-3-yl | 144–147 |
| 53 | 3-Cl | O | 1-(4-Methylphenyl)pyrazol-3-yl | 3350,1670,1543,1357,1039 |
| 54 | 3-Cl | O | 1-(4-chlorophenyl)pyrazol-4-yl | 2.9(3H); 3.9(3H); 5.0(2H); 6.8(NH); 7.1–7.6(9H) |
| 55 | H | O | 4-(Methoxyiminoethyl)thiazol-2-yl | 115–116 |
| 56 | H | O | 4-(Ethoxyiminoethyl)thiazol-2-yl | 65–67 |
| 57 | H | O | 5-(Methoxyiminoethyl)-4-methylthiazol-2-yl | 104–106 |
| 58 | H | O | 5-(Ethoxyiminoethylyl)-4-methylthiazol-2-yl | 3320,1617,1508,1378,1285, 1048 |

TABLE 1-continued

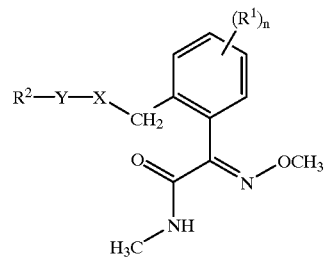

| No. | $R_n^1$ | X | $R^2$—Y | M.p. [° C.]/IR [cm$^{-1}$]/$^1$H—NMR [ppm] |
|---|---|---|---|---|
| 59 | H | O | 1-(n-Chlorophenyl)-1,2,4-triazol-3-yl | 3310,1660,1551,1504,1333, 973 |
| 60 | H | O | 1-(4-Chlorophenyl)-5-methyl-1,2,4-triazol-3-yl | 3330,1670,1541,1350,1036 |
| 61 | H | O | 1-Methyl-5-trifluoromethylpyrazol-3-yl | 57–59 |
| 62 | H | O | 1-(2-Chlorophenyl)pyrazol-3-yl | 80–82 |
| 63 | H | O | 1-(2,4-Dimethylphenyl)pyrazol-3-yl | 3240,1670,1541,1483,1360, 1036 |
| 64 | H | O | 1-(4-Chlorophenyl)-3-methylpyrazol-4-yl | 119–122 |
| 65 | H | O | 5-(5-Methyl-1,2,4-oxadiazol-3-yl)isoxazol-3-yl | 113–115 |
| 66 | H | O | 5-(5-Propyl-1,2,4-oxadiazol-3-yl)isoxazol-3-yl | 3325,2936,1659,1529,1346, 1039 |
| 67 | H | O | 5-(5-Hexyl-1,2,4-oxadiazol-3-yl)isoxazol-3-yl | 3295,2930,1660,1530,1343, 1040 |
| 68 | 3-Cl | O | 4-(4-Chlorophenyl)-1,3-thiazol-2-yl | 68–71 |
| 69 | 3-Cl | O | 4-(2,4-Dichlorophenyl)-1,3-thiazol-2-yl | 128–130 |
| 70 | 3-Cl | O | 1-(2,4-Dichlorophenyl)pyrazol-3-yl | 128–129 |
| 71 | 3-Cl | O | 1-(4-Chlorophenyl)-1,2,4-triazol-3-yl | 171–173 |
| 72 | H | O | 1-(3,4-Dichlorophenyl)pyrazol-3-yl | 3330,1670,1547,1474,1358, 1036 |
| 73 | H | O | 1-(2,5-Dichlorophenyl)pyrazol-3-yl | 3310,1670,1546,1490,1471, 1435,1035 |
| 74 | H | O | 1-(3,5-Dichlorophenyl)pyrazol-3-yl | 154–156 |
| 75 | H | O | 1-(4-Chloro-2-methylphenyl)pyrazol-3-yl | 3320,1669,1543,1479,1350, 1034 |
| 76 | H | O | 1-(4-Methoxyphenyl)pyrazol-3-yl | 3330,1670,1542,1517,1360, 1034 |
| 77 | H | O | 1-(3-Trifluoromethylphenyl)pyrazol-3-yl | 114–116 |
| 78 | H | O | 1-(4-Chlorophenyl)-5-trifluoromethylpyrazol-3-yl | 3330,1669,1567,1505,1139 |
| 79 | H | O | 3-(4-Chlorophenyl)isoxazol-5-yl | 142–145 |
| 80 | H | O | 5-Cyanoisoxazol-3-yl | 2.9(3H); 4.0(3H); 5.15(2H); 6.3(1H); 6.85(1H); 7.2–7.6 (4H) |
| 81 | H | O | 5-Methyl-2-(pyrid-2-yl)-1,3-thiazol-4-yl | 127–128 |
| 82 | H | O | 5-Methyl-2-(pyrid-3-yl)-1,3-thiazol-4-yl | 148–149 |
| 83 | H | O | 5-Methyl-2-(pyrid-4-yl)-1,3-thiazol-4-yl | 136–137 |
| 84 | H | O | 5-Methyl-2-(foran-2-yl)-1,3-thiazol-4-yl | 100–102 |
| 85 | H | O | 5-Methyl-2-(thien-2-yl)-1,3-thiazol-4-yl | 137–138 |
| 86 | H | O | 5-Methyl-2-(3-methylisoxazol-5-yl)-1,3-thiazol-4-yl | 120–122 |
| 87 | H | O | 4-(3-Methylisoxazol-5-yl)-1,3-thiazol-2-yl | 109–111 |
| 88 | H | O | 5-Methyl-2-(2-methyl-1,3-thiazol-4-yl)-1,3-thiazol-4-yl | 88–92 |
| 89 | H | O | 4-(2,4-Dimethyl-1,3-thiazol-5-yl)-1,3-thiazol-4-yl | 129–130 |
| 90 | H | O | 5-Methyl-2-(2-n-heptyl-1,3-thiazol-4-yl)-1,3-thiazol-4-yl | 72–74 |
| 91 | H | O | 4-(2-n-Heptyl-1,3-thiazol-4-yl)-1,3-thiazol-2-yl [sic] | 64–66 |
| 92 | H | O | 1-(2-Methylphenyl)pyrazol-3-yl | 3330,1672,1541,1360,1360, 1035 |
| 93 | H | O | 1-(3-Methylphenyl)pyrazol-3-yl | 3340,1671,1545,1358,1036 |
| 94 | H | O | 5-Methyl-1-phenylpyrazol-3-yl | 138–140 |

TABLE 2

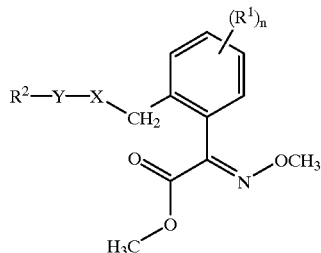

II

| No. | $R_n^1$ | X | $R^2$—Y | M.p. [° C.]/IR [cm$^{-1}$]/$^1$H—NMR [ppm] |
|---|---|---|---|---|
| 1 | H | O | 5-Methylisoxazol-3-yl | 108–110 |
| 2 | H | O | 5-(4-Chlorophenyl)isoxazol-3-yl | 155–157 |
| 3 | H | O | 3-Phenyl-1,2,4-thiadizol-5-yl [sic] | 139–140 |
| 4 | H | S | 5-(4-Chlorophenyl)-1,3,4-oxadizaol-2-yl [sic] | 103–105 |
| 5 | H | S | 5-(4-Methylphenyl)-1,3,4-oxadiazol-2-yl | 135–136 |
| 6 | H | O | 4-(4-Fluorophenyl)-1,3-thiazol-2-yl | 105–106 |
| 7 | H | O | 4-(4-Chlorophenyl)-1,3-thiazol-2-yl | 109–110 |
| 8 | H | O | 4-(2,4-Dichlorophenyl)-1,3-thiazol-2-yl | 136–137 |
| 9 | H | O | 1-Phenyl-1,2,4-triazol-3-yl | 88–90 |
| 10 | H | O | 1-Phenylpyrazol-4-yl | 1726,1597,1503,1400,1358, 1220, 1019 |
| 11 | H | O | 1-(4-Fluorophenyl)pyrazol-4-yl | 1727,1583,1514,1224,1070, 1021 |
| 12 | H | O | 1-(4-Trifluoromethylphenyl)pyrazol-4-yl | 62–84 |
| 13 | H | O | 1-(4-cyanophenyl)pyrazol-4-yl | 156–157 |
| 14 | H | O | 1-(4-Methylphenyl)pyrazol-4-yl | 105–107 |
| 15 | H | O | 1-(4-Chlorophenyl)pyrazol-4-yl | 86–90 |
| 16 | H | O | 1-(2,4-Dichlorophenyl)pyrazol-4-yl | 102–104 |
| 17 | H | O | 5-Trifluoromethylisoxazol-3-yl | 90–93 |
| 18 | H | O | 5-Phenylisoxazol-3-yl | 95–97 |
| 19 | H | O | 1-(2,4-Dichlorophenyl)pyrazol-3-yl | 121 |
| 20 | H | O | 1-(4-Chlorophenyl)pyrazol-3-yl | 112–113 |
| 21 | H | O | 1-(3-Chlorophenyl)pyrazol-3-yl | 80–84 |
| 22 | H | O | 1-(4-Fluorophenyl)pyrazol-3-yl | 105–107 |
| 23 | H | O | 1-(4-Methylphenyl)pyrazol-3-yl | 110–111 |
| 24 | H | S | 1-Methylimidazol-2-yl | 104–108 |
| 25 | H | S | 4-Methyl-1,2,4-triazol-3-yl | 144 |
| 26 | H | O | 4-Acetylthiazol-2-yl | 110–112 |
| 27 | H | O | 4-Isopropylthiazol-2-yl | 1726,1515,1322,1253,1068 |
| 28 | H | O | 4-Isobutylthiazol-2-yl | 1729,1533,1437,1314,1227, 1069 |
| 29 | H | O | 4-(2-Methylphenyl)thiazol-2-yl | 99–100 |
| 30 | H | O | 4-(3-Methylphenyl)thiazol-2-yl | 79–80 |
| 31 | H | O | 4-(4-Methylphenyl)thiazol-2-yl | 121–122 |
| 32 | H | O | 4-(2-Methoxyphenyl)thiazol-2-yl | 111–113 |
| 33 | H | O | 4-(3-Methoxyphenyl)thiazol-2-yl | 78–79 |
| 34 | H | O | 4-(4-Methoxyphenyl)thiazol-2-yl | 132–133 |
| 35 | H | O | 4-(3-Bromophenyl)thiazol-2-yl | 91–94 |
| 36 | H | O | 4-(4-Bromophenyl)thiazol-2-yl | 123–125 |
| 37 | H | O | 4-(3-Trifluoromethylphenyl)thiazol-2-yl | 85–86 |
| 38 | H | O | 4-(4-Trifluoromethylphenyl)thiazol-2-yl | 94–95 |
| 39 | H | O | 2-(4-Fluorophenyl)-5-methylthiazol-4-yl | 105–106 |
| 40 | H | O | 5-Cyclopropylisoxazol-3-yl | 103–105 |
| 41 | H | O | 3-(4-Chlorophenyl)-1,2,4-thiadiazol-5-yl | 139–140 |
| 42 | H | O | 1-Phenylpyrazol-3-yl | 80–83 |
| 43 | H | O | 5-Methyl-1-phenylpyrazol-4-yl | 1726,1598,1503,1361,1188, 1069 |
| 44 | H | O | 3-(4-Fluorophenyl)-1,2,4-thiadiazol-5-yl | 153–155 |
| 45 | 3-Cl | O | 1-(4-Chlorophenyl)pyrazol-3-yl | 100–104 |
| 46 | 3-Cl | O | 1-(4-Methylphenyl)pyrazol-3-yl | 141–146 |
| 47 | H | O | 4-(Methoxyiminoethyl)thiazol-2-yl | 105–106 |
| 48 | H | O | 4-(Ethoxyiminoethyl)thiazol-2-yl | 92–93 |
| 49 | H | O | 5-(Methoxyiminoethyl)-4-methylthazol-2-yl [sic] | 75–76 |
| 50 | H | O | 5-(Ethoxyiminoethyl)-4-methylthiazol-2-yl | 95–97 |
| 51 | H | O | 1-(n-Chlorophenyl)-1,2,4-triazol-3-yl | 95 |
| 52 | H | O | 1-(4-Chlorophenyl)-5-methyl-1,2,4-triazol-3-yl | 1729,1539,1434,1350,1018 |
| 53 | H | O | 1-Methyl-5-trifluoromethylpyrazol-3-yl | 50–52 |
| 54 | H | O | 1-(2-Chlorophenyl)pyrazol-3-yl | 85–87 |
| 55 | H | O | 1-(2,4-Dimethylphenyl)pyrazol-3-yl | 95–100 |
| 56 | H | O | 1-(4-Chlorophenyl)-3-methylpyrazol-4-yl | 109–114 |
| 57 | H | O | 5-(5-Methyl-1,2,4-oxadiazol-3-yl)isoxazol-3-yl | 128–131 |
| 58 | H | O | 5-(5-Propyl-1,2,4-oxadiazol-3-yl)isoxazol-3-yl | 73–74 |

TABLE 2-continued

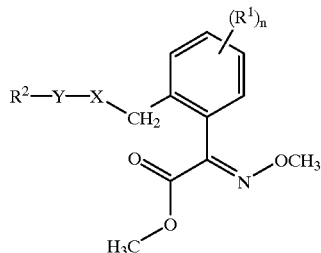

| No. | $R_n^1$ | X | $R^2$—Y | M.p. [° C.]/IR [cm$^{-1}$]/$^1$H—NMR [ppm] |
|---|---|---|---|---|
| 59 | H | O | 5-(5-Hexyl-1,2,4-oxadiazol-3-yl)isoxazol-3-yl | 1728,1526,1439,1359,1221, 1069 |
| 60 | H | O | 1-Methyl-3-phenyl-1,2,4-triazol-5-yl | 110 |
| 61 | H | O | 1-(3,5-Dichlorophenyl)-1,2,4-triazol-3-yl | 157–160 |
| 62 | H | O | 5-Ethyl-1-phenyl-1,2,4-triazol-3-yl | 88–91 |
| 63 | H | O | 1-(2,4-Dichlorophenyl)-1,2,4-triazol-3-yl | 129–131 |
| 64 | H | O | 1-(2,6-Dichlorophenyl)pyrazol-3-yl | 128–130 |
| 65 | 3-Cl | O | 4-(4-Chlorophenyl)-1,3-thiazol-2-yl | 154–155 |
| 66 | 3-Cl | O | 4-(2,4-Dichlorophenyl)-1,3-thiazol-2-yl | 155–158 |
| 67 | 3-Cl | O | 1-(2,4-Dichlorophenyl)pyrazol-3-yl | 133–135 |
| 68 | 3-Cl | O | 1-(4-Chlorophenyl)-1,2,4-triazol-3-yl | 130–131 |
| 69 | H | O | 1-(3,4-Dichlorophenyl)pyrazol-3-yl | 95–97 |
| 70 | H | O | 1-(2,5-Dichlorophenyl)pyrazol-3-yl | 90–93 |
| 71 | H | O | 1-(3,5-Dichlorophenyl)pyrazol-3-yl | 130–132 |
| 72 | H | O | 1-(4-Chloro-2-methylphenyl)pyrazol-3-yl | 113–155 |
| 73 | H | O | 1-(4-Methoxyphenyl)pyrazol-3-yl | 102–105 |
| 74 | H | O | 1-(3-Trifluoromethylphenyl)pyrazol-3-yl | 109–111 |
| 75 | H | O | 3-(4-Chlorophenyl)isoxazol-5-yl | 113–114 |
| 76 | H | O | 5-Cyanoisoxazol-3-yl | 105–107 |
| 77 | H | O | 5-Methyl-2-(pyrid-2-yl)-1,3-thiazol-4-yl | 105–107 |
| 78 | H | O | 5-Methyl-2-(pyrid-3-yl)-1,3-thiazol-4-yl | 97–98 |
| 79 | H | O | 5-Methyl-2-(pyrid-4-yl)-1,3-thiazol-4-yl | 146–147 |
| 80 | H | O | 5-Methyl-2-(furan-2-yl)-1,3,thiazol-4-yl [sic] | 92–93 |
| 81 | H | O | 5-Methyl-2-(thien-2-yl)-1,3-thiazol-4-yl | 109–110 |
| 82 | H | O | 5-Methyl-2-(3-methyl-isoxazol-5-yl)-1,3-thiazol-4-yl | 111–113 |
| 83 | H | O | 4-(3-Methylisoxazol-5-yl)-1,3-thiazol-2-yl | 98–100 |
| 84 | H | O | 5-Methyl-2-(2-methyl-1,3,thiazol-4-yl)-1,3-thiazol-4-yl [sic] | 96–97 |
| 85 | H | O | 4-(2,4-Dimethyl-1,3-thiazol-5-yl)-1,3-thiazol-4-yl | 117–118 |
| 86 | H | O | 5-Methyl-2-(2-n-heptyl-1,3-thiazol-4-yl)-1,3-thiazol-4-yl | 73–75 |
| 87 | H | O | 4-(2-n-Heptyl-1,3-thiazol-4-yl)-1,3-thiazol-2-yl | 73–75 |
| 88 | H | O | 5-Methyl-2-phenyl-1,3-thiazol-2-yl | 108–110 |
| 89 | H | O | 5-Methoxycarbonylisoxazol-3-yl | 77–78 |
| 90 | H | O | 5-Carbamoylisoxazol-3-yl | 142–145 |
| 91 | H | O | 5-(1,2,4-Oxadiazol-3-yl)isoxazol-3-yl | 122–123 |
| 92 | H | O | 4-Methoxycarbonyl-1-phenylpyrazol-3-yl | 90–93 |
| 93 | H | O | 1-(2-Methylphenyl)pyrazol-3-yl | 81–85 |
| 94 | H | O | 5-(5-Mercapto-1,3,4-oxadiazol-2-yl)isoxazol-3-yl | 3348,1730,1556,1478,1368, 1071 |
| 95 | H | O | 5-(5-Hydroxy-1,3,4-oxadiazol-2-yl)isoxazol-3-yl [sic] | 3260,1816,1803,1780,1734, 1559,1502,1353,1066 |

The compounds I are suitable as fungicides.

The compounds I are distinguished by an outstanding activity against a broad spectrum of phytopathogenic fungi, in particular from the class of Ascomycetes and Basidiomycetes. They are systemically active in some cases and can be employed as foliar and soil fungicides.

They are of particular importance for the control of a multiplicity of fungi on various crop plants such as wheat, rye, barley, oats, rice, corn, grass, cotton, soybean, coffee, sugarcane, grapes, fruit and decorative plants and vegetable plants such as cucumbers, beans and Cucurbitaceae, and on the seeds of these plants.

They are specifically suitable for the control of the following plant diseases:

*Erysiphe graminis* (powdery mildew) in cereals, *Erysiphe cichoracearum* and *Sphaerotheca fuliginea* on Cucurbitaceae, *Podosphaera leucotricha* on apples, *Uncinula necator* on vines, Puccinia species on cereals, Rhizoctonia species on cotton and lawns, Ustilago species on cereals and sugarcane, *Venturia inaequalis* (scab) on apples, Helminthosporium species on cereals, *Septoria nodorum* on wheat, *Botrytis cinerea* (gray mold) on strawberries, vines, *Cercospora arachidicola* on groundnuts, *Pseudocercosporella herpotrichoides* on wheat, barley, *Pyricularia oryzae* on rice, *Phytophthora infestans* on potatoes and tomatoes, Fusarium and Verticillium species on various plants, *Plasmopara viticola* on vines, Alternaria species on vegetables and fruit.

The compounds I are applied by treating the fungi or the plants, seeds, materials or the soil to be protected from fungal attack with a fungicidally effective amount of the active compounds. They are applied before or after the infection of the materials, plants or seeds by the fungi.

They can be converted into the customary formulations, such as solutions, emulsions, suspensions, dusts, powders, pastes and granules. The application form depends on the particular intended use; they should in any case guarantee a fine and uniform dispersion of the ortho-substituted benzyl ester of a cyclopropanecarboxylic acid. The formulations are prepared in a known manner, eg. by extending the active compound with solvents and/or carriers, if desired using emulsifiers and dispersants, it also being possible to use other organic solvents as auxiliary solvent when water is used as a diluent. Suitable auxiliary substances for this purpose are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silicic acid, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

The fungicidal compositions in general contain from 0.1 to 95, preferably from 0.5 to 90, % by weight of active compound.

Depending on the type of effect desired, the application rates are from 0.02 to 3 kg of active compound per ha.

In seed treatment, active compound amounts of from 0.001 to 50 g, preferably 0.01 to 10 g, per kilogram of seed are in general needed.

The compositions according to the invention can also be present as fungicides together with other active compounds in the application form, the [sic] eg. with herbicides, insecticides, growth regulators, fungicides or alternatively with fertilizers.

On mixing with fungicides, in many cases an enlargement of the fungicidal spectrum of action is obtained here.

The following list of fungicides with which the compounds according to the invention can be applied together should illustrate the combination possibilities, but not restrict it:

sulfur, dithiocarbamtates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropylcarbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazole carbamate, 2-methoxycarbonylaminobenzimidazole, 2-(fur-2-yl) benzimidazole, 2-(thiazol-4-yl)benzimidazole, N-(1,1, 2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfadimide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine-1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl)formamide [sic], 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl] glutarimide, hexachlorobenzene, DL-methyl-N-(2,6-dimethylphenyl)-N- 2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1, 3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylaminocarbonyl-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2, 6-dinitro-4-trifluoromethylphenyl)-5-trifluoromethyl-3-chloro-2-aminopyridine, 1-((bis (4-fluorophenyl) methylsilyl)methyl)-1H-1,2,4-triazole.

The following active compounds are particularly preferred as mixture components:

1-(2-cyano-2-methoxyiminoacetyl)-3-ethylurea (common name: cymoxanil, U.S. Pat. No. 3,957,847); manganese ethylenebis(dithiocarbamate zinc complex) (common name: mancozeb, U.S. Pat. No. 3,379,610);

manganese ethylenebis(dithiocarbamate) (common name: maneb, U.S. Pat. No. 2,504,404); zinc ammoniate ethylenebis(dithiocarbamate) (former common name: metiram, U.S. Pat. No. 3,248,400); zinc ethylenebis(dithiocarbamate) (common name: zineb, U.S. Pat. No. 2,457,674), (#)-cis-4-[3-(4-tert-butylphenyl)-2-methylpropyl]-2,6-dimethylmorpholine [sic] (common name: fenpropimorph, U.S. Pat. No. 4,202,894); (RS)-1-[3-(4-tert-butylphenyl)-2-methylpropyl]piperidine (common name: fenpropidin, U.S. Pat. No. 4,202,894); 2,6-dimethyl-4-[$C_{11}$–$C_{14}$-alkyl]morpholine (common name: tridemorph, DE-A 11 64 152); 1-[(2RS,4RS;2RS,4SR)-4-bromo-2-(2,4-dichlorophenyl)tetrahydrofuryl]-1H-1,2,4-triazol [common name: bromuconazole, Proc. Br. Crop Prot. Conf. Pests Dis., 5–6, (1990) 439]; 2-(4-chlorophenyl)-3-cyclopropyl-1-(1H-1,2,4-triazol-1-yl)butan-2-ol (common name: cyproconazole, U.S. Pat. No. 4,664, 696); (#)-4-chloro-4-[4-methyl-2-(1H-1,2,4-triazol-1-ylmethyl)-1,3-dioxolan-2-yl]phenyl [sic] 4-chlorophenyl ether (common name: difenoconazole, GB-A 2,098,607); (E)-(R,S)-1-(2,4-dichlorophenyl)-4,4-dimethyl-2-(1H-1,2,4-triazol-1-yl)pent-1-en-3-ol (common name: diniconazole, CAS RN [83657-24-3]); (Z)-2-(1H-1,2,4-triazol-1-ylmethyl)-2-(4-fluorophenyl)-3-(2-chlorophenyl)oxirane (common name: epoxyconazole, EP-A 196 038); 4-(4-chlorophenyl)-2-phenyl-2-(1H-1,2,4-triazolylmethyl)butyronitrile (common name: fenbuconazole (proposed), EP-A 251 775); 3-(2,4-dichlorophenyl)-6-fluoro-2-(1H-1,2,4-triazol-1-yl)quinazolin-4(3H)one [common name: fluquinconazole, Proc. Br. Crop Prot. Conf. Pests Dis., 5-3, (1992) 411]; bis(4-fluorophenyl)(methyl) (1H-1,2,4-triazol-1-ylmethyl)silane [common name: flusilazole, Proc. Br. Crop Prot. Conf. Pests Dis., 1, (1984) 413]; (R,S)-2-(2,4-dichlorophenyl)-1-(1H-1,2,4-triazol-1-yl)hexan-2-ol (common name: hexaconazole, CAS RN [79983-71-4]); (1RS,5RS;1RS,5SR)-5-(4-chlorobenzyl)-2,2-dimenthyl-1-(1H-1,2,4-triazol-1-ylmethyl)cyclopentanol [common name: metconazole, Proc. Br. Crop Prot. Conf. Pests Dis., 5-4, (1992) 419]; N-propyl-N-[2-(2,4,6-trichlorophenoxy)ethyl]imidazole-1-carboxamide (common name: prochloraz, U.S. Pat. No. 3,991,071); (±)-1-[2-(2,4-dichlorophenyl)-4-propyl-1,3-dioxolan-2-ylmethyl]-1H-1,2,4-triazole (common name: propiconazole, GB-A 1,522,657); (R,S)-1-(4-chlorophenyl)-4,4-dimethyl-3-(1H-1,2,4-triazol-1-ylmethyl)pentan-3-ol (common name: tebuconazole, U.S. Pat. No. 4,723,984); (±)-2-(2,4-dichlorophenyl)-3-(1H-1,2,4-triazol-1-yl)propyl 1,1,2,2-tetrafluoroethyl ether [common name: tetraconazole, Proc. Br. Crop Prot. Conf. Pests Dis., 1, (1988) 49]; (E)-1-[1-[[4-chloro-2-(trifluoromethyl)phenyl]imino]-2-propoxyethyl]-1H-imidazole (common name: triflumizole, JP-A 79/119,462); (RS)-2,4'-difluoro-alpha-(1H-1,2,4-triazol-1-ylmethyl)benzhydryl alcohol (common name: flutriafol, CAS RN [76674-21-0]); 1-[2-(2,5-dimethylphenoxymethyl)phenyl]-1-methoxyimino-N-methylacetamide (EP-A 477 631); methyl 1-[2-(2-methylphenoxymethyl)phenyl]-1-methoxyiminoacetate (EP-A 253 213); methyl 1-{2-[6-(3-cyanophenoxy)pyrimidin-4-yloxy]phenyl}-1-methoxyiminoacetate (EP-A 382 375); N-(trichloromethylthio)cyclohex-4-ene-1,2-dicarbimide (common name: captan, U.S. Pat. No. 2,553,770); N-(trichloromethylthio)phthalimide (common name: folpet, U.S. Pat. No. 2,553,770); 4,6-dimethyl-2-phenylaminopyrimidine (common name: pyrimethanil, DD-A 151 404); 4-methyl-2-phenylamino-6-propynylpyrimidine (common name: mepanipyrim, EP-A 224 339); 4-cyclopropyl-6-methyl-2-phenylaminopyrimidine (EP-A 310 550).

The compounds of the formula I are additionally suitable to control pests from the class of insects, arachnida and nematodes effectively. They can be employed as pesticides in plant protection and in the hygiene, stored products protection and veterinary sector.

The harmful insects include from the order of the butterflies (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grndiosella* [sic], *Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Petcinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotetra chrysocephala, Phyllophaga sp., Phyllopertha horticola, Phyllotetra nemorum, Phyllotetra striolata, Popilla japonica, Sitona lineatus, Sitophilus granaria.*

From the order of the dipterous insects (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura*

*brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucila caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterous insects (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the bed bugs (Heteroptera), for example, *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis, Thyanta perditor.*

From the order of the plant-sucking insects (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterous insects (Orthoptera), for example, *Acheta domestica, Blatta orientalis, Blattella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example spiders (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius, Tetranychus urticae.*

From the class of the nematodes, for example, root gall nematodes, eg. *Meloidogyne hapla, Meloidogyne incognita,* *Meloidogyne javanica,* cyst-forming nematodes, eg. *Globodera rostochiensis, Heterodera avenae, Heterodera glycinae, Heterodera schatii, Heterodera trifolii,* stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active compounds can be applied as such or in the form of their formulations or the application forms prepared therefrom, eg. in the form of directly sprayable solutions, powders, suspensions or dispersions, emulsions, oil dispersions, pastes, dusts, scattering compositions or granules by spraying, atomizing, dusting, scattering or pouring. The application forms depend entirely on the purposes of use; they should in any case as far as possible guarantee the finest dispersion of the active compounds according to the invention.

The active compound concentrations in the ready-for-application preparations can be varied within substantial ranges.

In general, they are from 0.0001 to 10%, preferably from 0.01 to 1%.

The active compounds can also be used with success in ultra-low volume processes (ULV), where it is possible to apply formulations containing more than 95% by weight of active compound or even the active compound without additives.

The application rates of active compound for controlling pests under outdoor conditions is from 0.1 to 2.0, preferably from 0.2 to 1.0 kg/ha.

For the preparation of directly sprayable solutions, emulsions, pastes or oil dispersions, mineral oil fractions of medium to high boiling points, such as kerosene or diesel oil, and also coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water are suitable.

Aqueous application forms can be prepared from emulsion concentrates, pastes or wettable powders (oil dispersions) by addition of water. For the preparation of emulsions, pastes or oil dispersions, the substances can be homogenized in water as such or dissolved in an oil or solvent, by means of wetting agents, tackifiers, dispersants or emulsifiers. However, the concentrates consisting of active substance, wetting agent, tackifier, dispersant or emulsifier and possibly solvent or oil can also be prepared, which are suitable for dilution with water.

Suitable surface-active substances are alkali metal, alkaline earth metal and ammonium salts of lignosulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol [sic] ether, ethoxylated isooctylphenol, octylphenol, nonylphenol, alkylphenol [sic]

polyglycol ether, tributylphenyl polyglycol ether, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, scattering compositions and dusts can be prepared by mixing or joint grinding of the active substances with a solid carrier.

The formulations in general contain from 0.01 to 95% by weight, preferably from 0.1 to 90% by weight, of the active compound. The active compounds are employed here in a purity of from 90% to 100%, preferably 95% to 100% (according to NMR spectrum).

Examples of formulations are:

I. 5 parts by weight of the compound No. 1 from Table B are intimately mixed with 95 parts by weight of finely divided kaolin. A dust which contains 5% by weight of the active compound is obtained in this way.

II. 30 parts by weight of the compound No. 2 from Table B are intimately mixed with a mixture of 92 parts by weight of powdered silica gel and 8 parts by weight of paraffin oil which has been sprayed on the surface of this silica gel. A preparation of the active compound having good adhesion is obtained in this way (active compound content 23% by weight).

III. 10 parts by weight of the compound No. 3 from Table B are dissolved in a mixture which consists of 90 parts by weight of xylene, 6 parts by weight of the addition product of 8 to 10 mol of ethylene oxide to 1 mol of oleic acid N-monoethanolamide, 2 parts by weight of calcium salt of dodecylbenzenesulfonic acid and 2 parts by weight of the addition product of 40 mol of ethylene oxide to 1 mol of castor oil (active compound content 9% by weight).

IV. 20 parts by weight of the compound No. 4 from Table B are dissolved in a mixture which consists of 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of the compound No. 5 from Table B are well mixed with 3 parts by weight of the sodium salt of diisobutylnaphthalene-alpha-sulfonic acid, 10 parts by weight of the sodium salt of a lignosulfonic acid from a sulfite waste liquor and 7 parts by weight of powdered silica gel and the mixture is ground in a hammer mill (active compound content 80% by weight).

VI. 90 parts by weight of the compound No. 6 from Table B are mixed with 10 parts by weight of N-methyl-α-pyrrolidone and a solution is obtained which is suitable for application in the form of very small drops (active compound content 90% by weight).

VII. 20 parts by weight of the compound No. 7 from Table B are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

VIII. 20 parts by weight of the active compound No. 8 from Table B are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray liquor is obtained which contains 0.1% by weight of the active compound.

Granules, eg. coated, impregnated and homogeneous granules, can be produced by binding the active compounds to solid carriers. Solid carriers are eg. mineral earths, such as silica gel, silicic acids, silica gels (sic), silicates, talc, kaolin, attapulgite, limestone, lime, chalk, bole, loess, clay, dolomite, diatomaceous earth, calcium sulfate and magnesium sulfate, magnesium oxide, ground synthetic materials, fertilizers, such as eg. ammonium sulfate, ammonium phosphate, ammonium nitrate, ureas and vegetable products, such as grain meal, tree bark, wood and nut shell meal, cellulose powder and other solid carriers.

Oils of various types, herbicides, fungicides, other pesticides and bactericides can be added to the active compounds, if appropriate also just immediately before application (tank mix). These agents can be admixed to the compositions according to the invention in the weight ratio 1:10–10:1.

Application Examples

1. Fungicidal Activity

It was possible to show the fungicidal action of the compounds of the general formula I by the following tests:

The active compounds were prepared as a 20% strength emulsion in a mixture of 70% by weight of cyclohexanol, 20% by weight of Nekanil® LN (Lutensol® AP6, wetting agent with emulsifier and dispersant action based on ethoxylated alkylphenols) and 10% by weight of Emulphor® EL (Emulan® EL, emulsifier based on ethoxylated fatty alcohols) and accordingly diluted to the desired concentration with water.

1.A *Erysiphe graminis* var. *tritici* (Wheat Mildew)

Wheat seedlings of the variety Frühgold were sprayed with an aqueous active compound suspension until dripping wet. After 24 h, the plants were dusted with oidia (spores) of the fungus *Erysiphe graminis* var. *tritici* (wheat mildew). After 7 days at 22° C.–24° C. and 75–80% atmospheric humidity, the fungal infestation of the leaves was assessed.

In this test, the plants treated with 63 ppm of the compounds 3, 7, 8, 9, 11, 12, 14, 18, 19, 23, 27, 32, 33, 35, 49, 50, 51, 53, 54, 55, 56, 57, 58 and 59 showed an infestation of 15% and less, while in the untreated plants 65% of the leaf surfaces were infested.

1.B *Plasmopara viticola* (Vine Peronospora)

Potted vines of the variety Müller-Thurgau were sprayed with an aqueous active compound suspension until dripping wet. After 8 days in the greenhouse, the leaves were infected with a zoospore suspension of *Plasmopara viticola* (vine Peronospora). The plants were first placed for 48 hours at 24° C. in a water vapor-saturated chamber, then for 5 days in the greenhouse at 20° C.–30° C. and subsequently for a further 16 hours at 24° C. in a water vapor-saturated chamber before the infestation was assessed.

In this test, the plants treated with 63 ppm of the compounds 3, 7, 8, 9, 10, 11, 12, 14, 15, 16, 17, 18, 21, 22, 23, 24, 25, 26, 27, 33, 34, 35, 36, 37, 38, 39, 40, 41, 42, 23 [sic], 44 and 48 showed an infestation of 15% and less, while in the untreated plants 80% of the leaf undersides were infested.

1.C *Pyricularia oryzae* (Protective Action)

Leaves of rice seedlings of the variety Tai-Nong 67 were sprayed with aqueous emulsions of the active compounds (content of dry matter: 80% active compound and 20% emulsifier) until dripping wet and inoculated 24 hours later with a spore suspension of *Pyricularia oryzae*. The test plants were then stored in climatic chambers at 22–24 ° C. and 95–99% relative atmospheric humidity. After 6 days, the extent of the infestation was determined.

In this test, the plants treated with 250 ppm of the compounds 3, 7, 8, 10, 11, 12, 20, 21, 22, 23, 24, 25, 26, 27, 32, 33, 38, 48, 49, 50, 51, 52, 53, 54 and 55 showed an infestation of 15% and less, while in the untreated plants 70% of the leaf surfaces were infested.

2. Action Against Animal Pests

It was possible to show the insecticidal action of the compounds of the general formula I by the following tests:

The Active Compounds Were Prepared a) as a 0.1% strength solution in acetone or b) as a 10% strength emulsion in a mixture of 70% by weight of cyclohexanone, 20% by weight of Nekanil® LN (Lutensol® AP6, wetting agent with emulsifier and dispersant action based on ethoxylated alkylphenols) and 10% by weight of Emulphor® EL (Emulan® EL, emulsifier based on ethoxylated fatty alcohols)

and diluted with acetone in the case of a) or with water in the case of b) according to the desired concentration.

After conclusion of the tests, the lowest concentration in each case was determined at which the compounds still caused a 80–100% inhibition or mortality in comparison to untreated control tests (activity threshold or minimum concentration respectively).

2.A *Aphis fabae* (Blackfly), Contact Action

Heavily infested bush beans (*Vicia faba*) were treated with the aqueous active compound preparation.

The mortality rate was determined after 24 h.

In this test, the compounds 9, 18, 24, 37, 42, 43 and 44 showed activity thresholds of at least 400 ppm.

2.B *Nephotettix cincticeps* (Green Rice Cicada), Contact Action

Round filters were treated with the aqueous active compound preparation and then subjected to occupation by 5 adult cicadas.

The mortality was assessed after 24 h.

In this test, the compounds 3, 16, 24, 32, 33, 36, 40, 42, 46, 50, 51, 55, 56, 58, 61 and 63 showed activity thresholds of at least 0.4 mg.

2.C *Prodenia litura* (Egyptian Cotton Leafworm), Growth Test

Five caterpillars of the development stage L3 (10–12 mm) which had suffered no ascertainable damage in the contact test were applied to standard nutrient medium (3.1 l of water, 80 g of agar, 137 g of brewer's yeast, 515 g of corn meal, 130 g of wheatgerm and customary additives and vitamins (20 g of Wesson salt, 5 g of Nipagin, 5 g of Sorbin, 10 g of cellulose, 18 g of ascorbic acid, 1 g of Lutavit® blend (vitamin), 5 ml of alcoholic biotin solution), which had previously been wetted with the aqueous active compound preparation. The observation extended until hatching of the moths in a control test without active compound.

In this test, the compounds 9, 24, 26, 40, 42, 43, 44, 51, 52 and 63 showed activity thresholds of at least 0.4 mg.

2.D *Tetranychus telarius* (Red Spider Mite), Contact Action

Heavily infested potted bush beans which had the second pair of adult leaves were treated with aqueous active compound preparation.

After 5 days in the greenhouse, the success of the control was determined by means of a binocular microscope.

In this test, the compounds 7, 8, 9, 18, 23, 24, 37, 40, 42, 23 [sic], 44, 49, 50, 51, 52, 61 and 63 showed activity thresholds of at least 400 ppm.

We claim:

1. A compound of the formula I

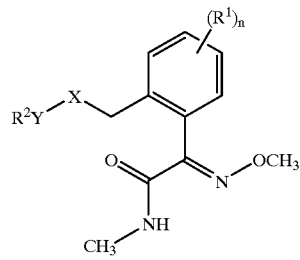

where n is 0;

X is O;

Y is 3-pyrazolyl; and $R^2$ 4-chlorophenyl.

2. A compound of the formula I

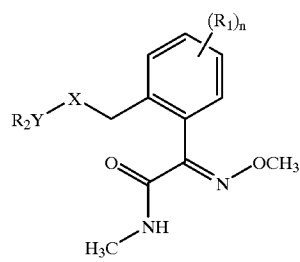

where the index and the substituents have the following meanings $R^2$ is phenyl, Y is pyrazole, X is O or S, and n is 0.

3. A compound of the formula I

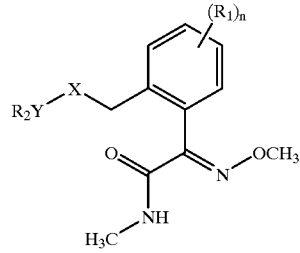

where the index and the substituents have the following meanings wherein $R^2$ is phenyl Y is pyrazole, X is O and n is 0.

* * * * *